United States Patent
Hawkes et al.

(10) Patent No.: US 9,388,393 B2
(45) Date of Patent: *Jul. 12, 2016

(54) MUTANT HYDROXYPHENYLPYRUVATE DIOXYGENASE POLYPEPTIDES AND METHODS OF USE

(75) Inventors: Timothy Robert Hawkes, Bracknell (GB); Michael Phillip Langford, Bracknell (GB); Russell Colin Viner, Bracknell (GB); Bernardus Theodorus Maria Vernooij, Research Triangle, NC (US); Richard Dale, Bracknell (GB)

(73) Assignee: Syngenta Participations AG, Basel (CH)

(*) Notice: Subject to any disclaimer, the term of this patent is extended or adjusted under 35 U.S.C. 154(b) by 900 days.

This patent is subject to a terminal disclaimer.

(21) Appl. No.: 13/584,087

(22) Filed: Aug. 13, 2012

(65) Prior Publication Data

US 2012/0331580 A1 Dec. 27, 2012

Related U.S. Application Data

(62) Division of application No. 12/692,552, filed on Jan. 22, 2010, now Pat. No. 8,269,068.

(60) Provisional application No. 61/224,661, filed on Jul. 10, 2009, provisional application No. 61/146,513, filed on Jan. 22, 2009.

(51) Int. Cl.
| | |
|---|---|
| *A01H 5/00* | (2006.01) |
| *A01H 5/10* | (2006.01) |
| *C12N 15/82* | (2006.01) |
| *C12N 15/53* | (2006.01) |
| *C12N 9/04* | (2006.01) |
| *C12N 9/02* | (2006.01) |
| *C12N 15/01* | (2006.01) |
| *C12N 15/09* | (2006.01) |
| *C12N 15/00* | (2006.01) |

(52) U.S. Cl.
CPC .............. *C12N 9/0069* (2013.01); *C12N 15/00* (2013.01); *C12N 15/01* (2013.01); *C12N 15/09* (2013.01); *C12N 15/8274* (2013.01); *C12Y 113/11027* (2013.01)

(58) Field of Classification Search
None
See application file for complete search history.

(56) References Cited

U.S. PATENT DOCUMENTS

| | | | | |
|---|---|---|---|---|
| 6,118,050 A | * | 9/2000 | Sturner et al. ................. | 800/298 |
| 6,245,968 B1 | | 6/2001 | Boudec et al. | |
| 7,119,255 B2 | | 10/2006 | Betts et al. | |
| 7,166,770 B2 | | 1/2007 | Hohn et al. | |
| 7,312,379 B2 | | 12/2007 | Andrews et al. | |
| 7,622,641 B2 | * | 11/2009 | McCutchen et al. ........... | 800/300 |
| 8,269,068 B2 | * | 9/2012 | Hawkes et al. ................ | 800/300 |
| 9,047,177 B2 | * | 6/2015 | Matsudaira et al. | |
| 9,051,545 B2 | * | 6/2015 | Hawkes et al. | |
| 9,051,546 B2 | * | 6/2015 | Hawkes et al. | |
| 2003/0041357 A1 | | 2/2003 | Jepson et al. | |
| 2003/0200560 A1 | | 10/2003 | Warner et al. | |
| 2004/0034889 A1 | | 2/2004 | Khan et al. | |
| 2005/0246800 A1 | | 11/2005 | Dunne et al. | |
| 2008/0076178 A1 | | 3/2008 | Andrews et al. | |
| 2008/0146447 A1 | | 6/2008 | Andrews et al. | |
| 2009/0011936 A1 | | 1/2009 | Hawkes et al. | |
| 2009/0031442 A1 | | 1/2009 | Andrews et al. | |
| 2009/0055976 A1 | | 2/2009 | Andrews et al. | |
| 2009/0172831 A1 | | 7/2009 | Andrews et al. | |
| 2009/0229006 A1 | | 9/2009 | Jepson et al. | |

FOREIGN PATENT DOCUMENTS

| | | |
|---|---|---|
| WO | 97/49816 | 12/1997 |
| WO | 98/04685 | 2/1998 |
| WO | 98/20144 | 5/1998 |
| WO | 99/04021 | 1/1999 |
| WO | 00/32757 | 6/2000 |
| WO | 02/46387 | 6/2002 |
| WO | 2008/150473 | 12/2008 |
| WO | 2009/144079 | 12/2009 |

OTHER PUBLICATIONS

GenBank Accession No. XP_004951787.1. (2013).*
GenBank Accession PDB: 1SP8_A, first available online Nov. 10, 2004.*
GenBank Accession CCY826664 (2013).*
Fritze et al (Plant Physiol. 134 (4), 1388-1400 (2004).*
Fritze et al., Plant Physiol, vol. 134, pp. 1388-1400, Apr. 2004.
International Search Report dated Aug. 30, 2010, issued in corresponding International Application No. PCT/US2010/021879.
File History of U.S. Appl. No. 12/692,552.

* cited by examiner

Primary Examiner — Lee A Visone
(74) Attorney, Agent, or Firm — S. Matthew Edwards

(57) ABSTRACT

Compositions and methods for conferring hydroxyphenyl pyruvate dioxygenase (HPPD) herbicide resistance or tolerance to plants are provided. Compositions include amino acid sequences, and variants and fragments thereof, for mutant HPPD polypeptides. Nucleic acids that encode the mutant HPPD polypeptides are also provided. Methods for conferring herbicide resistance or tolerance, particularly resistance or tolerance to certain classes of herbicides that inhibit HPPD, in plants are further provided. Methods are also provided for selectively controlling weeds in a field at a crop locus and for the assay, characterization, identification and selection of the mutant HPPDs of the current invention that provide herbicide tolerance.

33 Claims, 11 Drawing Sheets

SEQUENCE LISTING

```
<160> NUMBER OF SEQ ID NOS: 80

<210> SEQ ID NO 1
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 1
atgcctccta ctcctgctac tgctactgga gctgctgctg ctgctgtaac tcctgaacat     60
gctgctagat cttttcctag agtagtaaga gtaaatccta gatctgatag atttcctgta    120 ttatctttc atcatgtaga attatggtgt gctgatgctg cttctgctgc tggaagattt    180
tcttttgctt taggagctcc tttagctgct agatctgatt tatctactgg aaattctgct    240
catgcttctt tattattaag atctggagct ttagctttt tatttactgc tccttatgct    300
cctcctcctc aagaagctgc tactgctgct actgcttcta ttccttcttt ttctgctgat    360
gctgctagaa cttttgctgc tgctcatgga ttagctgtaa gatctgtagg agtaagagta    420
```

```
gctgatgctg ctgaagcttt tagagtatct gtagctggag gagctagacc tgcttttgct    480
cctgctgatt taggacatgg atttggatta gctgaagtag aattatatgg agatgtagta    540
ttaagatttg tatcttatcc tgatgaaact gatttacctt ttttacctgg atttgaaaga    600
gtatcttctc ctggagctgt agattatgga ttaactagat tgatcatgt  agtaggaaat    660 gtacctgaaa tggctcctgt aattgattat atgaaaggat ttttaggatt tcatgaattt    720
gctgaattta ctgctgaaga tgtaggaact actgaatctg gattaaattc tgtagtatta    780
gctaataatt ctgaagctgt attattacct ttaaatgaac tgtacatgg  aactaaaaga    840 agatctcaaa ttcaaactta tttagaatat catggaggac tggagtaca  acatattgct    900 ttagcttcta atgatgtatt aagaacttta agagaaatga gagctagaac tcctatggga    960
ggatttgaat ttatggctcc tcctcaagct aaatattatg aaggagtaag aagaattgct   1020
ggagatgtat tatctgaaga acaaattaaa gaatgtcaag aattaggagt attagtagat   1080
agagatgatc aaggagtatt attacaaatt tttactaaac ctgtaggaga tagacctact   1140
ttttttttag aaatgattca aagaattgga tgtatggaaa aagatgaagt aggacaagaa   1200
tatcaaaaag gaggatgtgg aggatttgga aaaggaaatt ttctgaatt  atttaaatct   1260 attgaagatt atgaaaaatc tttagaagta aaacaatctg tagtagctca aaaatct       1317
```

<210> SEQ ID NO 2
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 2

```
atgcctccta ctcctgctac tgctactgga gctgctgctg ctgctgtaac tcctgaacat     60
gctgctagat ctttttcctag agtagtaaga gtaaatccta gatctgatag atttcctgta    120 ttatctttc  atcatgtaga attatggtgt gctgatgctg cttctgctgc tggaagattt    180
tcttttgctt taggagctcc tttagctgct agatctgatt tatctactgg aaattctgct    240
catgcttctt tattattaag atctggagct ttagcttttt tatttactgc tccttatgct    300
cctcctcctc aagaagctgc tactgctgct actgcttcta tccttctttt ttctgctgat    360
gctgctagaa cttttgctgc tgctcatgga ttagctgtaa gatctgtagg agtaagagta    420
gctgatgctg ctgaagcttt tagagtatct gtagctggag gagctagacc tgcttttgct    480
cctgctgatt taggacatgg atttggatta gctgaagtag aattatatgg agatgtagta    540
ttaagatttg tatcttatcc tgatgaaact gatttacctt ttttacctgg atttgaaaga    600
gtatcttctc ctggagctgt agattatgga ttaactagat tgatcatgt  agtaggaaat    660 gtacctgaaa tggctcctgt aattgattat atgaaaggat ttttaggatt tcatgaattt    720
gctgaattta ctgctgaaga tgtaggaact actgaatctg gattaaattc tgtagtatta    780
gctaataatt ctgaagctgt attattacct ttaaatgaac tgtacatgg  aactaaaaga    840 agatctcaaa ttcaaactta tttagaatat catggaggac tggagtagc  tcatattgct    900 ttagcttcta atgatgtatt aagaacttta agagaaatga gagctagaac tcctatggga    960
ggatttgaat ttatggctcc tcctcaagct aaatattatg aaggagtaag aagaattgct   1020
ggagatgtat tatctgaaga acaaattaaa gaatgtcaag aattaggagt attagtagat   1080
agagatgatc aaggagtatt attacaaatt tttactaaac ctgtaggaga tagacctact   1140
```

```
tttttttag aaatgattca aagaattgga tgtatggaaa aagatgaagt aggacaagaa     1200
tatcaaaaag gaggatgtgg aggatttgga aaaggaaatt tttctgaatt atttaaatct     1260
attgaagatt atgaaaaatc tttagaagta aaacaatctg tagtagctca aaaatct        1317
```

<210> SEQ ID NO 3
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 3

```
atgcctccta ctcctgctac tgctactgga gctgctgctg ctgctgtaac tcctgaacat      60
gctgctagat cttttcctag agtagtaaga gtaaatccta gatctgatag atttcctgta     120
ttatcttttc atcatgtaga attatggtgt gctgatgctg cttctgctgc tggaagattt     180
tcttttgctt taggagctcc tttagctgct agatctgatt tatctactgg aaattctgct     240
catgcttctt tattattaag atctggagct ttagcttttt tatttactgc tccttatgct     300
cctcctcctc aagaagctgc tactgctgct actgcttcta ttccttcttt ttctgctgat     360
gctgctagaa cttttgctgc tgctcatgga ttagctgtaa gatctgtagg agtaagagta     420
gctgatgctg ctgaagcttt tagagtatct gtagctggag gagctagacc tgcttttgct     480
cctgctgatt taggacatgg atttggatta gctgaagtag aattatatgg agatgtagta     540
ttaagatttg tatcttatcc tgatgaaact gatttacctt ttttacctgg atttgaaaga     600
gtatcttctc ctggagctgt agattatgga ttaactagat tgatcatgt agtaggaaat     660 gtacctgaaa tggctcctgt aattgattat atgaaaggat tttaggatt tcatgaattt     720 gctgaattta ctgctgaaga tgtaggaact actgaatctg gattaaattc tgtagtatta     780
gctaataatt ctgaagctgt attattacct ttaaatgaac ctgtacatgg aactaaaaga     840
agatctcaaa ttcaaactta tttagaatat catggaggac tggagtagg acatattgct     900 ttagcttcta atgatgtatt aagaactta agagaaatga gagctagaac tcctatggga     960
ggatttgaat ttatggctcc tcctcaagct aaatattatg aaggagtaag aagaattgct    1020
ggagatgtat atctgaaga acaaattaaa gaatgtcaag aattaggagt attagtagat    1080
agagatgatc aaggagtatt attacaaatt tttactaaac ctgtaggaga tagacctact    1140 tttttttag aaatgattca aagaattgga tgtatggaaa aagatgaagt aggacaagaa    1200
tatcaaaaag gaggatgtgg aggatttgga aaaggaaatt tttctgaatt atttaaatct    1260
attgaagatt atgaaaaatc tttagaagta aaacaatctg tagtagctca aaaatct       1317
```

<210> SEQ ID NO 4
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 4

```
atgcctccta ctcctgctac tgctactgga gctgctgctg ctgctgtaac tcctgaacat      60
gctgctagat cttttcctag agtagtaaga gtaaatccta gatctgatag atttcctgta     120
ttatcttttc atcatgtaga attatggtgt gctgatgctg cttctgctgc tggaagattt     180
```

```
tcttttgctt taggagctcc tttagctgct agatctgatt tatctactgg aaattctgct      240
catgcttctt tattattaag atctggagct ttagcttttt tatttactgc tccttatgct      300
cctcctcctc aagaagctgc tactgctgct actgcttcta ttccttcttt ttctgctgat      360
gctgctagaa cttttgctgc tgctcatgga ttagctgtaa gatctgtagg agtaagagta      420
gctgatgctg ctgaagcttt tagagtatct gtagctggag gagctagacc tgcttttgct      480
cctgctgatt taggacatgg atttggatta gctgaagtag aattatatgg agatgtagta      540
ttaagatttg tatcttatcc tgatgaaact gatttacctt ttttacctgg atttgaaaga      600
gtatcttctc ctggagctgt agattatgga ttaactagat tgatcatgt agtaggaaat       660 gtacctgaaa tggctcctgt aattgattat atgaaaggat ttttaggatt tcatgaattt      720
gctgaattta ctgctgaaga tgtaggaact actgaatctg gattaaattc tgtagtatta      780
gctaataatt ctgaagctgt attattacct ttaaatgaac ctgtacatgg aactaaaaga      840
agatctcaaa ttcaaactta tttagaatat catggaggac ctggagtatc tcatattgct      900
ttagcttcta atgatgtatt aagaacttta agagaaatga gagctagaac tcctatggga      960
ggatttgaat ttatggctcc tcctcaagct aaatattatg aaggagtaag aagaattgct     1020
ggagatgtat tatctgaaga acaaattaaa gaatgtcaag aattaggagt attagtagat     1080
agagatgatc aaggagtatt attacaaatt tttactaaac ctgtaggaga tagacctact     1140 tttttttag aaatgattca aagaattgga tgtatggaaa aagatgaagt aggacaagaa      1200
tatcaaaaag gaggatgtgg aggatttgga aaaggaaatt tttctgaatt atttaaatct     1260
attgaagatt atgaaaaatc tttagaagta aaacaatctg tagtagctca aaaatct       1317

<210> SEQ ID NO 5
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 5
atgcctccta ctcctgctac tgctactgga gctgctgctg ctgctgtaac tcctgaacat       60
gctgctagat cttttcctag agtagtaaga gtaaatccta gatctgatag atttcctgta      120
ttatcttttc atcatgtaga attatggtgt gctgatgctg cttctgctgc tggaagattt      180
tcttttgctt taggagctcc tttagctgct agatctgatt tatctactgg aaattctgct      240
catgcttctt tattattaag atctggagct ttagcttttt tatttactgc tccttatgct      300
cctcctcctc aagaagctgc tactgctgct actgcttcta ttccttcttt ttctgctgat      360
gctgctagaa cttttgctgc tgctcatgga ttagctgtaa gatctgtagg agtaagagta      420
gctgatgctg ctgaagcttt tagagtatct gtagctggag gagctagacc tgcttttgct      480
cctgctgatt taggacatgg atttggatta gctgaagtag aattatatgg agatgtagta      540
ttaagatttg tatcttatcc tgatgaaact gatttacctt ttttacctgg atttgaaaga      600
gtatcttctc ctggagctgt agattatgga ttaactagat tgatcatgt agtaggaaat       660 gtacctgaaa tggctcctgt aattgattat atgaaaggat ttttaggatt tcatgaattt      720
gctgaattta ctgctgaaga tgtaggaact actgaatctg gattaaattc tgtagtatta      780
gctaataatt ctgaagctgt attattacct ttaaatgaac ctgtacatgg aactaaaaga      840
agatctcaaa ctcaaactta tttagaatat catggaggac ctggagtaca acatattgct      900
```

```
ttagcttcta atgatgtatt aagaacttta agagaaatga gagctagaac tcctatggga      960
ggatttgaat ttatggctcc tcctcaagct aaatattatg aaggagtaag aagaattgct     1020
ggagatgtat tatctgaaga acaaattaaa gaatgtcaag aattaggagt attagtagat     1080
agagatgatc aaggagtatt attacaaatt tttactaaac ctgtaggaga tagacctact     1140 tttttttag aaatgattca agaattgga tgtatggaaa aagatgaagt aggacaagaa       1200
tatcaaaaag gaggatgtgg aggatttgga aaggaaatt tttctgaatt atttaaatct      1260
attgaagatt atgaaaaatc tttagaagta aaacaatctg tagtagctca aaaatct        1317

<210> SEQ ID NO 6
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 6
atgcctccta ctcctgctac tgctactgga gctgctgctg ctgctgtaac tcctgaacat       60
gctgctagat cttttcctag agtagtaaga gtaaatccta gatctgatag atttcctgta      120
ttatcttttc atcatgtaga attatggtgt gctgatgctg cttctgctgc tggaagattt      180
tcttttgctt taggagctcc tttagctgct agatctgatt tatctactgg aaattctgct      240
catgcttctt tattattaag atctggagct ttagcttttt tatttactgc tccttatgct      300
cctcctcctc aagaagctgc tactgctgct actgcttcta ttccttcttt ttctgctgat      360
gctgctagaa cttttgctgc tgctcatgga ttagctgtaa gatctgtagg agtaagagta      420
gctgatgctg ctgaagcttt tagagtatct gtagctggag gagctagacc tgcttttgct      480
cctgctgatt taggacatgg atttggatta gctgaagtag aattatatgg agatgtagta      540
ttaagatttg tatcttatcc tgatgaaact gatttacctt ttttacctgg atttgaaaga      600
gtatcttctc ctggagctgt agattatgga ttaactagat ttgatcatgt agtaggaaat      660
gtacctgaaa tggctcctgt aattgattat atgaaaggat ttttaggatt tcatgaattt      720
gctgaattta ctgctgaaga gtaggaact actgaatctg gattaaattc tgtagtatta      780
gctaataatt ctgaagctgt attattacct ttaaatgaac tgtacatgg aactaaaaga      840 agatctcaag ctcaaactta tttagaatat catggaggac ctggagtaca acatattgct      900
ttagcttcta atgatgtatt aagaacttta agagaaatga gagctagaac tcctatggga      960
ggatttgaat ttatggctcc tcctcaagct aaatattatg aaggagtaag aagaattgct     1020
ggagatgtat tatctgaaga acaaattaaa gaatgtcaag aattaggagt attagtagat     1080
agagatgatc aaggagtatt attacaaatt tttactaaac ctgtaggaga tagacctact     1140 tttttttag aaatgattca agaattgga tgtatggaaa aagatgaagt aggacaagaa       1200
tatcaaaaag gaggatgtgg aggatttgga aaggaaatt tttctgaatt atttaaatct      1260
attgaagatt atgaaaaatc tttagaagta aaacaatctg tagtagctca aaaatct        1317

<210> SEQ ID NO 7
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 7
```

```
atgcctccta ctcctgctac tgctactgga gctgctgctg ctgctgtaac tcctgaacat    60
gctgctagat cttttcctag agtagtaaga gtaaatccta gatctgatag atttcctgta   120
ttatcttttc atcatgtaga attatggtgt gctgatgctg cttctgctgc tggaagattt   180
tcttttgctt taggagctcc tttagctgct agatctgatt tatctactgg aaattctgct   240
catgcttctt tattattaag atctggagct ttagcttttt tatttactgc tccttatgct   300
cctcctcctc aagaagctgc tactgctgct actgcttcta ttccttcttt ttctgctgat   360
gctgctagaa cttttgctgc tgctcatgga ttagctgtaa gatctgtagg agtaagagta   420
gctgatgctg ctgaagcttt tagagtatct gtagctggag gagctagacc tgcttttgct   480
cctgctgatt taggacatgg atttggatta gctgaagtag aattatatgg agatgtagta   540
ttaagatttg tatcttatcc tgatgaaact gatttacctt ttttacctgg atttgaaaga   600
gtatcttctc ctggagctgt agattatgga ttaactagat ttgatcatgt agtaggaaat   660
gtacctgaaa tggctcctgt aattgattat atgaaaggat ttttaggatt tcatgaattt   720
gctgaattta ctgctgaaga tgtaggaact actgaatctg gattaaattc tgtagtatta   780
gctaataatt ctgaagctgt attattacct ttaaatgaac ctgtacatgg aactaaaaga   840
agatctcaat ctcaaactta tttagaatat catggaggac ctggagtaca acatattgct   900
ttagcttcta atgatgtatt aagaacttta agagaaatga gagctagaac tcctatggga   960
ggatttgaat ttatggctcc tcctcaagct aaatattatg aaggagtaag aagaattgct  1020
ggagatgtat tatctgaaga acaaattaaa gaatgtcaag aattaggagt attagtagat  1080
agagatgatc aaggagtatt attacaaatt tttactaaac ctgtaggaga tagacctact  1140
tttttttag aaatgattca agaattgga tgtatggaaa aagatgaagt aggacaagaa   1200
tatcaaaaag gaggatgtgg aggatttgga aaaggaaatt tttctgaatt atttaaatct  1260
attgaagatt atgaaaaatc tttagaagta aaacaatctg tagtagctca aaaatct     1317
```

<210> SEQ ID NO 8
<211> LENGTH: 1317
<212> TYPE: DNA
<213> ORGANISM: Artificial Sequence
<220> FEATURE:
<223> OTHER INFORMATION: nucleotide sequence encoding mutant HPPD
   polypeptide

<400> SEQUENCE: 8

```
atgcctccta ctcctgctac tgctactgga gctgctgctg ctgctgtaac tcctgaacat    60
gctgctagat cttttcctag agtagtaaga gtaaatccta gatctgatag atttcctgta   120
ttatcttttc atcatgtaga attatggtgt gctgatgctg cttctgctgc tggaagattt   180
tcttttgctt taggagctcc tttagctgct agatctgatt tatctactgg aaattctgct   240
catgcttctt tattattaag atctggagct ttagcttttt tatttactgc tccttatgct   300
cctcctcctc aagaagctgc tactgctgct actgcttcta ttccttcttt ttctgctgat   360
gctgctagaa cttttgctgc tgctcatgga ttagctgtaa gatctgtagg agtaagagta   420
gctgatgctg ctgaagcttt tagagtatct gtagctggag gagctagacc tgcttttgct   480
cctgctgatt taggacatgg atttggatta gctgaagtag aattatatgg agatgtagta   540
ttaagatttg tatcttatcc tgatgaaact gatttacctt ttttacctgg atttgaaaga   600
gtatcttctc ctggagctgt agattatgga ttaactagat ttgatcatgt agtaggaaat   660
gtacctgaaa tggctcctgt aattgattat atgaaaggat ttttaggatt tcatgaattt   720
```

```
gctgaattta ctgctgaaga tgtaggaact actgaatctg gattaaattc tgtagtatta    780
gctaataatt ctgaagctgt attattacct ttaaatgaac ctgtacatgg aactaaaaga    840
agatctcaag tacaaactta tttagaatat catggaggac ctggagtaca acatattgct    900
ttagcttcta atgatgtatt aagaacttta agagaaatga gagctagaac tcctatggga    960
ggatttgaat ttatggctcc tcctcaagct aaatattatg aaggagtaag aagaattgct   1020
ggagatgtat tatctgaaga acaaattaaa gaatgtcaag aattaggagt attagtagat   1080
agagatgatc aaggagtatt attacaaatt tttactaaac ctgtaggaga tagacctact   1140
ttttttttag aaatgattca agaattgga tgtatggaaa aagatgaagt aggacaagaa    1200
tatcaaaaag gaggatgtgg aggatttgga aaggaaatt tttctgaatt atttaaatct    1260
attgaagatt atgaaaaatc tttagaagta aaacaatctg tagtagctca aaaatct     1317

<210> SEQ ID NO 9
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 9
atgcctccta ctcctgctac tgctactgga gctgctgctg ctgctgtaac tcctgaacat     60
gctgctagat cttttcctag agtagtaaga gtaaatccta gatctgatag atttcctgta    120
ttatcttttc atcatgtaga attatggtgt gctgatgctg cttctgctgc tggaagattt    180
tcttttgctt taggagctcc tttagctgct agatctgatt tatctactgg aaattctgct    240
catgcttctt tattattaag atctggagct ttagcttttt tatttactgc tccttatgct    300
cctcctcctc aagaagctgc tactgctgct actgcttcta ttccttcttt ttctgctgat    360
gctgctagaa cttttgctgc tgctcatgga ttagctgtaa gatctgtagg agtaagagta    420
gctgatgctg ctgaagcttt tagagtatct gtagctggag gagctagacc tgcttttgct    480
cctgctgatt taggacatgg atttggatta gctgaagtag aattatatgg agatgtagta    540
ttaagatttg tatcttatcc tgatgaaact gatttacctt ttttacctgg atttgaaaga    600
gtatcttctc ctggagctgt agattatgga ttaactagat tgatcatgt agtaggaaat    660 gtacctgaaa tggctcctgt aattgattat atgaaaggat ttttaggatt tcatgaattt    720
gctgaattta ctgctgaaga tgtaggaact actgaatctg gaatgaattc tgtagtatta    780
gctaataatt ctgaagctgt attattacct ttaaatgaac ctgtacatgg aactaaaaga    840
agatctcaaa ttcaaactta tttagaatat catggaggac ctggagtaca acatattgct    900
ttagcttcta atgatgtatt aagaacttta agagaaatga gagctagaac tcctatggga    960
ggatttgaat ttatggctcc tcctcaagct aaatattatg aaggagtaag aagaattgct   1020
ggagatgtat tatctgaaga acaaattaaa gaatgtcaag aattaggagt attagtagat   1080
agagatgatc aaggagtatt attacaaatt tttactaaac ctgtaggaga tagacctact   1140
ttttttttag aaatgattca agaattgga tgtatggaaa aagatgaagt aggacaagaa    1200
tatcaaaaag gaggatgtgg aggatttgga aaggaaatt tttctgaatt atttaaatct    1260
attgaagatt atgaaaaatc tttagaagta aaacaatctg tagtagctca aaaatct     1317

<210> SEQ ID NO 10
<211> LENGTH: 1317
```

```
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 10
atgcctccta ctcctgctac tgctactgga gctgctgctg ctgctgtaac tcctgaacat    60
gctgctagat cttttcctag agtagtaaga gtaaatccta gatctgatag atttcctgta   120
ttatcttttc atcatgtaga attatggtgt gctgatgctg cttctgctgc tggaagattt   180
tcttttgctt taggagctcc tttagctgct agatctgatt tatctactgg aaattctgct   240
catgcttctt tattattaag atctggagct ttagcttttt tatttactgc tccttatgct   300
cctcctcctc aagaagctgc tactgctgct actgcttcta ttccttcttt ttctgctgat   360
gctgctagaa cttttgctgc tgctcatgga ttagctgtaa gatctgtagg agtaagagta   420
gctgatgctg ctgaagcttt tagagtatct gtagctggag gagctagacc tgcttttgct   480
cctgctgatt taggacatgg atttggatta gctgaagtag aattatatgg agatgtagta   540
ttaagatttg tatcttatcc tgatgaaact gatttacctt ttttacctgg atttgaaaga   600
gtatcttctc ctggagctgt agattatgga ttaactagat ttgatcatgt agtaggaaat   660
gtacctgaaa tggctcctgt aattgattat atgaaaggat tttaggatt tcatgaattt   720 tgggaattta ctgctgaaga tgtaggaact actgaatctg gattaaattc tgtagtatta   780
gctaataatt ctgaagctgt attattacct ttaaatgaac tgtacatgga actaaaaga   840 agatctcaaa ttcaaactta tttagaatat catggaggac tggagtaca acatattgct   900 ttagcttcta tgatgtatt aagaacttta agagaaatga gagctagaac tcctatggga   960
ggatttgaat ttatggctcc tcctcaagct aaatattatg aaggagtaag aagaattgct  1020
ggagatgtat atctgaaga acaaattaaa gaatgtcaag aattaggagt attagtagat  1080
agagatgatc aaggagtatt attacaaatt tttactaaac ctgtaggaga tagacctact  1140
ttttttttag aaatgattca agaattgga tgtatggaaa aagatgaagt aggacaagaa  1200
tatcaaaaag gaggatgtgg aggatttgga aaaggaaatt tttctgaatt atttaaatct  1260
attgaagatt atgaaaaatc tttagaagta aaacaatctg tagtagctca aaaatct    1317

<210> SEQ ID NO 11
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 11
atgcctccta ctcctgctac tgctactgga gctgctgctg ctgctgtaac tcctgaacat    60
gctgctagat cttttcctag agtagtaaga gtaaatccta gatctgatag atttcctgta   120
ttatcttttc atcatgtaga attatggtgt gctgatgctg cttctgctgc tggaagattt   180
tcttttgctt taggagctcc tttagctgct agatctgatt tatctactgg aaattctgct   240
catgcttctt tattattaag atctggagct ttagcttttt tatttactgc tccttatgct   300
cctcctcctc aagaagctgc tactgctgct actgcttcta ttccttcttt ttctgctgat   360
gctgctagaa cttttgctgc tgctcatgga ttagctgtaa gatctgtagg agtaagagta   420
gctgatgctg ctgaagcttt tagagtatct gtagctggag gagctagacc tgcttttgct   480
```

| | |
|---|---:|
| cctgctgatt taggacatgg atttggatta gctgaagtag aattatatgg agatgtagta | 540 |
| ttaagatttg tatcttatcc tgatgaaact gatttacctt ttttacctgg atttgaaaga | 600 |
| gtatcttctc ctggagctgt agattatgga ttaactagat ttgatcatgt agtaggaaat | 660 |
| gtacctgaaa tggctcctgt aattgattat atgaaaggat ttttaggatt tcatgaattt | 720 |
| gctgaattta ctgctgaaga tgtaggaact actgaatctg gattaaattc tgtagtatta | 780 |
| gctaataatt ctgaagctgt attattacct ttaaatgaac ctgtacatgg aactaaaaga | 840 |
| agatctcaaa ttcaaactta tttagaatat catggaggac ctggagtaca acatattgct | 900 |
| ttagcttcta atgatgtatt aagaacttta agagaaatga gagctagaac tcctatggga | 960 |
| ggatttgaat ttatggctcc tcctcaagct aaatattatg aaggagtaag aagaattgct | 1020 |
| ggagatgtat tatctgaaga acaaattaaa gaatgtcaag aattaggagt aatggtagat | 1080 |
| agagatgatc aaggagtatt attacaaatt tttactaaac ctgtaggaga tagacctact | 1140 |
| ttttttttag aaatgattca aagaattgga tgtatggaaa aagatgaagt aggacaagaa | 1200 |
| tatcaaaaag gaggatgtgg aggatttgga aaggaaatt tttctgaatt atttaaatct | 1260 |
| attgaagatt atgaaaaatc tttagaagta aaacaatctg tagtagctca aaaatct | 1317 |

<210> SEQ ID NO 12
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 12

| | |
|---|---:|
| atgcctccta ctcctgctac tgctactgga gctgctgctg ctgctgtaac tcctgaacat | 60 |
| gctgctagat cttttcctag agtagtaaga gtaaatccta gatctgatag atttcctgta | 120 |
| ttatcttttc atcatgtaga attatggtgt gctgatgctg cttctgctgc tggaagattt | 180 |
| tcttttgctt taggagctcc tttagctgct agatctgatt tatctactgg aaattctgct | 240 |
| catgcttctt tattattaag atctggagct ttagcttttt tatttactgc tccttatgct | 300 |
| cctcctcctc aagaagctgc tactgctgct actgcttcta ttccttcttt ttctgctgat | 360 |
| gctgctagaa cttttgctgc tgctcatgga ttagctgtaa gatctgtagg agtaagagta | 420 |
| gctgatgctg ctgaagcttt tagagtatct gtagctggag agctagacc tgcttttgct | 480 |
| cctgctgatt taggacatgg atttggatta gctgaagtag aattatatgg agatgtagta | 540 |
| ttaagatttg tatcttatcc tgatgaaact gatttacctt ttttacctgg atttgaaaga | 600 |
| gtatcttctc ctggagctgt agattatgga ttaactagat ttgatcatgt agtaggaaat | 660 |
| gtacctgaaa tggctcctgt aattgattat atgaaaggat ttttaggatt tcatgaattt | 720 |
| gctgaattta ctgctgaaga tgtaggaact actgaatctg gattaaattc tgtagtatta | 780 |
| gctaataatt ctgaagctgt attattacct ttaaatgaac ctgtacatgg aactaaaaga | 840 |
| agatctcaaa ttcaaactta tttagaatat catggaggac ctggagtaca acatattgct | 900 |
| ttagcttcta atgatgtatt aagaacttta agagaaatga gagctagaac tcctatggga | 960 |
| ggatttgaat ttatggctcc tcctcaagct aaatattatg aaggagtaag aagaattgct | 1020 |
| ggagatgtat tatctgaaga acaaattaaa gaatgtcaag aattaggagt agctgtagat | 1080 |
| agagatgatc aaggagtatt attacaaatt tttactaaac ctgtaggaga tagacctact | 1140 |
| ttttttttag aaatgattca aagaattgga tgtatggaaa aagatgaagt aggacaagaa | 1200 |

```
tatcaaaaag gaggatgtgg aggatttgga aaaggaaatt tttctgaatt atttaaatct    1260
attgaagatt atgaaaaatc tttagaagta aaacaatctg tagtagctca aaaatct       1317
```

<210> SEQ ID NO 13
<211> LENGTH: 1317
<212> TYPE: DNA
<213> ORGANISM: Artificial Sequence
<220> FEATURE:
<223> OTHER INFORMATION: nucleotide sequence encoding mutant HPPD
      polypeptide

<400> SEQUENCE: 13

```
atgcctccta ctcctgctac tgctactgga gctgctgctg ctgctgtaac tcctgaacat     60
gctgctagat cttttcctag agtagtaaga gtaaatccta gatctgatag atttcctgta    120
ttatcttttc atcatgtaga attatggtgt gctgatgctg cttctgctgc tggaagattt    180
tcttttgctt taggagctcc tttagctgct agatctgatt tatctactgg aaattctgct    240
catgcttctt tattattaag atctggagct ttagcttttt tatttactgc tccttatgct    300
cctcctcctc aagaagctgc tactgctgct actgcttcta ttccttcttt ttctgctgat    360
gctgctagaa cttttgctgc tgctcatgga ttagctgtaa gatctgtagg agtaagagta    420
gctgatgctg ctgaagcttt tagagtatct gtagctggag gagctagacc tgcttttgct    480
cctgctgatt aggacatgg atttggatta gctgaagtag aattatatgg agatgtagta    540
ttaagatttg tatcttatcc tgatgaaact gatttacctt ttttacctgg atttgaaaga    600
gtatcttctc ctggagctgt agattatgga ttaactagat tgatcatgt agtaggaaat    660 gtacctgaaa tggctcctgt aattgattat atgaaaggat ttttaggatt tcatgaattt    720
gctgaattta ctgctgaaga gtaggaact actgaatctg gaatgaattc tgtagtatta    780
gctaataatt ctgaagctgt attattacct ttaaatgaac tgtacatgg aactaaaaga    840 agatctcaaa ttcaaactta tttagaatat catggaggac tggagtaca acatattgct    900 ttagcttcta atgatgtatt aagaacttta agagaaatga gagctagaac tcctatggga    960
ggatttgaat ttatggctcc tcctcaagct aaatattatg aaggagtaag aagaattgct   1020
ggagatgtat tatctgaaga acaaattaaa gaatgtcaag aattaggagt aatggtagat   1080
agagatgatc aaggagtatt attacaaatt tttactaaac ctgtaggaga tagacctact   1140 tttttttttag aaatgattca agaattgga tgtatgaaa agatgaagt aggacaagaa    1200 tatcaaaaag gaggatgtgg aggatttgga aaaggaaatt tttctgaatt atttaaatct   1260
attgaagatt atgaaaaatc tttagaagta aaacaatctg tagtagctca aaaatct      1317
```

<210> SEQ ID NO 14
<211> LENGTH: 439
<212> TYPE: PRT
<213> ORGANISM: Artificial Sequence
<220> FEATURE:
<223> OTHER INFORMATION: mutant HPPD polypeptide

<400> SEQUENCE: 14

```
Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
```

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
                180                 185                 190

Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
370                 375                 380

Met Ile Gln Arg Ile Gly Cys Met Glu Lys Asp Val Gly Gln Glu
385                 390                 395                 400

Tyr Gln Lys Gly Gly Cys Gly Phe Gly Lys Gly Asn Phe Ser Glu
            405                 410                 415

Leu Phe Lys Ser Ile Glu Asp Tyr Glu Lys Ser Leu Glu Val Lys Gln
            420                 425                 430

Ser Val Val Ala Gln Lys Ser

<210> SEQ ID NO 15
<211> LENGTH: 439
<212> TYPE: PRT
<213> ORGANISM: Avena sativa

```
<400> SEQUENCE: 15

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Ala His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415
```

```
Leu Phe Lys Ser Ile Glu Asp Tyr Glu Lys Ser Leu Glu Val Lys Gln
                420                 425                 430

Ser Val Ala Gln Lys Ser
        435

<210> SEQ ID NO 16
<211> LENGTH: 439
<212> TYPE: PRT
<213> ORGANISM: Avena sativa

<400> SEQUENCE: 16

Met Pro Pro Thr Pro Ala Thr Ala Thr Gly Ala Ala Ala Ala Ala Val
  1               5                  10                  15

Thr Pro Glu His Ala Ala Arg Ser Phe Pro Arg Val Val Arg Val Asn
               20                  25                  30

Pro Arg Ser Asp Arg Phe Pro Val Leu Ser Phe His His Val Glu Leu
           35                  40                  45

Trp Cys Ala Asp Ala Ala Ser Ala Ala Gly Arg Phe Ser Phe Ala Leu
     50                  55                  60

Gly Ala Pro Leu Ala Ala Arg Ser Asp Leu Ser Thr Gly Asn Ser Ala
 65                  70                  75                  80

His Ala Ser Leu Leu Leu Arg Ser Gly Ala Leu Ala Phe Leu Phe Thr
                 85                  90                  95

Ala Pro Tyr Ala Pro Pro Gln Glu Ala Ala Thr Ala Ala Thr Ala
                100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gly His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
```

```
                    340                 345                 350
Gln Glu Leu Gly Val Leu Val Asp Arg Asp Gln Gly Val Leu Leu
                355                 360                 365
Gln Ile Phe Thr Lys Pro Val Gly Asp Arg Pro Thr Phe Leu Glu
            370                 375                 380
Met Ile Gln Arg Ile Gly Cys Met Glu Lys Asp Glu Val Gly Gln Glu
385                 390                 395                 400
Tyr Gln Lys Gly Gly Cys Gly Gly Phe Gly Lys Gly Asn Phe Ser Glu
                405                 410                 415
Leu Phe Lys Ser Ile Glu Asp Tyr Glu Lys Ser Leu Glu Val Lys Gln
                420                 425                 430
Ser Val Val Ala Gln Lys Ser
                435

<210> SEQ ID NO 17
<211> LENGTH: 439
<212> TYPE: PRT
<213> ORGANISM: Avena sativa

<400> SEQUENCE: 17

Met Pro Pro Thr Pro Ala Thr Ala Thr Gly Ala Ala Ala Ala Val
1               5                   10                  15
Thr Pro Glu His Ala Ala Arg Ser Phe Pro Arg Val Val Arg Val Asn
                20                  25                  30
Pro Arg Ser Asp Arg Phe Pro Val Leu Ser Phe His His Val Glu Leu
                35                  40                  45
Trp Cys Ala Asp Ala Ala Ser Ala Ala Gly Arg Phe Ser Phe Ala Leu
    50                  55                  60
Gly Ala Pro Leu Ala Ala Arg Ser Asp Leu Ser Thr Gly Asn Ser Ala
65                  70                  75                  80
His Ala Ser Leu Leu Leu Arg Ser Gly Ala Leu Ala Phe Leu Phe Thr
                85                  90                  95
Ala Pro Tyr Ala Pro Pro Gln Glu Ala Ala Thr Ala Ala Thr Ala
                100                 105                 110
Ser Ile Pro Ser Phe Ser Ala Asp Ala Ala Arg Thr Phe Ala Ala Ala
                115                 120                 125
His Gly Leu Ala Val Arg Ser Val Gly Val Arg Val Ala Asp Ala Ala
                130                 135                 140
Glu Ala Phe Arg Val Ser Val Ala Gly Gly Ala Arg Pro Ala Phe Ala
145                 150                 155                 160
Pro Ala Asp Leu Gly His Gly Phe Gly Leu Ala Glu Val Glu Leu Tyr
                165                 170                 175
Gly Asp Val Val Leu Arg Phe Val Ser Tyr Pro Asp Glu Thr Asp Leu
                180                 185                 190
Pro Phe Leu Pro Gly Phe Glu Arg Val Ser Ser Pro Gly Ala Val Asp
                195                 200                 205
Tyr Gly Leu Thr Arg Phe Asp His Val Val Gly Asn Val Pro Glu Met
                210                 215                 220
Ala Pro Val Ile Asp Tyr Met Lys Gly Phe Leu Gly Phe His Glu Phe
225                 230                 235                 240
Ala Glu Phe Thr Ala Glu Asp Val Gly Thr Thr Glu Ser Gly Leu Asn
                245                 250                 255
Ser Val Val Leu Ala Asn Asn Ser Glu Ala Val Leu Leu Pro Leu Asn
                260                 265                 270
```

```
Glu Pro Val His Gly Thr Lys Arg Arg Ser Gln Ile Gln Thr Tyr Leu
            275                 280                 285

Glu Tyr His Gly Gly Pro Gly Val Ser His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                    325                 330                 335

Arg Arg Ile Ala Gly Asp Val Leu Ser Glu Glu Ile Lys Glu Cys
                340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                    405                 410                 415

Leu Phe Lys Ser Ile Glu Asp Tyr Glu Lys Ser Leu Glu Val Lys Gln
                420                 425                 430

Ser Val Val Ala Gln Lys Ser
            435

<210> SEQ ID NO 18
<211> LENGTH: 439
<212> TYPE: PRT
<213> ORGANISM: Avena sativa

<400> SEQUENCE: 18

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Thr Ala Ala Thr Ala
                100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                    165                 170                 175

Gly Asp Val Val Leu Arg Phe Val Ser Tyr Pro Asp Glu Thr Asp Leu
                180                 185                 190

Pro Phe Leu Pro Gly Phe Glu Arg Val Ser Ser Pro Gly Ala Val Asp
            195                 200                 205
```

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
                260                 265                 270

Glu Pro Val His Gly Thr Lys Arg Arg Ser Gln Thr Gln Thr Tyr Leu
            275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 19
<211> LENGTH: 439
<212> TYPE: PRT
<213> ORGANISM: Avena sativa

<400> SEQUENCE: 19

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
                100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala

```
            130                 135                 140
Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ala Gln Thr Tyr Leu
        275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 20
<211> LENGTH: 439
<212> TYPE: PRT
<213> ORGANISM: Avena sativa

<400> SEQUENCE: 20

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60
```

```
Gly Ala Pro Leu Ala Ala Arg Ser Asp Leu Ser Thr Gly Asn Ser Ala
 65                  70                  75                  80

His Ala Ser Leu Leu Arg Ser Gly Ala Leu Ala Phe Leu Phe Thr
                 85                  90                  95

Ala Pro Tyr Ala Pro Pro Gln Glu Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
                180                 185                 190

Pro Phe Leu Pro Gly Phe Glu Arg Val Ser Ser Pro Gly Ala Val Asp
                195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Leu Ala Asn Asn Ser Glu Ala Val Leu Leu Pro Leu Asn
            260                 265                 270

Glu Pro Val His Gly Thr Lys Arg Arg Ser Gln Ser Gln Thr Tyr Leu
                275                 280                 285

Glu Tyr His Gly Gly Pro Gly Val Gln His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435
```

<210> SEQ ID NO 21
<211> LENGTH: 439
<212> TYPE: PRT
<213> ORGANISM: Avena sativa

<400> SEQUENCE: 21

-continued

```
Met Pro Pro Thr Pro Ala Thr Ala Thr Gly Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
                115                 120                 125

His Gly Leu Ala Val Arg Ser Val Gly Val Arg Val Ala Asp Ala Ala
            130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
            245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Val Gln Thr Tyr Leu
            275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
            325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415
```

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 22
<211> LENGTH: 439
<212> TYPE: PRT
<213> ORGANISM: Avena sativa

<400> SEQUENCE: 22

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Met Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

```
Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
        370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 23
<211> LENGTH: 439
<212> TYPE: PRT
<213> ORGANISM: Avena sativa

<400> SEQUENCE: 23

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Trp Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
```

```
                275                 280                 285
Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 24
<211> LENGTH: 439
<212> TYPE: PRT
<213> ORGANISM: Avena sativa

<400> SEQUENCE: 24

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
                100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205
```

```
Tyr Gly Leu Thr Arg Phe Asp His Val Val Gly Asn Val Pro Glu Met
            210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Met Val Asp Arg Asp Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 25
<211> LENGTH: 439
<212> TYPE: PRT
<213> ORGANISM: Avena sativa

<400> SEQUENCE: 25

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140
```

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Ser Gln Ile Gln Thr Tyr Leu
    275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Gln Ile Lys Glu Cys
            340                 345                 350

Gln Glu Leu Gly Val Ala Val Asp Arg Asp Gln Gly Val Leu Leu
    355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 26
<211> LENGTH: 439
<212> TYPE: PRT
<213> ORGANISM: Avena sativa

<400> SEQUENCE: 26

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His Val Glu Leu
            35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala

His Ala Ser Leu Leu Arg Ser Gly Ala Leu Ala Phe Leu Phe Thr
 65                  70                  75                  80

Ala Pro Tyr Ala Pro Pro Gln Glu Ala Thr Ala Ala Thr Ala
             85                  90                  95

Ser Ile Pro Ser Phe Ser Ala Asp Ala Ala Arg Thr Phe Ala Ala Ala
            100                 105                 110

His Gly Leu Ala Val Arg Ser Val Gly Val Arg Val Ala Asp Ala Ala
        115                 120                 125

Glu Ala Phe Arg Val Ser Val Ala Gly Ala Arg Pro Ala Phe Ala
130                 135                 140

Pro Ala Asp Leu Gly His Gly Phe Gly Leu Ala Glu Val Glu Leu Tyr
145                 150                 155                 160

Gly Asp Val Val Leu Arg Phe Val Ser Tyr Pro Asp Glu Thr Asp Leu
        165                 170                 175

Pro Phe Leu Pro Gly Phe Glu Arg Val Ser Ser Pro Gly Ala Val Asp
            180                 185                 190

Tyr Gly Leu Thr Arg Phe Asp His Val Val Gly Asn Val Pro Glu Met
                195                 200                 205

Ala Pro Val Ile Asp Tyr Met Lys Gly Phe Leu Gly Phe His Glu Phe
210                 215                 220

Ala Glu Phe Thr Ala Glu Asp Val Gly Thr Thr Glu Ser Gly Met Asn
225                 230                 235                 240

Ser Val Val Leu Ala Asn Asn Ser Glu Ala Val Leu Leu Pro Leu Asn
        245                 250                 255

Glu Pro Val His Gly Thr Lys Arg Ser Gln Ile Gln Thr Tyr Leu
            260                 265                 270

Glu Tyr His Gly Gly Pro Gly Val Gln His Ile Ala Leu Ala Ser Asn
                275                 280                 285

Asp Val Leu Arg Thr Leu Arg Glu Met Arg Ala Arg Thr Pro Met Gly
290                 295                 300

Gly Phe Glu Phe Met Ala Pro Pro Gln Ala Lys Tyr Tyr Glu Gly Val
305                 310                 315                 320

Arg Arg Ile Ala Gly Asp Val Leu Ser Glu Glu Ile Lys Glu Cys
        325                 330                 335

Gln Glu Leu Gly Val Met Val Asp Arg Asp Gln Gly Val Leu Leu
            340                 345                 350

Gln Ile Phe Thr Lys Pro Val Gly Asp Arg Pro Thr Phe Phe Leu Glu
                355                 360                 365

Met Ile Gln Arg Ile Gly Cys Met Glu Lys Asp Glu Val Gly Gln Glu
370                 375                 380

Tyr Gln Lys Gly Gly Cys Gly Gly Phe Gly Lys Gly Asn Phe Ser Glu
385                 390                 395                 400

Leu Phe Lys Ser Ile Glu Asp Tyr Glu Lys Ser Leu Glu Val Lys Gln
        405                 410                 415

Ser Val Val Ala Gln Lys Ser
            420                 425                 430

Ser Val Val Ala Gln Lys Ser
        435

<210> SEQ ID NO 27
<211> LENGTH: 440
<212> TYPE: PRT
<213> ORGANISM: Avena sativa

<400> SEQUENCE: 27

-continued

```
Met Pro Pro Thr Pro Ala Thr Ala Thr Gly Ala Ala Ala Ala Val
 1               5                  10                 15

Thr Pro Glu His Ala Ala Arg Ser Phe Pro Arg Val Val Arg Val Asn
             20                  25                  30

Pro Arg Ser Asp Arg Phe Pro Val Leu Ser Phe His His Val Glu Leu
         35                  40                  45

Trp Cys Ala Asp Ala Ala Ser Ala Ala Gly Arg Phe Ser Phe Ala Leu
     50                  55                  60

Gly Ala Pro Leu Ala Ala Arg Ser Asp Leu Ser Thr Gly Asn Ser Ala
 65                  70                  75                  80

His Ala Ser Leu Leu Leu Arg Ser Gly Ala Leu Ala Phe Leu Phe Thr
                 85                  90                  95

Ala Pro Tyr Ala Pro Pro Gln Glu Ala Thr Ala Ala Ala Thr
                100                 105                 110

Ala Ser Ile Pro Ser Phe Ser Ala Asp Ala Ala Arg Thr Phe Ala Ala
             115                 120                 125

Ala His Gly Leu Ala Val Arg Ser Val Gly Val Arg Val Ala Asp Ala
         130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
                 165                 170                 175

Tyr Gly Asp Val Val Leu Arg Phe Val Ser Tyr Pro Asp Glu Thr Asp
             180                 185                 190

Leu Pro Phe Leu Pro Gly Phe Glu Arg Val Ser Ser Pro Gly Ala Val
         195                 200                 205

Asp Tyr Gly Leu Thr Arg Phe Asp His Val Val Gly Asn Val Pro Glu
 210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                 245                 250                 255

Asn Ser Val Val Leu Ala Asn Asn Ser Glu Ala Val Leu Leu Pro Leu
             260                 265                 270

Asn Glu Pro Val His Gly Thr Lys Arg Arg Ser Gln Ile Gln Thr Tyr
         275                 280                 285

Leu Glu Tyr His Gly Gly Pro Gly Val Gln His Ile Ala Leu Ala Ser
 290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                 325                 330                 335

Val Arg Arg Ile Ala Gly Asp Val Leu Ser Glu Glu Ile Lys Glu
             340                 345                 350

Cys Gln Glu Leu Gly Val Leu Val Asp Arg Asp Gln Gly Val Leu
         355                 360                 365

Leu Gln Ile Phe Thr Lys Pro Val Gly Asp Arg Pro Thr Phe Phe Leu
 370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                 405                 410                 415

Glu Leu Phe Lys Ser Ile Glu Asp Tyr Glu Lys Ser Leu Glu Val Lys
```

```
                420                 425                 430
Gln Ser Val Val Ala Gln Lys Ser
        435                 440

<210> SEQ ID NO 28
<211> LENGTH: 7
<212> TYPE: PRT
<213> ORGANISM: Artificial Sequence
<220> FEATURE:
<223> OTHER INFORMATION: sequence motif from Avena sativa derived HPPD
<220> FEATURE:
<221> NAME/KEY: VARIANT
<222> LOCATION: 2
<223> OTHER INFORMATION: Xaa = K, A, or R
<220> FEATURE:
<221> NAME/KEY: VARIANT
<222> LOCATION: 6
<223> OTHER INFORMATION: Xaa = Q or E

<400> SEQUENCE: 28

Arg Xaa Ser Gln Ile Xaa Thr
1               5

<210> SEQ ID NO 29
<211> LENGTH: 6
<212> TYPE: PRT
<213> ORGANISM: Artificial Sequence
<220> FEATURE:
<223> OTHER INFORMATION: sequence motif from Avena sativa derived HPPD
<220> FEATURE:
<221> NAME/KEY: VARIANT
<222> LOCATION: 1
<223> OTHER INFORMATION: Xaa = P, A, or S
<220> FEATURE:
<221> NAME/KEY: VARIANT
<222> LOCATION: 3
<223> OTHER INFORMATION: Xaa = V or L
<220> FEATURE:
<221> NAME/KEY: VARIANT
<222> LOCATION: 6
<223> OTHER INFORMATION: Xaa = I, L, or M

<400> SEQUENCE: 29

Xaa Gly Xaa Gln His Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: sequence motif from Avena sativa derived HPPD
<220> FEATURE:
<221> NAME/KEY: VARIANT
<222> LOCATION: 2
<223> OTHER INFORMATION: Xaa = I or V

<400> SEQUENCE: 30

Gly Xaa Leu Val Asp Arg Asp
1               5

<210> SEQ ID NO 31
<211> LENGTH: 6
<212> TYPE: PRT
<213> ORGANISM: Artificial Sequence
<220> FEATURE:
<223> OTHER INFORMATION: sequence motif from Avena sativa derived HPPD
<220> FEATURE:
<221> NAME/KEY: VARIANT
<222> LOCATION: 6
<223> OTHER INFORMATION: Xaa = S or G
```

<400> SEQUENCE: 31

Glu Ser Gly Leu Asn Xaa
1               5

<210> SEQ ID NO 32
<211> LENGTH: 5
<212> TYPE: PRT
<213> ORGANISM: Artificial Sequence
<220> FEATURE:
<223> OTHER INFORMATION: sequence motif from Avena sativa derived HPPD
<220> FEATURE:
<221> NAME/KEY: VARIANT
<222> LOCATION: 2
<223> OTHER INFORMATION: Xaa = A or S
<220> FEATURE:
<221> NAME/KEY: VARIANT
<222> LOCATION: 5
<223> OTHER INFORMATION: Xaa = T or V

<400> SEQUENCE: 32

Phe Xaa Glu Phe Xaa
1               5

<210> SEQ ID NO 33
<211> LENGTH: 11205
<212> TYPE: DNA
<213> ORGANISM: Artificial Sequence
<220> FEATURE:
<223> OTHER INFORMATION: vector

<400> SEQUENCE: 33

| | | | |
|---|---|---|---|
| attcctgtgg | ttggcatgca | catacaaatg gacgaacgga taaacctttt cacgcccttt | 60 |
| taaatatccg | attattctaa | taaacgctct tttctcttag gtttacccgc caatatatcc | 120 |
| tgtcaaacac | tgatagttta | aactgaaggc gggaaacgac aatctgatca tgagcggaga | 180 |
| attaagggag | tcacgttatg | accccgccg atgacgcggg acaagccgtt ttacgtttgg | 240 |
| aactgacaga | accgcaacgc | tgcaggaatt ggccgcagcg gccatttaaa tcaattgggc | 300 |
| gcgtacgtag | cactagtgaa | ttccggaccc aagcttgcat gcctgcagga attggccgca | 360 |
| gcggccattt | aaatcaattg | ggcgcgtgcg gccgcagctg cttgtgggga ccagacaaaa | 420 |
| aaggaatggt | gcagaattgt | taggcgcacc taccaaaagc atctttgcct ttattgcaaa | 480 |
| gataaagcag | attcctctag | tacaagtggg gaacaaaata acgtggaaaa gagctgtcct | 540 |
| gacagcccac | tcactaatgc | gtatgacgaa cgcagtgacg accacaaaac tcgagacttt | 600 |
| tcaacaaagg | gtaatatccg | gaaacctcct cggattccat tgcccagcta tctgtcactt | 660 |
| tattgtgaag | atagtggaaa | aggaaggtgg ctcctacaaa tgccatcatt gcgataaagg | 720 |
| aaaggctatc | gttgaagatg | cctctgccga cagtggtccc aaagatggac ccccacccac | 780 |
| gaggagcatc | gtggaaaaag | aagacgttcc aaccacgtct tcaaagcaag tggattgatg | 840 |
| tgatatctcc | actgacgtaa | gggatgacga acaatcccac tatccttctg caggtcgact | 900 |
| ctagaggatc | ctataaatag | gaagttcatt tcatttggag aggaaacctc gagtattttt | 960 |
| acaacaatta | ccaacaacaa | caacaacaa acaacattac aattactatt tacaattaca | 1020 |
| catatgcctc | caacaccagc | tactgctact ggagctgctg ctgctgccgt tacaccagaa | 1080 |
| catgctgcaa | ggtcattccc | tagagttgtt cgcgttaacc ctaggtctga cagattccct | 1140 |
| gttctgtcct | tccatcatgt | ggagcttggg tgtgctgatg cagctagtgc tgctggtcgt | 1200 |
| ttcagctttg | cacttggagc | accacttgct gcaagatctg atctgtctac agggaactca | 1260 |

```
gcacatgctt ctctcctact tcgatctgga gcattagcct tccttttac  cgctccttat   1320
gctccacctc cacaagaagc tgcaactgct gcaactgctt ccattccctc cttttcagca   1380
gatgctgcaa gaacctttgc tgctgcacat ggacttgctg tcagatctgt tggagttagg   1440
gttgctgatg cagctgaagc atttcgcgtt agtgttgctg gaggagcaag acctgctttt   1500
gctccagcag atcttggtca cggatttgga cttgctgaag tggagctgta tggagatgtg   1560
gttctgagat tcgtgagcta tcctgacgaa actgacctac catttctccc aggattcgag   1620
agggtttcaa gtccaggtgc agttgactac ggtttgactc gctttgacca cgttgttgga   1680
aacgttccag aaatggctcc tgtcatcgac tacatgaagg gattccttgg tttccacgag   1740
ttcgctgaat tcacagcaga ggatgttgga accacagaat ctggactgaa cagtgtggtt   1800
ctagccaaca cagtgaagc  tgttcttctg ccattgaacg agcctgttca tggaaccaag   1860
agacgatctc agatccaaac ctacctcgaa taccatggtg gaccaggagt tcaacacatc   1920
gcattggctt ctaacgatgt gcttcgaact ctcagggaaa tgagagccag aactccaatg   1980
ggagggttcg aatttatggc tcctccacaa gccaagtact atgaaggagt ccgtagaatc   2040
gctggagatg tcttgtcaga ggaacagatc aaggagtgtc aagaactggg tgttatggtt   2100
gatcgagacg atcaaggtgt gctactccag atcttcacca aaccagttgg tgatcgtccc   2160
acttttttcc tcgaaatgat tcagcgaata ggatgcatgg agaaggatga agttgggcaa   2220
gagtaccaga aaggtggatg tggtgggttt ggaaagggga cttttccga  gttgttcaag   2280
tccatagagg actacgagaa gtcactggaa gtcaagcagt ctgtcgttgc tcagaagagc   2340
taagagctct tcatatgacg atcgttcaaa catttggcaa taaagtttct taagattgaa   2400
tcctgttgcc ggtcttgcga tgattatcat ataatttctg ttgaattacg ttaagcatgt   2460
aataattaac atgtaatgca tgacgttatt tatgagatgg gttttatga  ttagagtccc   2520
gcaattatac atttaatacg cgatagaaaa caaaatatag cgcgcaaact aggataaatt   2580
atcgcgcgcg gtgtcatcta tgttactaga tcgcggaccg aagcttgcat gcctgcaggt   2640
cgactctaga ggatctggga cccagtcaaa gattcaaata gaggacctaa cagaactcgc   2700
cgtaaagact ggcgaacagt tcatacagag tctcttacga ctcaatgaca agaagaaaat   2760
cttcgtcaac atggtggagc acgacacgct tgtctactcc aaaaatatca agatacagt   2820
ctcagaagac caaagggcaa ttgagacttt tcaacaaagg gtaatatccg gaaacctcct   2880
cggattccat tgcccagcta tctgtcactt tattgtgaag atagtggaaa aggaaggtgg   2940
ctcctacaaa tgccatcatt gcgataaagg aaaggccatc gttgaagatg cctctgccga   3000
cagtggtccc aaagatggac ccccacccac gaggagcatc gtggaaaaag aagacgttcc   3060
aaccacgtct tcaaagcaag tggattgatg tgatatctcc actgacgtaa gggatgacgc   3120
acaatcccac tatccttcgc aagacccttc ctctatataa ggaagttcat ttcatttgga   3180
gaggacacgc tgaaatcact agtccaccat gtctccggag aggagaccag ttgagattag   3240
gccagctaca gcagctgata tggccgcggt ttgtgatatc gttaaccatt acattgagac   3300
gtctacagtg aactttagga cagagccaca acaccacaa  gagtggattg atgatctaga   3360
gaggttgcaa gatagatacc cttggttggt tgctgaggtt gagggtgttg tggctggtat   3420
tgcttacgct gggccctgga aggctaggaa cgcttacgat tggacagttg agagtactgt   3480
ttacgtgtca cataggcatc aaaggttggg cctaggatcc acattgtaca cacatttgct   3540
taagtctatg gaggcgcaag ttttaagtc  tgtggttgct gttataggcc ttccaaacga   3600
tccatctgtt aggttgcatg aggctttggg atacacagcc cggggtacat tgcgcgcagc   3660
```

```
tggatacaag catggtggat ggcatgatgt tggttttgg caaagggatt ttgagttgcc      3720
agctcctcca aggccagtta ggccagttac ccagatctga actagtgata tcggcgccat      3780
gggtcgacct gcagatcgtt caaacatttg caataaagt ttcttaagat tgaatcctgt      3840
tgccggtctt gcgatgatta tcatataatt tctgttgaat tacgttaagc atgtaataat      3900
taacatgtaa tgcatgacgt tatttatgag atgggttttt atgattagag tcccgcaatt      3960
atacatttaa tacgcgatag aaaacaaaat atagcgcgca aactaggata aattatcgcg      4020
cgcggtgtca tctatgttac tagatccgga cccagctgct tgtggggacc agacaaaaaa      4080
ggaatggtgc agaattgtta ggcgcaccta ccaaaagcat cttgcctt attgcaaaga       4140 taaagcagat tcctctagta caagtgggga acaaataac gtggaaaaga gctgtcctga       4200
cagcccactc actaatgcgt atgacgaacg cagtgacgac cacaaaactc gagactttc       4260 aacaaagggt aatatccgga aacctcctcg gattccattg cccagctatc tgtcacttta      4320
ttgtgaagat agtggaaaag gaaggtggct cctacaaatg ccatcattgc gataaaggaa      4380
aggctatcgt tgaagatgcc tctgccgaca gtggtcccaa agatggaccc ccacccacga      4440
ggagcatcgt ggaaaaagaa gacgttccaa ccacgtcttc aaagcaagtg gattgatgtg      4500
atatctccac tgacgtaagg gatgacgaac aatcccacta tccttctgcc ggaccctcat      4560
gagcggagaa ttaagggagt cacgttatga ccccgccga tgacgcggga caagccgttt       4620
tacgtttgga actgacagaa ccgcaacgaa gctttggcag acaaagtggc agacatactg      4680
tcccacaaat gaagatggaa tctgtaaaag aaaacgcgtg aaataatgcg tctgacaaag      4740
gttaggtcgg ctgcctttaa tcaataccaa agtggtccct accacgatgg aaaaactgtg      4800
cagtcggttt ggcttttct gacgaacaaa taagattcgt ggccgacagg tgggggtcca       4860
ccatgtgaag gcatcttcag actccaataa tggagcaatg acgtaagggc ttacgaaata      4920
agtaagggta gtttgggaaa tgtccactca cccgtcagtc tataaatact agcccctcc       4980 ctcattgtta agggagcaaa atctcagaga gatagtccta gagagagaaa gagagcaagt      5040
agcctagaag tggatcccac catgtctccg gagaggagac cagttgagat taggccagct      5100
acagcagctg atatggccgc ggtttgtgat atcgttaacc attacattga gacgtctaca      5160
gtgaacttta ggacagagcc acaaacacca caagagtgga ttgatgatct agagaggttg      5220
caagatagat acccttggtt ggttgctgag gttgagggtg ttgtggctgg tattgcttac      5280
gctgggccct ggaaggctag gaacgcttac gattggacag ttgagagtac tgtttacgtg      5340
tcacataggc atcaaaggtt gggcctagga tctacattgt acacacattt gcttaagtct      5400
atggaggcgc aaggttttaa gtctgtggtt gctgttatag gccttccaaa cgatccatct      5460
gttaggttgc atgaggcttt gggatacaca gcccggggta cattgcgcgc agctggatac      5520
aagcatggtg gatggcatga tgttggtttt tggcaaaggg attttgagtt gccagctcct      5580
ccaaggccag ttaggccagt tacccagata tgagtcgagc tctagatccc cgaatttccc      5640
cgatcgttca acatttggc aataaagtt cttaagattg aatcctgttg ccggtcttgc        5700
gatgattatc atataatttc tgttgaatta cgttaagcat gtaataatta acatgtaatg      5760
catgacgtta tttatgagat gggttttat gattagagtc ccgcaattat acatttaata      5820
cgcgatagaa aacaaatat agcgcgcaaa ctaggataaa ttatcgcgcg cggtgtcatc       5880
tatgttacta gatcgggaat tgggtaccat gcccggcgg ccagcatggc cgtatccgca       5940
atgtgttatt aagttgtcta agcgtcaatt tgtttacacc acaatatatc ctgccaccag      6000
```

```
ccagccaaca gctccccgac cggcagctcg gcacaaaatc accactcgat acaggcagcc    6060
catcagaatt aattctcatg tttgacagct tatcatcgac tgcacggtgc accaatgctt    6120
ctggcgtcag gcagccatcg gaagctgtgg tatggctgtg caggtcgtaa atcactgcat    6180
aattcgtgtc gctcaaggcg cactcccgtt ctggataatg ttttttgcgc cgacatcata    6240
acggttctgg caaatattct gaaatgagct gttgacaatt aatcatccgg ctcgtataat    6300
gtgtggaatt gtgagcggat aacaatttca cacaggaaac agaccatgag gaagcgttg     6360
atcgccgaag tatcgactca actatcagag gtagttggcg tcatcgagcg ccatctcgaa    6420
ccgacgttgc tggccgtaca tttgtacggc tccgcagtgg atggcggcct gaagccacac    6480
agtgatattg atttgctggt tacggtgacc gtaaggcttg atgaaacaac gcggcgagct    6540
ttgatcaacg accttttgga aacttcggct tcccctggag agagcgagat tctccgcgct    6600
gtagaagtca ccattgttgt gcacgacgac atcattccgt ggcgttatcc agctaagcgc    6660
gaactgcaat ttggagaatg gcagcgcaat gacattcttg caggtatctt cgagccagcc    6720
acgatcgaca ttgatctggc tatcttgctg acaaaagcaa gagaacatag cgttgccttg    6780
gtaggtccag cggcggagga actctttgat ccggttcctg aacaggatct atttgaggcg    6840
ctaaatgaaa ccttaacgct atggaactcg ccgcccgact gggctggcga tgagcgaaat    6900
gtagtgctta cgttgtcccg catttggtac agcgcagtaa ccggcaaaat cgcgccgaag    6960
gatgtcgctg ccgactgggc aatggagcgc ctgccggccc agtatcagcc cgtcatactt    7020
gaagctaggc aggcttatct tggacaagaa gatcgcttgg cctcgcgcgc agatcagttg    7080
gaagaatttg ttcactacgt gaaaggcgag atcaccaaag tagtcggcaa ataaagctct    7140
agtggatctc cgtacccggg gatctggctc gcggcggacg cacgacgccg gggcgagacc    7200
ataggcgatc tcctaaatca atagtagctg taacctcgaa gcgtttcact tgtaacaacg    7260
attgagaatt tttgtcataa aattgaaata cttggttcgc attttttgtca tccgcggtca    7320
gccgcaattc tgacgaactg cccatttagc tggagatgat tgtacatcct tcacgtgaaa    7380
atttctcaag cgctgtgaac aagggttcag attttagatt gaaaggtgag ccgttgaaac    7440
acgttcttct tgtcgatgac gacgtcgcta tgcggcatct tattattgaa taccttacga    7500
tccacgcctt caaagtgacc gcggtagccg acagcaccca gttcacaaga gtactctctt    7560
ccgcgacggt cgatgtcgtg gttgttgatc tagatttagg tcgtgaagat gggctcgaga    7620
tcgttcgtaa tctggcggca aagtctgata ttccaatcat aattatcagt ggcgaccgcc    7680
ttgaggagac ggataaagtt gttgcactcg agctaggagc aagtgatttt atcgctaagc    7740
cgttcagtat cagagagttt ctagcacgca ttcgggttgc cttgcgcgtg cgccccaacg    7800
ttgtccgctc caaagaccga cggtcttttt gttttactga ctggacactt aatctcaggc    7860
aacgtcgctt gatgtccgaa gctggcggtg aggtgaaact tacggcaggt gagttcaatc    7920
ttctcctcgc gtttttagag aaaccccgcg acgttctatc gcgcgagcaa cttctcattg    7980
ccagtcgagt acgcgacgag gaggtttatg acaggagtat agatgttctc atttttgaggc    8040
tgcgccgcaa acttgaggca gatccgtcaa gccctcaact gataaaaaca gcaagaggtg    8100
ccggttattt ctttgacgcg gacgtgcagg tttcgcacgg ggggacgatg gcagcctgag    8160
ccaattccca gatccccgag gaatcggcgt gagcggtcgc aaaccatccg gcccggtaca    8220
aatcggcgcg cgctgggtg atgacctggt ggagaagttg aaggccgcgc aggccgccca    8280
gcggcaacgc atcgaggcag aagcacgccc cggtgaatcg tggcaagcgg ccgctgatcg    8340
aatccgcaaa gaatcccggc aaccgccggc agccggtgcg ccgtcgatta ggaagccgcc    8400
```

```
caagggcgac gagcaaccag atttttcgt tccgatgctc tatgacgtgg gcacccgcga    8460
tagtcgcagc atcatggacg tggccgtttt ccgtctgtcg aagcgtgacc gacgagctgg   8520
cgaggtgatc cgctacgagc ttccagacgg gcacgtagag gtttccgcag ggccggccgg   8580
catggccagt gtgtgggatt acgacctggt actgatggcg gtttcccatc taaccgaatc   8640
catgaaccga taccgggaag ggaagggaga caagcccggc cgcgtgttcc gtccacacgt   8700
tgcggacgta ctcaagttct gccggcgagc cgatggcgga aagcagaaag acgacctggt   8760
agaaacctgc attcggttaa acaccacgca cgttgccatg cagcgtacga agaaggccaa   8820
gaacggccgc ctggtgacgg tatccgaggg tgaagccttg attagccgct acaagatcgt   8880
aaagagcgaa accgggcggc cggagtacat cgagatcgag ctagctgatt ggatgtaccg   8940
cgagatcaca gaaggcaaga acccggacgt gctgacggtt caccccgatt acttttgat    9000 cgatcccggc atcggccgtt ttctctaccg cctggcacgc cgcgccgcag gcaaggcaga   9060
agccagatgg ttgttcaaga cgatctacga acgcagtggc agcgccggag agttcaagaa   9120
gttctgtttc accgtgcgca agctgatcgg gtcaaatgac ctgccggagt acgatttgaa   9180
ggaggaggcg gggcaggctg gcccgatcct agtcatgcgc taccgcaacc tgatcgaggg   9240
cgaagcatcc gccggttcct aatgtacgga gcagatgcta gggcaaattg ccctagcagg   9300
ggaaaaaggt cgaaaggtc tcttcctgt ggatagcacg tacattggga acccaaagcc     9360
gtacattggg aaccggaacc cgtacattgg gaacccaaag ccgtacattg ggaaccggtc   9420
acacatgtaa gtgactgata taaagagaa aaaaggcgat ttttccgcct aaaactcttt    9480
aaaacttatt aaaactctta aaacccgcct ggcctgtgca taactgtctg gccagcgcac   9540
agccgaagag ctgcaaaaag cgcctaccct tcggtcgctg cgctccctac gccccgccgc   9600
ttcgcgtcgg cctatcgcgg ccgctggccg ctcaaaaatg gctggcctac ggccaggcaa   9660
tctaccaggg cgcggacaag ccgcgccgtc gccactcgac cgccggcgct gaggtctgcc   9720
tcgtgaagaa ggtgttgctg actcatacca ggcctgaatc gccccatcat ccagccagaa   9780
agtgagggag ccacggttga tgagagcttt gttgtaggtg gaccagttgg tgattttgaa   9840
cttttgcttt gccacggaac ggtctgcgtt gtcgggaaga tgcgtgatct gatccttcaa   9900
ctcagcaaaa gttcgattta ttcaacaaag ccgccgtccc gtcaagtcag cgtaatgctc   9960
tgccagtgtt acaaccaatt aaccaattct gattagaaaa actcatcgag catcaaatga   10020
aactgcaatt tattcatatc aggattatca ataccatatt tttgaaaaag ccgtttctgt   10080
aatgaaggag aaaactcacc gaggcagttc cataggatgg caagatcctg gtatcggtct   10140
gcgattccga ctcgtccaac atcaatacaa cctattaatt tcccctcgtc aaaaataagg   10200
ttatcaagtg agaaatcacc atgagtgacg actgaatccg gtgagaatgg caaaagctct   10260
gcattaatga tcggccaac gcgcggggag aggcggtttg cgtattgggc gctcttccgc    10320
ttcctcgctc actgactcgc tgcgctcggt cgttcggctg cggcgagcgg tatcagctca   10380
ctcaaaggcg gtaatacggt tatccacaga atcagggat aacgcaggaa agaacatgtg    10440
agcaaaaggc cagcaaaagg ccaggaaccg taaaaaggcc gcgttgctgg cgttttccca   10500
taggctccgc cccctgacg agcatcacaa aaatcgacgc tcaagtcaga ggtggcgaaa   10560
cccgacagga ctataaagat accaggcgtt tcccctgga agctccctcg tgcgctctcc    10620
tgttccgacc ctgccgctta ccggatacct gtccgccttt ctcccttcgg gaagcgtggc   10680
gctttctcat agctcacgct gtaggtatct cagttcggtg taggtcgttc gctccaagct   10740
```

```
gggctgtgtg cacgaaccccc ccgttcagcc cgaccgctgc gccttatccg gtaactatcg    10800
tcttgagtcc aacccggtaa gacacgactt atcgccactg gcagcagcca ctggtaacag    10860
gattagcaga gcgaggtatg taggcggtgc tacagagttc ttgaagtggt ggcctaacta    10920
cggctacact agaagaacag tatttggtat ctgcgctctg ctgaagccag ttaccttcgg    10980
aaaaagagtt ggtagctctt gatccggcaa acaaaccacc gctggtagcg gtggtttttt    11040
tgtttgcaag cagcagatta cgcgcagaaa aaaggatct caagaagatc ctttgatctt     11100
ttctacgggg tctgacgctc agtggaacga aaactcacgt taagggattt tggtcatgag    11160
attatcaaaa aggatcttca cctagatcct tttgatccgg aatta                   11205
```

<210> SEQ ID NO 34
<211> LENGTH: 10841
<212> TYPE: DNA
<213> ORGANISM: Artificial Sequence
<220> FEATURE:
<223> OTHER INFORMATION: vector

<400> SEQUENCE: 34

```
attcctgtgg ttggcatgca catacaaatg gacgaacgga taaacctttt cacgcccttt      60
taaatatccg attattctaa taaacgctct tttctcttag gtttaccccgc caatatatcc     120 tgtcaaacac tgatagttta aactgaaggc gggaaacgac aatctgatca tgagcggaga     180 attaaggag tcacgttatg acccccgccg atgacgcggg acaagccgtt ttacgtttgg      240
aactgacaga accgcaacgc tgcaggaatt ggccgcagcg gccatttaaa tcaattgggc     300
gcgtacgtag cactagtgaa ttccggaccc aagcttgcat gcctgcagga attggccgca    360
gcggccattt aaatcaattg gcgcgtgcg gccgcagctg cttgtgggga ccagacaaaa      420
aaggaatggt gcagaattgt taggcgcacc taccaaaagc atctttgcct ttattgcaaa     480
gataaagcag attcctctag tacaagtggg gaacaaaata acgtggaaaa gagctgtcct    540
gacagcccac tcactaatgc gtatgacgaa cgcagtgacg accacaaaac tcgagctttt    600
tcaacaaagg gtaatatccg gaaacctcct cggattccat tgcccagcta tctgtcactt    660
tattgtgaag atagtggaaa aggaaggtgg ctcctacaaa tgccatcatt gcgataaagg    720
aaaggctatc gttgaagatg cctctgccga cagtggtccc aaagatggac ccccacccac    780
gaggagcatc gtggaaaaag aagacgttcc aaccacgtct tcaaagcaag tggattgatg    840
tgatatctcc actgacgtaa gggatgacga acaatcccac tatccttctg caggtcgact    900
ctagaggatc ctataaatag gaagttcatt tcatttggag aggaaacctc gagtattttt     960
acaacaatta ccaacaacaa caacaacaa acaacattac aattactatt tacaattaca    1020
catatgcctc caacaccagc tactgctact ggagctgctg ctgctgccgt tacaccagaa    1080
catgctgcaa ggtcattccc tagagttgtt cgcgttaacc ctaggtctga cagattccct    1140
gttctgtcct tccatcatgt ggagctttgg tgtgctgatg cagctagtgc tgctggtcgt    1200
ttcagctttg cacttggagc accacttgct gcaagatctg atctgtctac agggaactca    1260
gcacatgctt ctctcctact tcgatctgga gcattagcct tccttttta cgctccttat    1320 gctccacctc cacaagaagc tgcaactgct gcaactgctt ccattccctc cttttcagca    1380
gatgctgcaa gaacctttgc tgctgcacat ggacttgctg tcagatctgt tggagttagg    1440
gttgctgatg cagctgaagc atttcgcgtt agtgttgctg gaggagcaag acctgctttt    1500
gctccagcag atcttggtca cggatttgga cttgctgaag tggagctgta tggagatgtg    1560
gttctgagat tcgtgagcta tcctgacgaa actgacctac catttctccc aggattcgag    1620
```

```
agggtttcaa gtccaggtgc agttgactac ggtttgactc gctttgacca cgttgttgga    1680
aacgttccag aaatggctcc tgtcatcgac tacatgaagg gattccttgg tttccacgag    1740
ttcgctgaat tcacagcaga ggatgttgga accacagaat ctggactgaa cagtgtggtt    1800
ctagccaaca acagtgaagc tgttcttctg ccattgaacg agcctgttca tggaaccaag    1860
agacgatctc agatccaaac ctacctcgaa taccatggtg gaccaggagt tcaacacatc    1920
gcattggctt ctaacgatgt gcttcgaact ctcaggaaaa tgagagccag aactccaatg    1980
ggagggttcg aatttatggc tcctccacaa gccaagtact atgaaggagt ccgtagaatc    2040
gctggagatg tcttgtcaga ggaacagatc aaggagtgtc aagaactggg tgttatggtt    2100
gatcgagacg atcaaggtgt gctactccag atcttcacca aaccagttgg tgatcgtccc    2160
acttttttcc tcgaaatgat tcagcgaata ggatgcatgg agaaggatga agttgggcaa    2220
gagtaccaga aaggtggatg tggtgggttt ggaaagggga acttttccga gttgttcaag    2280
tccatagagg actacgagaa gtcactggaa gtcaagcagt ctgtcgttgc tcagaagagc    2340
taagagctct tcatatgacg atcgttcaaa catttggcaa taaagtttct taagattgaa    2400
tcctgttgcc ggtcttgcga tgattatcat ataatttctg ttgaattacg ttaagcatgt    2460
aataattaac atgtaatgca tgacgttatt tatgagatgg gttttatga ttagagtccc     2520
gcaattatac atttaatacg cgatagaaaa caaaatatag cgcgcaaact aggataaatt    2580
atcgcgcgcg gtgtcatcta tgttactaga tcgcggaccg aagcttgcat gcctgcaggt    2640
cgactctaga ggatctggga cccagctgct tgtggggacc agacaaaaaa ggaatggtgc    2700
agaattgtta ggcgcaccta ccaaaagcat ctttgccttt attgcaaaga taaagcagat    2760
tcctctagta caagtgggga acaaaataac gtggaaaaga gctgtcctga cagcccactc    2820
actaatgcgt atgacgaacg cagtgacgac cacaaaactc gagactttt caacaagggt     2880
aatatccgga aacctcctcg gattccattg cccagctatc tgtcactta ttgtgaagat     2940
agtggaaaag gaaggtggct cctacaaatg ccatcattgc gataaaggaa aggctatcgt    3000
tgaagatgcc tctgccgaca gtggtcccaa agatggaccc ccacccacga ggagcatcgt    3060
ggaaaagaa gacgttccaa ccacgtcttc aaagcaagtg gattgatgtg atatctccac     3120
tgacgtaagg gatgacgaac aatcccacta tccttctgcc ggaccctcat gagcggagaa    3180
ttaagggagt cacgttatga cccccgccga tgacgcggga caagccgttt acgtttgga    3240
actgacagaa ccgcaacgaa gctttggcag acaaagtggc agacatactg tcccacaaat    3300
gaagatggaa tctgtaaaag aaaacgcgtg aaataatgcg tctgacaaag gttaggtcgg    3360
ctgcctttaa tcaataccaa agtggtccct accacgatgg aaaaactgtg cagtcggttt    3420
ggcttttct gacgaacaaa taagattcgt ggccgacagg tggggtcca ccatgtgaag     3480
gcatcttcag actccaataa tggagcaatg acgtaagggc ttacgaaata agtaagggta    3540
gtttgggaaa tgtccactca cccgtcagtc tataaatact tagccccctcc ctcattgtta    3600
agggagcaaa atctcagaga gatagtccta gagagagaaa gagagcaagt agcctagaag    3660
tggatcccac catggctcaa gtttctagag ttcataacct tgctcaatct actcaaattt    3720
tcggacattc ttctaactct aacaagctta agtctgttaa ctctgtttct cttagaccaa    3780
gactttgggg agcttctaag tctagaattc caatgcataa gaacggatct ttcatgggaa    3840
acttcaacgt tggaaaggga aactctggag ttttcaaggt ttctgcttct gttgctgctg    3900
ctgagaagcc atctacttct ccagagattg ttcttgagcc aattaaggat ttctctggaa    3960
```

```
ctattactct tccaggatct aagtctcttt ctaacagaat tcttcttctt gctgctcttt   4020
ctgagggaac tactgttgtt gataaccttc tttattctga ggatattcat tatatgcttg   4080
gtgctcttag aactcttgga cttagagttg aggatgataa gactactaag caagctattg   4140
ttgagggatg cggaggactt ttcccaactt ctaaggagtc taaggatgag attaaccttt   4200
tccttggaaa cgctggaatt gctatgagat ctcttactgc tgctgttgtt gctgctggag   4260
gaaacgcttc ttatgttctt gatggagttc aagaatgag  agagagacca attggagatc   4320
ttgttgctgg acttaagcaa cttggagctg atgttgattg cttccttgga actaactgcc   4380
caccagttag agttaacgga aagggaggac ttccaggagg aaaggttaag ctttctggat   4440
ctgtttcttc tcaatatctt actgctcttc ttatggctgc tccacttgct cttggagatg   4500
ttgagattga gattgttgat aagcttattt ctgttcctta tgttgagatg actcttaagc   4560
ttatggagag attcggagtt tctgttgagc attctgaaaa ctgggataga ttccttgttc   4620
atggaggaca aaagtataag tctccaggaa acgctttcgt tgaggagat  gcttcttctg   4680
cttcttatct tcttgctgga gctgctatta ctggaggaac tattactgtt aacggatgcg   4740
gaacttcttc tcttcaagga gatgttaagt tcgctgaggt tcttgagaag atgggagcta   4800
aggttacttg gtctgagaac tctgttactg tttctggacc accaagagat ttctctggaa   4860
gaaaggttct tagaggaatt gatgttaaca tgaacaagat gccagatgtt gctatgactc   4920
ttgctgttgt tgctctcttt c gctaacggac caactgctat tagagatgtt gcttcttgga   4980
gagttaagga gactgagaga atgattgcta tttgcactga gcttagaaag cttggagcta   5040
ctgttgagga gggaccagat tattgcgtta ttactccacc agagaagctt aacgttactg   5100
ctattgatac ttatgatgat catagaatgg ctatggcttt ctctcttgct gcttgcggag   5160
atgttccagt tactattaaa gatccaggat gcactagaaa gactttccca gattatttcg   5220
aggttcttga gagacttact aagcattaag tcgagctcta gatccccgaa tttccccgat   5280
cgttcaaaca tttggcaata agtttcttag agattgaatc ctgttgccgg tcttgcgatg   5340
attatcatat aatttctgtt gaattacgtt aagcatgtaa taattaacat gtaatgcatg   5400
acgttattta tgagatgggt ttttatgatt agagtcccgc aattatacat ttaatacgcg   5460
atagaaaaca aaatatagcg cgcaaactag gataaattat cgcgcgcggt gtcatctatg   5520
ttactagatc gggaattggg taccatgccc gggcggccag catggccgta tccgcaatgt   5580
gttattaagt tgtctaagcg tcaatttgtt tacaccacaa tatatcctgc caccagccag   5640
ccaacagctc cccgaccggc agctcggcac aaaatcacca ctcgatacag gcagcccatc   5700
agaattaatt ctcatgtttg acagcttatc atcgactgca cggtgcacca atgcttctgg   5760
cgtcaggcag ccatcggaag ctgtggtatg gctgtgcagg tcgtaaatca ctgcataatt   5820
cgtgtcgctc aaggcgcact cccgttctgg ataatgtttt ttgcgccgac atcataacgg   5880
ttctggcaaa tattctgaaa tgagctgttg acaattaatc atccggctcg tataatgtgt   5940
ggaattgtga gcggataaca atttcacaca ggaaacagac catgagggaa gcgttgatcg   6000
ccgaagtatc gactcaacta tcagaggtag ttggcgtcat cgagcgccat ctcgaaccga   6060
cgttgctggc cgtacatttg tacggctccg cagtggatgg cggcctgaag ccacacagtg   6120
atattgattt gctggttacg gtgaccgtaa ggcttgatga acaacgcgg cgagctttga   6180
tcaacgacct tttggaaact tcggcttccc ctggagagag cgagattctc cgcgctgtag   6240
aagtcaccat tgttgtgcac gacgacatca ttccgtggcg ttatccagct aagcgcgaac   6300
tgcaatttgg agaatggcag cgcaatgaca ttcttgcagg tatcttcgag ccagccacga   6360
```

```
tcgacattga tctggctatc ttgctgacaa aagcaagaga acatagcgtt gccttggtag    6420
gtccagcggc ggaggaactc tttgatccgg ttcctgaaca ggatctattt gaggcgctaa    6480
atgaaacctt aacgctatgg aactcgccgc ccgactgggc tggcgatgag cgaaatgtag    6540
tgcttacgtt gtcccgcatt tggtacagcg cagtaaccgg caaaatcgcg ccgaaggatg    6600
tcgctgccga ctgggcaatg gagcgcctgc cggcccagta tcagcccgtc atacttgaag    6660
ctaggcaggc ttatcttgga caagaagatc gcttggcctc gcgcgcagat cagttggaag    6720
aatttgttca ctacgtgaaa ggcgagatca ccaaagtagt cggcaaataa agctctagtg    6780
gatctccgta cccgggggatc tggctcgcgc ggacgcacg acgccggggc gagaccatag    6840
gcgatctcct aaatcaatag tagctgtaac ctcgaagcgt ttcacttgta acaacgattg    6900 agaattttg tcataaaatt gaaatacttg gttcgcattt ttgtcatccg cggtcagccg    6960
caattctgac gaactgccca tttagctgga gatgattgta catccttcac gtgaaaattt    7020
ctcaagcgct gtgaacaagg gttcagattt tagattgaaa ggtgagccgt tgaaacacgt    7080
tcttcttgtc gatgacgacg tcgctatgcg gcatcttatt attgaatacc ttacgatcca    7140
cgccttcaaa gtgaccgcgg tagccgacag cacccagttc acaagagtac tctcttccgc    7200
gacggtcgat gtcgtggttg ttgatctaga tttaggtcgt gaagatgggc tcgagatcgt    7260
tcgtaatctg gcggcaaagt ctgatattcc aatcataatt atcagtggcg accgccttga    7320
ggagacggat aaagttgttg cactcgagct aggagcaagt gattttatcg ctaagccgtt    7380
cagtatcaga gagtttctag cacgcattcg ggttgccttg cgcgtgcgcc caacgttgt    7440 ccgctccaaa gaccgacggt cttttgttt tactgactgg acacttaatc tcaggcaacg    7500
tcgcttgatg tccgaagctg gcggtgaggt gaaacttacg gcaggtgagt tcaatcttct    7560
cctcgcgttt ttagagaaac cccgcgacgt tctatcgcgc gagcaacttc tcattgccag    7620
tcgagtacgc gacgaggagg tttatgacag gagtatagat gttctcattt tgaggctgcg    7680
ccgcaaactt gaggcagatc cgtcaagccc tcaactgata aaaacagcaa gaggtgccgg    7740
ttatttcttt gacgcggacg tgcaggtttc gcacggggg acgatggcag cctgagccaa    7800
ttcccagatc cccgaggaat cggcgtgagc ggtcgcaaac catccggccc ggtacaaatc    7860
ggcgcggcgc tgggtgatga cctggtggag aagttgaagg ccgcgcaggc cgcccagcgg    7920
caacgcatcg aggcagaagc acgccccggt gaatcgtggc aagcggccgc tgatcgaatc    7980
cgcaaagaat cccggcaacc gccggcagcc ggtgcgccgt cgattaggaa gccgcccaag    8040
ggcgacgagc aaccagattt tttcgttccg atgctctatg acgtgggcac ccgcgatagt    8100
cgcagcatca tggacgtggc cgttttccgt ctgtcgaagc gtgaccgacg agctggcgag    8160
gtgatccgct acgagcttcc agacgggcac gtagaggttt ccgcagggcc ggccggcatg    8220
gccagtgtgt gggattacga cctggtactg atggcggttt cccatctaac cgaatccatg    8280
aaccgatacc gggaagggaa gggagacaag cccggccgcg tgttccgtcc acacgttgcg    8340
gacgtactca agttctgccg gcgagccgat ggcggaaagc agaaagacga cctggtagaa    8400
acctgcattc ggttaaacac cacgcacgtt gccatgcagc gtacgaagaa ggccaagaac    8460
ggccgcctgg tgacggtatc cgagggtgaa gccttgatta gccgctacaa gatcgtaaag    8520
agcgaaaccg ggcggccgga gtacatcgag atcgagctag ctgattggat gtaccgcgag    8580
atcacagaag gcaagaaccc ggacgtgctg acggttcacc ccgattactt tttgatcgat    8640
cccggcatcg gccgttttct ctaccgcctg gcacgccgcg ccgcaggcaa ggcagaagcc    8700
```

| | |
|---|---|
| agatggttgt tcaagacgat ctacgaacgc agtggcagcg ccggagagtt caagaagttc | 8760 |
| tgtttcaccg tgcgcaagct gatcgggtca aatgacctgc cggagtacga tttgaaggag | 8820 |
| gaggcgggc aggctggccc gatcctagtc atgcgctacc gcaacctgat cgagggcgaa | 8880 |
| gcatccgccg gttcctaatg tacggagcag atgctagggc aaattgccct agcaggggaa | 8940 |
| aaaggtcgaa aaggtctctt tcctgtggat agcacgtaca ttgggaaccc aaagccgtac | 9000 |
| attgggaacc ggaacccgta cattgggaac ccaaagccgt acattgggaa ccggtcacac | 9060 |
| atgtaagtga ctgatataaa agagaaaaaa ggcgattttt ccgcctaaaa ctctttaaaa | 9120 |
| cttattaaaa ctcttaaaac ccgcctggcc tgtgcataac tgtctggcca gcgcacagcc | 9180 |
| gaagagctgc aaaaagcgcc taccettcgg tcgctgcgct ccctacgccc cgccgcttcg | 9240 |
| cgtcggccta tcgcggccgc tggccgctca aaaatggctg gcctacgcc aggcaatcta | 9300 |
| ccagggcgcg gacaagccgc gccgtcgcca ctcgaccgcc ggcgctgagg tctgcctcgt | 9360 |
| gaagaaggtg ttgctgactc ataccaggcc tgaatcgccc catcatccag ccagaaagtg | 9420 |
| agggagccac ggttgatgag agctttgttg taggtggacc agttggtgat tttgaacttt | 9480 |
| tgctttgcca cggaacggtc tgcgttgtcg ggaagatgcg tgatctgatc cttcaactca | 9540 |
| gcaaaagttc gatttattca acaaagccgc cgtcccgtca agtcagcgta atgctctgcc | 9600 |
| agtgttacaa ccaattaacc aattctgatt agaaaaactc atcgagcatc aaatgaaact | 9660 |
| gcaatttatt catatcagga ttatcaatac catattttg aaaaagccgt ttctgtaatg | 9720 |
| aaggagaaaa ctcaccgagg cagttccata ggatggcaag atcctggtat cggtctgcga | 9780 |
| ttccgactcg tccaacatca atacaaccta ttaatttccc ctcgtcaaaa ataaggttat | 9840 |
| caagtgagaa atcaccatga gtgacgactg aatccggtga atggcaaa agctctgcat | 9900 |
| taatgaatcg gccaacgcgc ggggagaggc ggtttgcgta ttgggcgctc ttccgcttcc | 9960 |
| tcgctcactg actcgctgcg ctcggtcgtt cggctgcggc gagcggtatc agctcactca | 10020 |
| aaggcggtaa tacggttatc cacagaatca ggggataacg caggaaagaa catgtgagca | 10080 |
| aaaggccagc aaaaggccag gaaccgtaaa aaggccgcgt tgctggcgtt tttccatagg | 10140 |
| ctccgcccc ctgacgagca tcacaaaaat cgacgctcaa gtcagaggtg gcgaaacccg | 10200 |
| acaggactat aaagatacca ggcgtttccc cctggaagct ccctcgtgcg ctctcctgtt | 10260 |
| ccgaccctgc cgcttaccgg atacctgtcc gcctttctcc cttcgggaag cgtggcgctt | 10320 |
| tctcatagct cacgctgtag gtatctcagt tcggtgtagg tcgttcgctc caagctgggc | 10380 |
| tgtgtgcacg aaccccccgt tcagcccgac cgctgcgcct tatccggtaa ctatcgtctt | 10440 |
| gagtccaacc cggtaagaca cgacttatcg ccactggcag cagccactgg taacaggatt | 10500 |
| agcagagcga ggtatgtagg cggtgctaca gagttcttga agtggtggcc taactacggc | 10560 |
| tacactagaa gaacagtatt tggtatctgc gctctgctga agccagttac cttcggaaaa | 10620 |
| agagttggta gctcttgatc cggcaaacaa accaccgctg gtagcggtgg tttttttgtt | 10680 |
| tgcaagcagc agattacgcg cagaaaaaaa ggatctcaag aagatccttt gatcttttct | 10740 |
| acggggtctg acgctcagtg gaacgaaaac tcacgttaag ggattttggt catgagatta | 10800 |
| tcaaaaagga tcttcaccta gatcctttg atccggaatt a | 10841 |

```
<210> SEQ ID NO 35
<211> LENGTH: 9192
<212> TYPE: DNA
<213> ORGANISM: Artificial Sequence
<220> FEATURE:
<223> OTHER INFORMATION: vector
```

<400> SEQUENCE: 35

```
aattcctgtg gttggcatgc acatacaaat ggacgaacgg ataaacctit tcacgccctt      60
ttaaatatcc gattattcta ataaacgctc ttttctctta ggtttacccg ccaatatatc     120
ctgtcaaaca ctgatagttt aaacgggacc cggcgcgcca tttaaatggt accggtccgc     180
gatctagtaa catagatgac accgcgcgcg ataatttatc ctagtttgcg cgctatattt     240
tgttttctat cgcgtattaa atgtataatt gcgggactct aatcataaaa acccatctca     300
taaataacgt catgcattac atgttaatta ttacatgctt aacgtaattc aacagaaatt     360
atatgataat catcgcaaga ccggcaacag gattcaatct taagaaactt tattgccaaa     420
tgtttgaacg atcgtcatat gaagagctct tagctcttct gagcaacgac agactgcttg     480
acttccagtg acttctcgta gtcctctatg gacttgaaca actcggaaaa gttcccctit     540
ccaaacccac cacatccacc tttctggtac tcttgcccaa cttcatcctt ctccatgcat     600
cctattcgct gaatcatttc gaggaaaaaa gtgggacgat caccaactgg tttggtgaag     660
atctggagta gcacaccttg atcgtctcga tcaacgagaa cacccagttc ttgacactcc     720
ttgatctgtt cctctgacaa gacatctcca gcgattctac ggactccttc atagtacttg     780
gcttgtggag gagccataaa ttcgaaccct cccattggag ttctggctct catttccctg     840
agagttcgaa gcacatcgtt agaagccaat gcgatgtgtt gaactcctgg tccaccatgg     900
tattcgaggt aggtttggat ctgagatcgt ctcttggttc catgaacagg ctcgttcaat     960
ggcagaagaa cagcttcact gttgttggct agaaccacac tgttcagtcc agattctgtg    1020
gttccaacat cctctgctgt gaattcagcg aactcgtgga aaccaaggaa tcccttcatg    1080
tagtcgatga caggagccat ttctggaacg tttccaacaa cgtggtcaaa gcgagtcaaa    1140
ccgtagtcaa ctgcacctgg acttgaaacc ctctcgaatc ctgggagaaa tggtaggtca    1200
gtttcgtcag gatagctcac gaatctcaga accacatctc catacagctc cacttcagca    1260
agtccaaatc cgtgaccaag atctgctgga gcaaaagcag gtcttgctcc tccagcaaca    1320
ctaacgcgaa atgcttcagc tgcatcagca accctaactc caacagatct gacagcaagt    1380
ccatgtgcag cagcaaaggt tcttgcagca tctgctgaaa aggagggaat ggaagcagtt    1440
gcagcagttg cagcttcttg tggaggtgga gcataaggag cggtaaaaag gaaggctaat    1500
gctccagatc gaagtaggag agaagcatgt gctgagttcc ctgtagacag atcagatctt    1560
gcagcaagtg gtgctccaag tgcaaagctg aaacgaccag cagcactagc tgcatcagca    1620
caccaaagct ccacatgatg gaaggacaga acagggaatc tgtcagacct agggttaacg    1680
cgaacaactc tagggaatga ccttgcagca tgttctggtg taacggcagc agcagcagct    1740
ccagtagcag tagctggtgt tggaggcata tgtgtaattg taaatagtaa ttgtaatgtt    1800
gtttgttgtt tgttgttgtt ggtaattgtt gtaaaaatac tcgaggtttc ctctccaaat    1860
gaaatgaact tccatattat aggatcctct agagtcgacc tgcagaagga tagtgggatt    1920
gttcgtcatc ccttacgtca gtggagatat cacatcaatc cacttgcttt gaagacgtgg    1980
ttggaacgtc ttcttttttcc acgatgctcc tcgtgggtgg gggtccatct ttgggaccac    2040
tgtcggcaga ggcatcttca acgatagcct ttcctttatc gcaatgatgg catttgtagg    2100
agccaccttc cttttccact atcttcacaa taaagtgaca gatagctggg caatggaatc    2160
cgaggaggtt tccggatatt acccttgtt gaaaagtctc gagttttgtg gtcgtcactg    2220
cgttcgtcat acgcattagt gagtgggctg tcaggacagc tctttcccac gttattttgt    2280
```

```
tccccacttg tactagagga atctgcttta tctttgcaat aaaggcaaag atgcttttgg    2340
taggtgcgcc taacaattct gcaccattcc tttttgtct ggtccccaca agcagctgcg     2400
gccgcacgcg cccaattgat ttaaatggcc gctgcggcca attcctgcag gcatgcaagc    2460
ttgggtccgg catgcatgca gggatccaca tggagtcaaa gattcaaata gaggacctaa    2520
cagaactcgc cgtaaagact ggcgaacagt tcatacagag tctcttacga ctcaatgaca    2580
agaagaaaat cttcgtcaac atggtggagc acgacacgct tgtctactcc aaaaatatca    2640
aagatacagt ctcagaagac caaagggcaa ttgagacttt tcaacaaagg gtaatatccg    2700
gaaacctcct cggattccat tgcccagcta tctgtcactt tattgtgaag atagtggaaa    2760
aggaaggtgg ctcctacaaa tgccatcatt gcgataaagg aaaggccatc gttgaagatg    2820
cctctgccga cagtggtccc aaagatggac ccccacccac gaggagcatc gtggaaaaag    2880
aagacgttcc aaccacgtct tcaaagcaag tggattgatg tgatatctcc actgacgtaa    2940
gggatgacgc acaatcccac tatccttcgc aagacccttc ctctatataa ggaagttcat    3000
ttcatttgga gaggacacgc tgaaatcact agtatgagcc cagaacgacg cccggccgac    3060
atccgccgtg ccaccgaggc ggacatgccg gcggtctgca ccatcgtcaa ccactacatc    3120
gagacaagca cggtcaactt ccgtaccgag ccgcaggaac gcaggagtg gacggacgac     3180 ctcgtccgtc tgcgggagcg ctatccctgg ctcgtcgccg aggtggacgg cgaggtcgcc    3240
ggcatcgcct acgcgggccc ctggaaggca cgcaacgcct acgactggac ggccgagtcg    3300
accgtgtacg tctcccccg ccaccagcgg acgggactgg gctccacgct ctacacccac     3360
ctgctgaagt ccctggaggc acagggcttc aagagcgtgg tcgctgtcat cgggctgccc    3420
aacgacccga gcgtgcgcat gcacgaggcg ctcggatatg cccccgcgg catgctgcgg    3480 gcggccggct tcaagcacgg gaactggcat gacgtgggtt tctggcagct ggacttcagc    3540
ctgccggtac cgccccgtcc ggtcctgccc gtcaccgaga tatgaactag tgatatcggc    3600
gccatgggtc gacctgcaga tcgttcaaac atttggcaat aaagtttctt aagattgaat    3660
cctgttgccg gtcttgcgat gattatcata taatttctgt tgaattacgt taagcatgta    3720
ataattaaca tgtaatgcat gacgttattt atgagatggg tttttatgat tagagtcccg    3780
caattataca tttaatacgc gatagaaaac aaaatatagc gcgcaaacta ggataaatta    3840
tcgcgcgcgg tgtcatctat gttactagat ctgctagccc tgcaggaaat ttaccggtgc    3900
ccgggcggcc agcatggccg tatccgcaat gtgttattaa gttgtctaag cgtcaatttg    3960
tttacaccac aatatatcct gccaccagcc agccaacagc tccccgaccg gcagctcggc    4020 acaaatcac cactcgatac aggcagccca tcagaattaa ttctcatgtt tgacagctta     4080
tcatcgactg cacggtgcac caatgcttct ggcgtcaggc agccatcgga agctgtggta    4140
tggctgtgca ggtcgtaaat cactgcataa ttcgtgtcgc tcaaggcgca ctcccgttct    4200
ggataatgtt ttttgcgccg acatcataac ggttctggca atattctga atgagctgt      4260 tgacaattaa tcatccggct cgtataatgt gtggaattgt gagcggataa caatttcaca    4320
caggaaacag accatgaggg aagcgttgat cgccgaagta tcgactcaac tatcagaggt    4380
agttggcgtc atcgagcgcc atctcgaacc gacgttgctg gccgtacatt tgtacggctc    4440
cgcagtggat ggcggcctga agccacacag tgatattgat ttgctggtta cggtgaccgt    4500
aaggcttgat gaaacaacgc ggcgagcttt gatcaacgac cttttggaaa cttcggcttc    4560
ccctggagag agcgagattc tccgcgctgt agaagtcacc attgttgtgc acgacgacat    4620
cattccgtgg cgttatccag ctaagcgcga actgcaattt ggagaatggc agcgcaatga    4680
```

```
cattcttgca ggtatcttcg agccagccac gatcgacatt gatctggcta tcttgctgac   4740
aaaagcaaga gaacatagcg ttgccttggt aggtccagcg gcggaggaac tctttgatcc   4800
ggttcctgaa caggatctat ttgaggcgct aaatgaaacc ttaacgctat ggaactcgcc   4860
gcccgactgg gctggcgatg agcgaaatgt agtgcttacg ttgtcccgca tttggtacag   4920
cgcagtaacc ggcaaaatcg cgccgaagga tgtcgctgcc gactgggcaa tggagcgcct   4980
gccggcccag tatcagcccg tcatacttga agctaggcag gcttatcttg acaagaaga   5040 tcgcttggcc tcgcgcgcag atcagttgga agaatttgtt cactacgtga aaggcgagat   5100
caccaaagta gtcggcaaat aaagctctag tggatctccg tacccaggga tctggctcgc   5160
ggcggacgca cgacgccggg gcgagaccat aggcgatctc ctaaatcaat agtagctgta   5220
acctcgaagc gtttcacttg taacaacgat tgagaatttt tgtcataaaa ttgaaatact   5280
tggttcgcat ttttgtcatc cgcggtcagc cgcaattctg acgaactgcc catttagctg   5340
gagatgattg tacatccttc acgtgaaaat ttctcaagcg ctgtgaacaa gggttcagat   5400
tttagattga aggtgagcc gttgaaacac gttcttcttg tcgatgacga cgtcgctatg   5460
cggcatctta ttattgaata ccttacgatc cacgccttca aagtgaccgc ggtagccgac   5520
agcacccagt tcacaagagt actctcttcc gcgacggtcg atgtcgtggt tgttgatcta   5580
gatttaggtc gtgaagatgg gctcgagatc gttcgtaatc tggcggcaaa gtctgatatt   5640
ccaatcataa ttatcagtgg cgaccgcctt gaggagacgg ataaagttgt tgcactcgag   5700
ctaggagcaa gtgattttat cgctaagccg ttcagtatca gagagtttct agcacgcatt   5760
cgggttgcct tgcgcgtgcg ccccaacgtt gtccgctcca aagaccgacg gtctttttgt   5820
tttactgact ggacacttaa tctcaggcaa cgtcgcttga tgtccgaagc tggcggtgag   5880
gtgaaactta cggcaggtga gttcaatctt ctcctcgcgt ttttagagaa accccgcgac   5940
gttctatcgc gcgagcaact tctcattgcc agtcgagtac gcgacgagga ggtttatgac   6000
aggagtatag atgttctcat tttgaggctg cgccgcaaac ttgaggcaga tccgtcaagc   6060
cctcaactga taaaaacagc aagaggtgcc ggttatttct ttgacgcgga cgtgcaggtt   6120
tcgcacgggg ggacgatggc agcctgagcc aattcccaga tccccgagga atcggcgtga   6180
gcggtcgcaa accatccggc ccggtacaaa tcggcgcggc gctgggtgat gacctggtgg   6240
agaagttgaa ggccgcgcag gccgcccagc ggcaacgcat cgaggcagaa gcacgccccg   6300
gtgaatcgtg gcaagcggcc gctgatcgaa tccgcaaaga atcccggcaa ccgccggcag   6360
ccggtgcgcc gtcgattagg aagccgccca agggcgacga gcaaccagat tttttcgttc   6420
cgatgctcta tgacgtgggc acccgcgata gtcgcagcat catggacgtg ccgttttcc   6480 gtctgtcgaa gcgtgaccga cgagctggcg aggtgatccg ctacgagctt ccagacgggc   6540
acgtagaggt ttccgcaggg ccggccggca tggccagtgt gtgggattac gacctggtac   6600
tgatggcggt ttcccatcta accgaatcca tgaaccgata ccgggaaggg aagggagaca   6660
agcccggccg cgtgttccgt ccacacgttg cggacgtact caagttctgc cggcgagccg   6720
atggcggaaa gcagaaagac gacctggtag aaacctgcat tcggttaaac accacgcacg   6780
ttgccatgca gcgtacgaag aaggccaaga acggccgcct ggtgacggta tccgagggtg   6840
aagccttgat tagccgctac aagatcgtaa agagcgaaac cgggcggccg gagtacatcg   6900
agatcgagct ggctgattgg atgtaccgcg agatcacaga aggcaagaac ccggacgtgc   6960
tgacggttca ccccgattac ttttttgatcg atcccggcat cggccgtttt ctctaccgcc   7020
```

```
tggcacgccg cgccgcaggc aaggcagaag ccagatggtt gttcaagacg atctacgaac    7080
gcagtggcag cgccggagag ttcaagaagt tctgtttcac cgtgcgcaag ctgatcgggt    7140
caaatgacct gccggagtac gatttgaagg aggaggcggg gcaggctggc ccgatcctag    7200
tcatgcgcta ccgcaacctg atcgagggcg aagcatccgc cggttcctaa tgtacggagc    7260
agatgctagg gcaaattgcc ctagcagggg aaaaaggtcg aaaaggtctc tttcctgtgg    7320
atagcacgta cattgggaac ccaaagccgt acattgggaa ccggaacccg tacattggga    7380
acccaaagcc gtacattggg aaccggtcac acatgtaagt gactgatata aagagaaaa    7440 aaggcgattt ttccgcctaa aactctttaa aacttattaa aactcttaaa acccgcctgg    7500
cctgtgcata actgtctggc cagcgcacag ccgaagagct gcaaaaagcg cctacccttc    7560
ggtcgctgcg ctccctacgc cccgccgctt cgcgtcggcc tatcgcggcc gctggccgct    7620
caaaaatggc tggcctacgg ccaggcaatc taccagggcg cggacaagcc gcgccgtcgc    7680
cactcgaccg ccggcgctga ggtctgcctc gtgaagaagg tgttgctgac tcataccagg    7740
cctgaatcgc cccatcatcc agccagaaag tgagggagcc acggttgatg agagctttgt    7800
tgtaggtgga ccagttggtg attttgaact tttgctttgc cacggaacgg tctgcgttgt    7860
cgggaagatg cgtgatctga tccttcaact cagcaaaagt tcgatttatt caacaaagcc    7920
gccgtcccgt caagtcagcg taatgctctg ccagtgttac aaccaattaa ccaattctga    7980
ttagaaaaac tcatcgagca tcaaatgaaa ctgcaattta ttcatatcag gattatcaat    8040
accatatttt tgaaaaagcc gtttctgtaa tgaaggagaa aactcaccga ggcagttcca    8100
taggatggca agatcctggt atcggtctgc gattccgact cgtccaacat caatacaacc    8160
tattaatttc ccctcgtcaa aaataaggtt atcaagtgag aaatcaccat gagtgacgac    8220
tgaatccggt gagaatggca aaagctctgc attaatgaat cggccaacgc gcggggagag    8280
gcggtttgcg tattgggcgc tcttccgctt cctcgctcac tgactcgctg cgctcggtcg    8340
ttcggctgcg gcgagcggta tcagctcact caaaggcggt aatacggtta tccacagaat    8400
caggggataa cgcaggaaag aacatgtgag caaaaggcca gcaaaaggcc aggaaccgta    8460
aaaaggccgc gttgctggcg ttttttccata ggctccgccc ccctgacgag catcacaaaa    8520
atcgacgctc aagtcagagg tggcgaaacc cgacaggact ataaagatac caggcgtttc    8580
cccctggaag ctccctcgtg cgctctcctg ttccgaccct gccgcttacc ggatacctgt    8640
ccgcctttct cccttcggga agcgtggcgc tttctcatag ctcacgctgt aggtatctca    8700
gttcggtgta ggtcgttcgc tccaagctgg gctgtgtgca cgaaccccccc gttcagcccg    8760 accgctgcgc cttatccggt aactatcgtc ttgagtccaa cccggtaaga cacgacttat    8820
cgccactggc agcagccact ggtaacagga ttagcagagc gaggtatgta ggcggtgcta    8880
cagagttctt gaagtggtgg cctaactacg gctacactag aagaacagta tttggtatct    8940
gcgctctgct gaagccagtt accttcggaa aaagagttgg tagctcttga tccggcaaac    9000
aaaccaccgc tggtagcggt ggtttttttg tttgcaagca gcagattacg cgcagaaaaa    9060
aaggatctca agaagatcct ttgatctttt ctacggggtc tgacgctcag tggaacgaaa    9120
actcacgtta agggattttg gtcatgagat tatcaaaaag gatcttcacc tagatccttt    9180
tgatccggaa tt                                                        9192
```

<210> SEQ ID NO 36
<211> LENGTH: 11205
<212> TYPE: DNA
<213> ORGANISM: Artificial Sequence
<220> FEATURE:
<223> OTHER INFORMATION: vector

<400> SEQUENCE: 36

```
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa tcaattgggc     300
gcgtacgtag cactagtgaa ttccggaccc aagcttgcat gcctgcagga attggccgca     360
gcggccattt aaatcaattg gcgcgtgcg gccgcagctg cttgtgggga ccagacaaaa      420
aaggaatggt gcagaattgt taggcgcacc taccaaaagc atctttgcct ttattgcaaa     480
gataaagcag attcctctag tacaagtggg gaacaaaata acgtggaaaa gagctgtcct    540
gacagcccac tcactaatgc gtatgacgaa cgcagtgacg accacaaaac tcgagacttt    600
tcaacaaagg gtaatatccg gaaacctcct cggattccat tgcccagcta tctgtcactt    660
tattgtgaag atagtggaaa aggaaggtgg ctcctacaaa tgccatcatt gcgataaagg    720
aaaggctatc gttgaagatg cctctgccga cagtggtccc aaagatggac ccccacccac   780
gaggagcatc gtggaaaaag aagacgttcc aaccacgtct tcaaagcaag tggattgatg    840
tgatatctcc actgacgtaa gggatgacga acaatcccac tatccttctg caggtcgact    900
ctagaggatc ctataatag gaagttcatt tcatttggag aggaaacctc gagtattttt     960
acaacaatta ccaacaacaa caaacaacaa acaacattac aattactatt tacaattaca    1020
catatgcctc caacaccagc tactgctact ggagctgctg ctgctgccgt tacaccagaa    1080
catgctgcaa ggtcattccc tagagttgtt cgcgttaacc ctaggtctga cagattccct    1140
gttctgtcct tccatcatgt ggagctttgg tgtgctgatg cagctagtgc tgctggtcgt    1200
ttcagctttg cacttggagc accacttgct gcaagatctg atctgtctac agggaactca    1260
gcacatgctt ctctcctact tcgatctgga gcattagcct tccttttac cgctccttat     1320
gctccacctc cacaagaagc tgcaactgct gcaactgctt ccattccctc cttttcagca    1380
gatgctgcaa gaacctttgc tgctgcacat ggacttgctg tcagatctgt tggagttagg    1440
gttgctgatg cagctgaagc atttcgcgtt agtgttgctg gaggagcaag acctgctttt    1500
gctccagcag atcttggtca cggatttgga cttgctgaag tggagctgta tggagatgtg    1560
gttctgagat tcgtgagcta tcctgacgaa actgacctac catttctccc aggattcgag    1620
agggtttcaa gtccaggtgc agttgactac ggtttgactc gctttgacca cgttgttgga    1680
aacgttccag aaatggctcc tgtcatcgac tacatgaagg gattccttgg tttccacgag    1740
ttcgctgaat tcacagcaga ggatgttgga accacagaat ctggaatgaa cagtgtggtt    1800
ctagccaaca acagtgaagc tgttcttctg ccattgaacg agcctgttca tggaaccaag    1860
agacgatctc agatccaaac ctacctcgaa taccatggtg gaccaggagt tcaacacatc    1920
gcattggctt ctaacgatgt gcttcgaact ctcagggaaa tgagagccag aactccaatg    1980
ggagggttcg aatttatggc tcctccacaa gccaagtact atgaaggagt ccgtagaatc    2040
gctggagatg tcttgtcaga ggaacagatc aaggagtgtc aagaactggg tgttatggtt    2100
gatcgagacg atcaaggtgt gctactccag atcttcacca aaccagttgg tgatcgtccc    2160
actttttcc tcgaaatgat tcagcgaata ggatgcatgg agaaggatga agttgggcaa    2220
```

```
gagtaccaga aaggtggatg tggtgggttt ggaaagggga acttttccga gttgttcaag    2280
tccatagagg actacgagaa gtcactggaa gtcaagcagt ctgtcgttgc tcagaagagc    2340
taagagctct tcatatgacg atcgttcaaa catttggcaa taaagtttct taagattgaa    2400
tcctgttgcc ggtcttgcga tgattatcat ataatttctg ttgaattacg ttaagcatgt    2460
aataattaac atgtaatgca tgacgttatt tatgagatgg gtttttatga ttagagtccc    2520
gcaattatac atttaatacg cgatagaaaa caaaatatag cgcgcaaact aggataaatt    2580
atcgcgcgcg gtgtcatcta tgttactaga tcgcggaccg aagcttgcat gcctgcaggt    2640
cgactctaga ggatctggga cccagtcaaa gattcaaata gaggacctaa cagaactcgc    2700
cgtaaagact ggcgaacagt tcatacagag tctcttacga ctcaatgaca agaagaaaat    2760
cttcgtcaac atggtggagc acgacacgct tgtctactcc aaaaatatca agatacagt    2820 ctcagaagac caaagggcaa ttgagacttt tcaacaaagg gtaatatccg gaaacctcct    2880
cggattccat tgcccagcta tctgtcactt tattgtgaag atagtggaaa aggaaggtgg    2940
ctcctacaaa tgccatcatt gcgataaagg aaaggccatc gttgaagatg cctctgccga    3000
cagtggtccc aaagatggac ccccacccac gaggagcatc gtggaaaaag aagacgttcc    3060
aaccacgtct tcaaagcaag tggattgatg tgatatctcc actgacgtaa gggatgacgc    3120
acaatcccac tatccttcgc aagacccttc ctctatataa ggaagttcat ttcatttgga    3180
gaggacacgc tgaaatcact agtccaccat gtctccggag aggagaccag ttgagattag    3240
gccagctaca gcagctgata tggccgcggt ttgtgatatc gttaaccatt acattgagac    3300
gtctacagtg aactttagga cagagccaca aacaccacaa gagtggattg atgatctaga    3360
gaggttgcaa gatagatacc cttggttggt tgctgaggtt gagggtgttg tggctggtat    3420
tgcttacgct gggccctgga aggctaggaa cgcttacgat tggacagttg agagtactgt    3480
ttacgtgtca cataggcatc aaaggttggg cctaggatcc acattgtaca cacatttgct    3540
taagtctatg gaggcgcaag gttttaagtc tgtggttgct gttataggcc ttccaaacga    3600
tccatctgtt aggttgcatg aggctttggg atacacagcc cggggtacat gcgcgcagc    3660 tggatacaag catggtggat ggcatgatgt tggttttggg caaagggatt ttgagttgcc    3720
agctcctcca aggccagtta ggccagttac ccagatctga actagtgata tcggcgccat    3780
gggtcgacct gcagatcgtt caaacatttg gcaataaagt ttcttaagat tgaatcctgt    3840
tgccggtctt gcgatgatta tcatataatt tctgttgaat tacgttaagc atgtaataat    3900
taacatgtaa tgcatgacgt tatttatgag atggggtttt atgattagag tcccgcaatt    3960
atacatttaa tacgcgatag aaaacaaaat atagcgcgca aactaggata aattatcgcg    4020
cgcggtgtca tctatgttac tagatccgga cccagctgct tgtggggacc agacaaaaaa    4080
ggaatggtgc agaattgtta ggcgcaccta ccaaaagcat ctttgccttt attgcaaaga    4140
taaagcagat tcctctagta caagtgggga acaaaataac gtggaaaaga gctgtcctga    4200
cagcccactc actaatgcgt atgacgaacg cagtgacgac cacaaaactc gagacttttc    4260
aacaaagggt aatatccgga aacctcctcg gattccattg cccagctatc tgtcacttta    4320
ttgtgaagat agtggaaaag gaaggtggct cctacaaatg ccatcattgc gataaaggaa    4380
aggctatcgt tgaagatgcc tctgccgaca gtggtcccaa agatggaccc ccacccacga    4440
ggagcatcgt ggaaaagaa gacgttccaa ccacgtcttc aaagcaagtg gattgatgtg    4500
atatctccac tgacgtaagg gatgacgaac aatcccacta tccttctgcc ggaccctcat    4560
gagcggagaa ttaagggagt cacgttatga ccccgccga tgacgcggga caagccgttt    4620
```

```
tacgtttgga actgacagaa ccgcaacgaa gctttggcag acaaagtggc agacatactg   4680
tcccacaaat gaagatggaa tctgtaaaag aaaacgcgtg aaataatgcg tctgacaaag   4740
gttaggtcgg ctgcctttaa tcaataccaa agtggtccct accacgatgg aaaaactgtg   4800
cagtcggttt ggcttttttct gacgaacaaa taagattcgt ggccgacagg tgggggtcca   4860
ccatgtgaag gcatcttcag actccaataa tggagcaatg acgtaagggc ttacgaaata   4920
agtaagggta gtttgggaaa tgtccactca cccgtcagtc tataaatact tagcccctcc   4980
ctcattgtta agggagcaaa atctcagaga gatagtccta gagagagaaa gagagcaagt   5040
agcctagaag tggatcccac catgtctccg gagaggagac cagttgagat taggccagct   5100
acagcagctg atatggccgc ggtttgtgat atcgttaacc attacattga acgtctaca    5160 gtgaacttta ggacagagcc acaaacacca caagagtgga ttgatgatct agagaggttg   5220
caagatagat acccttggtt ggttgctgag gttgagggtg ttgtggctgg tattgcttac   5280
gctgggccct ggaaggctag gaacgcttac gattggacag ttgagagtac tgtttacgtg   5340
tcacataggc atcaaaggtt gggcctagga tctacattgt acacacattt gcttaagtct   5400
atggaggcgc aaggttttaa gtctgtggtt gctgttatag gccttccaaa cgatccatct   5460
gttaggttgc atgaggcttt gggatacaca gcccgggta cattgcgcgc agctggatac    5520
aagcatggtg gatggcatga tgttggtttt tggcaaaggg attttgagtt gccagctcct   5580
ccaaggccag ttaggccagt tacccagata tgagtcgagc tctagatccc cgaatttccc   5640
cgatcgttca acatttggc aataaagttt cttaagattg aatcctgttg ccggtcttgc    5700
gatgattatc atataatttc tgttgaatta cgttaagcat gtaataatta acatgtaatg   5760
catgacgtta tttatgagat gggttttat gattagagtc ccgcaattat acatttaata    5820
cgcgatagaa aacaaaatat agcgcgcaaa ctaggataaa ttatcgcgcg cggtgtcatc   5880
tatgttacta gatcgggaat tgggtaccat gcccggcgg ccagcatggc cgtatccgca    5940
atgtgttatt aagttgtcta agcgtcaatt tgtttacacc acaatatatc ctgccaccag   6000
ccagccaaca gctccccgac cggcagctcg gcacaaaatc accactcgat acaggcagcc   6060
catcagaatt aattctcatg tttgacagct tatcatcgac tgcacggtgc accaatgctt   6120
ctggcgtcag gcagccatcg gaagctgtgg tatgctgtg caggtcgtaa atcactgcat     6180
aattcgtgtc gctcaaggcg cactcccgtt ctggataatg ttttttgcgc cgacatcata   6240
acggttctgg caaatattct gaaatgagct gttgacaatt aatcatccgg ctcgtataat   6300
gtgtggaatt gtgagcggat aacaatttca cacaggaaac agaccatgag gaagcgttg    6360 atcgccgaag tatcgactca actatcagag gtagttggcg tcatcgagcg ccatctcgaa   6420
ccgacgttgc tggccgtaca tttgtacggc tccgcagtgg atggcggcct gaagccacac   6480
agtgatattg atttgctggt tacggtgacc gtaaggcttg atgaaacaac gcggcgagct   6540
ttgatcaacg acctttggaa aacttcggct tcccctggag agagcgagat tctccgcgct   6600
gtagaagtca ccattgttgt gcacgacgac atcattccgt ggcgttatcc agctaagcgc   6660
gaactgcaat ttggagaatg gcagcgcaat gacattcttg caggtatctt cgagccagcc   6720
acgatcgaca ttgatctggc tatcttgctg acaaaagcaa gagaacatag cgttgccttg   6780
gtaggtccag cggcggagga actctttgat ccggttcctg aacaggatct atttgaggcg   6840
ctaaatgaaa ccttaacgct atggaactcg ccgcccgact gggctggcga tgagcgaaat   6900
gtagtgctta cgttgtcccg catttggtac agcgcagtaa ccggcaaaat cgcgccgaag   6960
```

```
gatgtcgctg ccgactgggc aatggagcgc ctgccggccc agtatcagcc cgtcatactt    7020
gaagctaggc aggcttatct tggacaagaa gatcgcttgg cctcgcgcgc agatcagttg    7080
gaagaatttg ttcactacgt gaaaggcgag atcaccaaag tagtcggcaa ataaagctct    7140
agtggatctc cgtacccggg gatctggctc gcggcggacg cacgacgccg gggcgagacc    7200
ataggcgatc tcctaaatca atagtagctg taacctcgaa gcgtttcact tgtaacaacg    7260
attgagaatt tttgtcataa aattgaaata cttggttcgc attttttgtca tccgcggtca    7320 gccgcaattc tgacgaactg cccatttagc tggagatgat tgtacatcct tcacgtgaaa    7380
atttctcaag cgctgtgaac aagggttcag attttagatt gaaaggtgag ccgttgaaac    7440
acgttcttct tgtcgatgac gacgtcgcta tgcggcatct tattattgaa taccttacga    7500
tccacgcctt caaagtgacc gcggtagccg acagcaccca gttcacaaga gtactctctt    7560
ccgcgacggt cgatgtcgtg gttgttgatc tagatttagg tcgtgaagat gggctcgaga    7620
tcgttcgtaa tctggcggca aagtctgata ttccaatcat aattatcagt ggcgaccgcc    7680
ttgaggagac ggataaagtt gttgcactcg agctaggagc aagtgatttt atcgctaagc    7740
cgttcagtat cagagagttt ctagcacgca ttcgggttgc cttgcgcgtg cgccccaacg    7800
ttgtccgctc caaagaccga cggtcttttt gttttactga ctggacactt aatctcaggc    7860
aacgtcgctt gatgtccgaa gctggcggtg aggtgaaact tacggcaggt gagttcaatc    7920
ttctcctcgc gttttttagag aaaccccgcg acgttctatc gcgcgagcaa cttctcattg    7980
ccagtcgagt acgcgacgag gaggtttatg acaggagtat agatgttctc attttgaggc    8040
tgcgccgcaa acttgaggca gatccgtcaa gccctcaact gataaaaaca gcaagaggtg    8100 ccggttatttt ctttgacgcg gacgtgcagg tttcgcacgg ggggacgatg gcagcctgag    8160
ccaattccca gatccccgag gaatcggcgt gagcggtcgc aaaccatccg gcccggtaca    8220
aatcggcgcg gcgctgggtg atgacctggt ggagaagttg aaggccgcgc aggccgccca    8280
gcggcaacgc atcgaggcag aagcacgccc cggtgaatcg tggcaagcgg ccgctgatcg    8340
aatccgcaaa gaatcccggc aaccgccggc agccggtgcg ccgtcgatta ggaagccgcc    8400
caagggcgac gagcaaccag atttttttcgt tccgatgctc tatgacgtgg gcacccgcga    8460
tagtcgcagc atcatggacg tggccgtttt ccgtctgtcg aagcgtgacc gacgagctgg    8520
cgaggtgatc cgctacgagc ttccagacgg gcacgtagag gttccgcag ggccggccgg    8580 catggccagt gtgtgggatt acgacctggt actgatggcg gtttcccatc taaccgaatc    8640
catgaaccga taccgggaag ggaagggaga caagcccggc cgcgtgttcc gtccacacgt    8700
tgcggacgta ctcaagttct gccggcgagc cgatggcgga aagcagaaag acgacctggt    8760
agaaacctgc attcggttaa acaccacgca cgttgccatg cagcgtacga agaaggccaa    8820
gaacggccgc ctggtgacgg tatccgaggg tgaagccttg attagccgct acaagatcgt    8880
aaagagcgaa accgggcggc cggagtacat cgagatcgag ctagctgatt ggatgtaccg    8940
cgagatcaca gaaggcaaga acccggacgt gctgacggtt caccccgatt acttttttgat    9000 cgatcccggc atcggccgtt ttctctaccg cctggcacgc cgcgccgcag gcaaggcaga    9060
agccagatgg ttgttcaaga cgatctacga acgcagtggc agcgcggag agttcaagaa    9120 gttctgtttc accgtgcgca agctgatcgg gtcaaatgac ctgccggagt acgatttgaa    9180
ggaggaggcg gggcaggctg gcccgatcct agtcatgcgc taccgcaacc tgatcgaggg    9240
cgaagcatcc gccggttcct aatgtacgga gcagatgcta gggcaaattg ccctagcagg    9300
ggaaaaaggt cgaaaaggtc tctttcctgt ggatagcacg tacattggga acccaaagcc    9360
```

```
gtacattggg aaccggaacc cgtacattgg gaacccaaag ccgtacattg ggaaccggtc    9420
acacatgtaa gtgactgata taaaagagaa aaaaggcgat ttttccgcct aaaactcttt    9480
aaaacttatt aaaactctta aaacccgcct ggcctgtgca taactgtctg gccagcgcac    9540
agccgaagag ctgcaaaaag cgcctaccct tcggtcgctg cgctccctac gccccgccgc    9600
ttcgcgtcgg cctatcgcgg ccgctggccg ctcaaaaatg gctggcctac ggccaggcaa    9660
tctaccaggg cgcggacaag ccgcgccgtc gccactcgac cgccggcgct gaggtctgcc    9720
tcgtgaagaa ggtgttgctg actcatacca ggcctgaatc gccccatcat ccagccagaa    9780
agtgagggag ccacggttga tgagagcttt gttgtaggtg gaccagttgg tgattttgaa    9840
cttttgcttt gccacggaac ggtctgcgtt gtcgggaaga tgcgtgatct gatccttcaa    9900
ctcagcaaaa gttcgattta ttcaacaaag ccgccgtccc gtcaagtcag cgtaatgctc    9960
tgccagtgtt acaaccaatt aaccaattct gattagaaaa actcatcgag catcaaatga   10020
aactgcaatt tattcatatc aggattatca ataccatatt tttgaaaaag ccgtttctgt   10080
aatgaaggag aaaactcacc gaggcagttc cataggatgg caagatcctg gtatcggtct   10140
gcgattccga ctcgtccaac atcaatacaa cctattaatt tcccctcgtc aaaaataagg   10200
ttatcaagtg agaaatcacc atgagtgacg actgaatccg gtgagaatgg caaaagctct   10260
gcattaatga atcggccaac gcgcggggag aggcggtttg cgtattgggc gctcttccgc   10320
ttcctcgctc actgactcgc tgcgctcggt cgttcggctg cggcgagcgg tatcagctca   10380
ctcaaaggcg gtaatacggt tatccacaga atcaggggat aacgcaggaa agaacatgtg   10440
agcaaaaggc cagcaaaagg ccaggaaccg taaaaaggcc gcgttgctgg cgttttttcca   10500 taggctccgc cccctgacg agcatcacaa aaatcgacg caagtcaga ggtggcgaaa   10560 cccgacagga ctataaagat accaggcgtt tccccctgga agctccctcg tgcgctctcc   10620
tgttccgacc ctgccgctta ccggatacct gtccgccttt ctcccttcgg aagcgtggc   10680 gctttctcat agctcacgct gtaggtatct cagttcggtg taggtcgttc gctccaagct   10740
gggctgtgtg cacgaacccc ccgttcagcc cgaccgctgc gccttatccg gtaactatcg   10800
tcttgagtcc aacccggtaa gacacgactt atcgccactg gcagcagcca ctggtaacag   10860
gattagcaga gcgaggtatg taggcggtgc tacagagttc ttgaagtggt ggcctaacta   10920
cggctacact agaagaacag tatttggtat ctgcgctctg ctgaagccag ttaccttcgg   10980
aaaaagagtt ggtagctctt gatccggcaa acaaaccacc gctggtagcg gtggtttttt   11040
tgtttgcaag cagcagatta cgcgcagaaa aaaaggatct caagaagatc ctttgatctt   11100
ttctacgggg tctgacgctc agtggaacga aaactcacgt taagggattt tggtcatgag   11160
attatcaaaa aggatcttca cctagatcct tttgatccgg aatta                  11205
```

<210> SEQ ID NO 37
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 37

Glu Val Glu Leu Tyr Gly Asp Val Val
1               5

<210> SEQ ID NO 38
<211> LENGTH: 9

```
<212> TYPE: PRT
<213> ORGANISM: Artificial Sequence
<220> FEATURE:
<223> OTHER INFORMATION: sequence motif from Avena sativa derived HPPD

<400> SEQUENCE: 38

Arg Phe Asp His Val Val Gly Asn Val
1               5

<210> SEQ ID NO 39
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 39

Asp His Val Val Gly Asn Val Pro Glu
1               5

<210> SEQ ID NO 40
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 40

His Val Val Gly Asn Val Pro Glu Met
1               5

<210> SEQ ID NO 41
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 41

Asn Val Pro Glu Met Ala Pro Val Ile
1               5

<210> SEQ ID NO 42
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 42

Gly Phe His Glu Phe Ala Glu Phe Thr
1               5

<210> SEQ ID NO 43
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 43

Gly Thr Thr Glu Ser Gly Leu Asn Ser
1               5

<210> SEQ ID NO 44
<211> LENGTH: 9
<212> TYPE: PRT
```

```
<213> ORGANISM: Artificial Sequence
<220> FEATURE:
<223> OTHER INFORMATION: sequence motif from Avena sativa derived HPPD

<400> SEQUENCE: 44

Thr Thr Glu Ser Gly Leu Asn Ser Val
1               5

<210> SEQ ID NO 45
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 45

Glu Ser Gly Leu Asn Ser Val Val Leu
1               5

<210> SEQ ID NO 46
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 46

Gly Leu Asn Ser Val Val Leu Ala Asn
1               5

<210> SEQ ID NO 47
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 47

Leu Asn Ser Val Val Leu Ala Asn Asn
1               5

<210> SEQ ID NO 48
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 48

Ser Glu Ala Val Leu Leu Pro Leu Asn
1               5

<210> SEQ ID NO 49
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 49

Glu Ala Val Leu Leu Pro Leu Asn Glu
1               5

<210> SEQ ID NO 50
<211> LENGTH: 9
<212> TYPE: PRT
<213> ORGANISM: Artificial Sequence
```

```
<220> FEATURE:
<223> OTHER INFORMATION: sequence motif from Avena sativa derived HPPD

<400> SEQUENCE: 50

Val Leu Leu Pro Leu Asn Glu Pro Val
1               5

<210> SEQ ID NO 51
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 51

Leu Leu Pro Leu Asn Glu Pro Val His
1               5

<210> SEQ ID NO 52
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 52

His Gly Thr Lys Arg Arg Ser Gln Ile
1               5

<210> SEQ ID NO 53
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 53

Ser Gln Ile Gln Thr Tyr Leu Glu Tyr
1               5

<210> SEQ ID NO 54
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 54

Gln Ile Gln Thr Tyr Leu Glu Tyr His
1               5

<210> SEQ ID NO 55
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 55

Gly Val Gln His Ile Ala Leu Ala Ser
1               5

<210> SEQ ID NO 56
<211> LENGTH: 10
<212> TYPE: PRT
<213> ORGANISM: Artificial Sequence
<220> FEATURE:
```

```
<223> OTHER INFORMATION: sequence motif from Avena sativa derived HPPD

<400> SEQUENCE: 56

Lys Gly Asn Phe Ser Glu Leu Phe Lys Ser
1               5                   10

<210> SEQ ID NO 57
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 57

Gly Phe Glu Phe Met Ala Pro Pro Gln
1               5

<210> SEQ ID NO 58
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 58

Phe Glu Phe Met Ala Pro Pro Gln Ala
1               5

<210> SEQ ID NO 59
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 59

Phe Met Ala Pro Pro Gln Ala Lys Tyr
1               5

<210> SEQ ID NO 60
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 60

Gln Ala Lys Tyr Tyr Glu Gly Val Arg
1               5

<210> SEQ ID NO 61
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 61

Gly Val Arg Arg Ile Ala Gly Asp Val
1               5

<210> SEQ ID NO 62
<211> LENGTH: 9
<212> TYPE: PRT
<213> ORGANISM: Artificial Sequence
<220> FEATURE:
<223> OTHER INFORMATION: sequence motif from Avena sativa derived HPPD
```

```
<400> SEQUENCE: 62

Val Leu Leu Gln Ile Phe Thr Lys Pro
1               5

<210> SEQ ID NO 63
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 63

Leu Leu Gln Ile Phe Thr Lys Pro Val
1               5

<210> SEQ ID NO 64
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 64

Leu Gln Ile Phe Thr Lys Pro Val Gly
1               5

<210> SEQ ID NO 65
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 65

Ile Phe Thr Lys Pro Val Gly Asp Arg
1               5

<210> SEQ ID NO 66
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 66

Arg Pro Thr Phe Phe Leu Glu Met Ile
1               5

<210> SEQ ID NO 67
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 67

Phe Leu Glu Met Ile Gln Arg Ile Gly
1               5

<210> SEQ ID NO 68
<211> LENGTH: 9
<212> TYPE: PRT
<213> ORGANISM: Artificial Sequence
<220> FEATURE:
<223> OTHER INFORMATION: sequence motif from Avena sativa derived HPPD
```

```
<400> SEQUENCE: 68

Gly Gly Cys Gly Gly Phe Gly Lys Gly
1               5

<210> SEQ ID NO 69
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 69

Gly Gly Phe Gly Lys Gly Asn Phe Ser
1               5

<210> SEQ ID NO 70
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 70

Gly Phe Gly Lys Gly Asn Phe Ser Glu
1               5

<210> SEQ ID NO 71
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 71

Phe Gly Lys Gly Asn Phe Ser Glu Leu
1               5

<210> SEQ ID NO 72
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 72

Lys Gly Asn Phe Ser Glu Leu Phe Lys
1               5

<210> SEQ ID NO 73
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 73

Gly Asn Phe Ser Glu Leu Phe Lys Ser
1               5

<210> SEQ ID NO 74
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 74
```

```
Glu Leu Phe Lys Ser Ile Glu Asp Tyr
1               5

<210> SEQ ID NO 75
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 75

Leu Phe Lys Ser Ile Glu Asp Tyr Glu
1               5

<210> SEQ ID NO 76
<211> LENGTH: 11
<212> TYPE: PRT
<213> ORGANISM: Artificial Sequence
<220> FEATURE:
<223> OTHER INFORMATION: sequence motif from Avena sativa derived HPPD

<400> SEQUENCE: 76

Phe His Glu Phe Ala Glu Phe Thr Ala Glu Asp
1               5                   10

<210> SEQ ID NO 77
<211> LENGTH: 10
<212> TYPE: PRT
<213> ORGANISM: Artificial Sequence
<220> FEATURE:
<223> OTHER INFORMATION: sequence motif from Avena sativa derived HPPD

<400> SEQUENCE: 77

His Gly Thr Lys Arg Arg Ser Gln Ile Gln
1               5                   10

<210> SEQ ID NO 78
<211> LENGTH: 9
<212> TYPE: PRT
<213> ORGANISM: Artificial Sequence
<220> FEATURE:
<223> OTHER INFORMATION: sequence motif from Avena sativa derived HPPD

<400> SEQUENCE: 78

Gly Thr Lys Arg Arg Ser Gln Ile Gln
1               5

<210> SEQ ID NO 79
<211> LENGTH: 12
<212> TYPE: PRT
<213> ORGANISM: Artificial Sequence
<220> FEATURE:
<223> OTHER INFORMATION: sequence motif from Avena sativa derived HPPD

<400> SEQUENCE: 79

Asp Gln Gly Val Leu Leu Gln Ile Phe Thr Lys Pro
1               5                   10

<210> SEQ ID NO 80
<211> LENGTH: 10
<212> TYPE: PRT
<213> ORGANISM: Artificial Sequence
<220> FEATURE:
<223> OTHER INFORMATION: sequence motif from Avena sativa derived HPPD

<400> SEQUENCE: 80
```

```
Gly Lys Gly Asn Phe Ser Glu Leu Phe Lys
1               5                   10
```

MUTANT HYDROXYPHENYLPYRUVATE DIOXYGENASE POLYPEPTIDES AND METHODS OF USE

CROSS-REFERENCE TO RELATED APPLICATIONS

This application is a divisional of U.S. patent application Ser. No. 12/692,552, now issued as U.S. Pat. No. 8,269,068, filed on Jan. 22, 2010, which claims priority to U.S. Provisional Patent Application No. 61/224,661, filed on Jul. 10, 2009 and U.S. Provisional Patent Application No. 61/146,513, filed on Jan. 22, 2009.

FIELD OF THE INVENTION

The present invention relates to mutant hydroxyphenyl pyruvate dioxygenase (HPPD) polypeptides that confer herbicide resistance or tolerance to plants and the nucleic acid sequences that encode them. Methods of the invention relate to the production and use of plants that express these mutant HPPD polypeptides and that are resistant to HPPD herbicides.

BACKGROUND OF THE INVENTION

The hydroxyphenylpyruvate dioxygenases (HPPDs) are enzymes that catalyze the reaction in which para-hydroxyphenylpyruvate (HPP) is transformed into homogentisate. This reaction takes place in the presence of enzyme-bound iron ($Fe^{2+}$) and oxygen. Herbicides that act by inhibiting HPPD are well known, and include isoxazoles, diketonitriles, triketones, and pyrazolinates (Hawkes "Hydroxyphenylpyruvate Dioxygenase (HPPD)—The Herbicide Target." In *Modern Crop Protection Compounds*. Eds. Krämer and Schirmer. Weinheim, Germany: Wiley-VCH, 2007. Ch. 4.2, pp. 211-220). Inhibition of HPPD blocks the biosynthesis of plastoquinone (PQ) from tyrosine. PQ is an essential cofactor in the biosynthesis of carotenoid pigments which are essential for photoprotection of the photosynthetic centres. HPPD-inhibiting herbicides are phloem-mobile bleachers which cause the light-exposed new meristems and leaves to emerge white. In the absence of carotenoids, chlorophyll is photo-destroyed and becomes itself an agent of photo-destruction via the photo-generation of singlet oxygen.

Methods are also known for providing plants that are tolerant to HPPD herbicides and have included: 1) overexpressing the HPPD enzyme so as to produce quantities of HPPD enzyme in the plant that are sufficient in relation to a given herbicide so as to have enough of the functional enzyme available despite the presence of its inhibitor; and 2) mutating the target HPPD enzyme into a functional HPPD that is less sensitive to herbicides. With respect to mutant HPPDs, while a given mutant HPPD enzyme may provide a useful level of tolerance to some HPPD-inhibitor herbicides, the same mutant HPPD may be quite inadequate to provide commercial levels of tolerance to a different, more desirable HPPD-inhibitor herbicide (See, e.g., U.S. App. Pub. No. 2004/0058427; and PCT App. Pub. Nos. WO 98/20144 and WO 02/46387; see also U.S. App. Pub. No. 2005/0246800 relating to identification and labelling of soybean varieties as being relatively HPPD tolerant). For example, HPPD-inhibitor herbicides may differ in terms of the spectrum of weeds they control, their manufacturing cost, and their environmental benefits.

Accordingly, new methods and compositions for conferring HPPD herbicide tolerance upon various crops and crop varieties are needed.

SUMMARY OF THE INVENTION

Compositions and methods for conferring hydroxyphenyl pyruvate dioxygenase (HPPD) herbicide resistance or tolerance to plants are provided. The compositions include nucleotide and amino acid sequences for mutant HPPD polypeptides. The polypeptides of the invention are mutant HPPDs that have HPPD enzymatic activity and that confer resistance or tolerance in plants to certain classes of herbicides that inhibit HPPD. In one embodiment, the compositions of the invention comprise a mutant HPPD polypeptide having at least 80% sequence identity to SEQ ID NO:27, where the polypeptide has HPPD enzymatic activity, and where the polypeptide contains one or more amino acid additions, substitutions, or deletions selected from the group consisting of:

1) R(K,A,R)SQI(Q,E)T (SEQ ID NO:28), wherein the first Q is replaced with any other amino acid, particularly with A, G, M, T, S, C, R, F and more particularly with P;

2) R(K,A,R)SQI(Q,E)T (SEQ ID NO:28), wherein I is replaced with any other amino acid, particularly with V, S, A, P, T, L or G;

3) (P,A,S)G(V,L)QH(I,L,M) (SEQ ID NO:29), wherein Q is replaced with any other amino acid, particularly with N, R, G, A, S, T, E or C, and more particularly with A or H;

4) G(I,V) LVD(R,K)D (SEQ ID NO:30), wherein L is replaced with any other amino acid, particularly with M or A;

5) ESGLN(S,G) (SEQ ID NO:31), wherein L is replaced with any other amino acid, particularly with M, H, G, F, C or I, and more particularly with M;

6) F(A,S)EF(T,V) (SEQ ID NO:32), wherein (A,S) is replaced with any amino acid, particularly with W, G, M, F, Y or H;

7) G(I,V) LVD(R,K)D (SEQ ID NO:30) and ESGLN(S,G) (SEQ ID NO:31), where L in both sequences is replaced with M;

8) EVELYGDVV (SEQ ID NO:37), wherein Y is replaced with any other amino acid, particularly with D, V, E, K, or A;

9) RFDHVVGNV (SEQ ID NO:38), wherein the first V is replaced with any other amino acid; such as I, A, M, or C;

10) DHVVGNVPE (SEQ ID NO:39), wherein G is replaced with any other amino acid; such as H or C;

11) HVVGNVPEM (SEQ ID NO:40), wherein N is replaced with any other amino acid; such as C;

12) NVPEMAPVI (SEQ ID NO:41), wherein M is replaced with any other amino acid; such as L;

13) GFHEFAEFT (SEQ ID NO:42), wherein F is replaced with any other amino acid; such as M, I, or L;

14) GTTESGLNS (SEQ ID NO:43), wherein S is replaced with any other amino acid; such as T;

15) TTESGLNSV (SEQ ID NO:44), wherein G is replaced with any other amino acid; such as R, S, or A;

16) ESGLNSVVL (SEQ ID NO:45), wherein N is replaced with any other amino acid; such as R or M;

17) GLNSVVLAN (SEQ ID NO:46), wherein the first V is replaced with any other amino acid; such as M, I, A, or K;

18) LNSVVLANN (SEQ ID NO:47), wherein V is replaced with any other amino acid; such as I;

19) SEAVLLPLN (SEQ ID NO:48), wherein L is replaced with any other amino acid; such as V or K;

20) EAVLLPLNE (SEQ ID NO:49), wherein L is replaced with any other amino acid; such as M or F;

21) VLLPLNEPV (SEQ ID NO:50), wherein the third L is replaced with any other amino acid; such as I, M, or V;

22) LLPLNEPVH (SEQ ID NO:51), wherein N is replaced with any other amino acid; such as A;
23) HGTKRRSQI (SEQ ID NO:52), wherein R is replaced with any other amino acid; such as G;
24) SQIQTYLEY (SEQ ID NO:53), wherein T is replaced with any other amino acid; such as E;
25) QIQTYLEYH (SEQ ID NO:54), wherein Y is replaced with any other amino acid; such as F;
26) GVQHIALAS (SEQ ID NO:55), wherein I is replaced with any other amino acid; such as M, L, or V;
27) GFEFMAPPQ (SEQ ID NO:57), wherein M is replaced with any other amino acid; such as Q or L;
28) FEFMAPPQA (SEQ ID NO:58), wherein the first A is replaced with any other amino acid; such as S, P, D, R, N, Y, K, or H;
29) FMAPPQAKY (SEQ ID NO:59), wherein P is replaced with any other amino acid; such as A or R;
30) QAKYYEGVR (SEQ ID NO:60), wherein Y is replaced with any other amino acid; such as K, R, D, Q, or E;
31) GVRRIAGDV (SEQ ID NO:61), wherein I is replaced with any other amino acid; such as R or L;
32) VLLQIFTKP (SEQ ID NO:62), wherein I is replaced with any other amino acid; such as V;
33) LLQIFTKPV (SEQ ID NO:63), wherein F is replaced with any other amino acid; such as L;
34) LQIFTKPVG (SEQ ID NO:64), wherein T is replaced with any other amino acid; such as S, P, D, R, N, Y, or H;
35) IFTKPVGDR (SEQ ID NO:65), wherein P is replaced with any other amino acid; such as N;
36) RPTFFLEMI (SEQ ID NO:66), wherein F is replaced with any other amino acid; such as L;
37) FLEMIQRIG (SEQ ID NO:67), wherein I is replaced with any other amino acid; such as V or C;
38) GGCGGFGKG (SEQ ID NO:68), wherein the fourth G is replaced with any other amino acid; such as A, S, or T;
39) GGFGKGNFS (SEQ ID NO:69), wherein K is replaced with any other amino acid; such as L, A, E, or V;
40) GFGKGNFSE (SEQ ID NO:70), wherein G is replaced with any other amino acid; such as I;
41) FGKGNFSEL (SEQ ID NO:71), wherein N is replaced with any other amino acid; such as I;
42) KGNFSELFK (SEQ ID NO:72), wherein S is replaced with any other amino acid; such as N, G, K, or Q;
43) GNFSELFKS (SEQ ID NO:73), wherein E is replaced with any other amino acid; such as Q;
44) ELFKSIEDY (SEQ ID NO:74), wherein S is replaced with any other amino acid; such as A;
45) LFKSIEDYE (SEQ ID NO:75), wherein I is replaced with any other amino acid; such as L or F;
46) HVVGNVPEM (SEQ ID NO:40), wherein N is replaced with any other amino acid, particularly a C, and the amino acid sequence ELGVLVDRD (SEQ ID NO:76), wherein the second L is replaced with any other amino acid, particularly an M;
47) LNSVVLANN (SEQ ID NO:47), wherein the second V is replaced with any other amino acid, particularly an I, and the amino acid sequence ELGVLVDRD (SEQ ID NO:76), wherein the second L is replaced with any other amino acid, particularly an M;
48) VLLPLNEPV (SEQ ID NO:50), wherein the third L is replaced with any other amino acid, particularly an M, and the amino acid sequence VLLQIFTKP (SEQ ID NO:62), wherein I is replaced with any other amino acid, particularly a V;
49) GGCGGFGKG (SEQ ID NO:68), wherein the fourth G is replaced with any other amino acid, particularly a T, and the amino acid sequence ELGVLVDRD (SEQ ID NO:76), wherein the second L is replaced with any other amino acid, particularly an M;
50) FHEFAEFTAED (SEQ ID NO:76), wherein the first A, the second E, and the second F are replaced with any other amino acid, particularly where the A is replaced with an S or a W, the E is replaced with a T, and/or the F is replaced with an A or a V;
51) HGTKRRSQIQ (SEQ ID NO:77), wherein the first R is replaced with any other amino acid, particularly with a K, and the second R is deleted;
52) GTKRRSQIQ (SEQ ID NO:78), wherein the second R is deleted;
53) FMAPPQAKY (SEQ ID NO:59), wherein the second P is deleted;
54) GNFSELFKS (SEQ ID NO:73), wherein the E is deleted;
55) GVRRIAGDV (SEQ ID NO:61), wherein the I is deleted;
56) DQGVLLQIFTKP (SEQ ID NO:79), wherein the first L and the I are replaced with any other amino acid, particularly where the A is replaced with an M and/or the I is replaced with an L;
57) GKGNFSELFK (SEQ ID NO:80), wherein the F and the S are replaced with any other amino acid, particularly where the F is replaced with a G and/or the S is replaced with an A;
58) KGNFSELFKS (SEQ ID NO:56), wherein the first S and the E are replaced with any other amino acid, particularly where the S is replaced with an N, G, or K and/or the E is replaced with an S or an A;
59) GGCGGFGKG (SEQ ID NO:68) wherein the K is replaced with any other amino acid, such as T, S, Q, L, A, I, H, E, G, M, C or V, preferably T;
60) GGCGGFGKG (SEQ ID NO:68), wherein the sixth G is replaced with any other amino acid, such as R, E, D, H, M, F, W, N, or C, preferably H or C;
61) ESGLN(S,G) (SEQ ID NO:31), wherein the first G is replaced with any other amino acid, particularly with R, S, or A; and
62) VLLPLNEPV (SEQ ID NO:50), wherein the second L is replaced with any other amino acid, such as M, F, or V.

In another embodiment, the compositions of the invention comprise a mutant HPPD polypeptide having at least 80% sequence identity to SEQ ID NO:14 or to SEQ ID NO:27, where the polypeptide has HPPD enzymatic activity, and where the polypeptide contains one or more amino acid substitutions selected from the group consisting of:
1) R(K,A,R)SQI(Q,E)T (SEQ ID NO:28), wherein I is replaced with any other amino acid, particularly with V, S, A, P, T, L or G;
2) (P,A,S)G(V,L)QH(I,L,M) (SEQ ID NO:29), wherein Q is replaced with any other amino acid, particularly with N, R, G, A, S, T, E or C, and more particularly with A or H;
3) G(I,V) LVD(R,K)D (SEQ ID NO:30), wherein L is replaced with any other amino acid, particularly with M or A;
4) ESGLN(S,G) (SEQ ID NO:31), wherein L is replaced with any other amino acid, particularly with M, H, G, F, C or I, and more particularly with M;
5) F(A,S)EF(T,V) (SEQ ID NO:32), wherein (A,S) is replaced with any amino acid, particularly with W, G, M, F, Y or H;
6) RFDHVVGNV (SEQ ID NO:38), wherein the first V is replaced with any other amino acid, such as I, A, M, or C;
7) GLNSVVLAN (SEQ ID NO:46), wherein the first V is replaced with any other amino acid, such as M, I, A, or K;

8) VLLPLNEPV (SEQ ID NO:50), wherein the third L is replaced with any other amino acid, such as I, M, or V;

9) GFEFMAPPQ (SEQ ID NO:57), wherein M is replaced with any other amino acid, such as Q or L;

10) FEFMAPPQA (SEQ ID NO:58), wherein the first A is replaced with any other amino acid, such as S, P, D, R, N, Y, K, or H;

11) GGCGGFGKG (SEQ ID NO:68), wherein the fourth G is replaced with any other amino acid, such as A, S, or T;

12) GGCGGFGKG (SEQ ID NO:68) wherein the K is replaced with any other amino acid, such as T, S, Q, L, A, I, H, E, G, M, C or V, preferably T;

13) GGCGGFGKG (SEQ ID NO:68), wherein the sixth G is replaced with any other amino acid, such as R, E, D, H, M, F, W, N, or C, preferably H or C;

14) ESGLN(S,G) (SEQ ID NO:31), wherein the first G is replaced with any other amino acid, particularly with R, S, or A; and 15) VLLPLNEPV (SEQ ID NO:50), wherein the second L is replaced with any other amino acid, such as M, F, or V.

Exemplary mutant HPPD polypeptides according to the invention correspond to the amino acid sequences set forth in SEQ ID NOS:14-26, and variants and fragments thereof. Nucleic acid molecules comprising polynucleotide sequences that encode the mutant HPPD polypeptides of the invention are further provided, e.g., SEQ ID NOS:1-13. Compositions also include expression cassettes comprising a promoter operably linked to a nucleotide sequence that encodes a mutant HPPD polypeptide of the invention, alone or in combination with one or more additional nucleic acid molecules encoding polypeptides that confer desirable traits. Transformed plants, plant cells, and seeds comprising an expression cassette of the invention are further provided.

The compositions of the invention are useful in methods directed to conferring herbicide resistance or tolerance to plants, particularly resistance or tolerance to certain classes of herbicides that inhibit HPPD. In particular embodiments, the methods comprise introducing into a plant at least one expression cassette comprising a promoter operably linked to a nucleotide sequence that encodes a mutant HPPD polypeptide of the invention. As a result, the mutant HPPD polypeptide is expressed in the plant, and the mutant HPPD is less sensitive to HPPD-inhibiting herbicides, thereby leading to resistance or tolerance to HPPD-inhibiting herbicides.

Methods of the present invention also comprise selectively controlling weeds in a field at a crop locus. In one embodiment, such methods involve over-the-top pre- or postemergence application of weed-controlling amounts of HPPD herbicides in a field at a crop locus that contains plants expressing the mutant HPPD polypeptides of the invention. In other embodiments, methods are also provided for the assay, characterization, identification, and selection of the mutant HPPDs of the current invention.

DETAILED DESCRIPTION OF THE INVENTION

Figure 1:
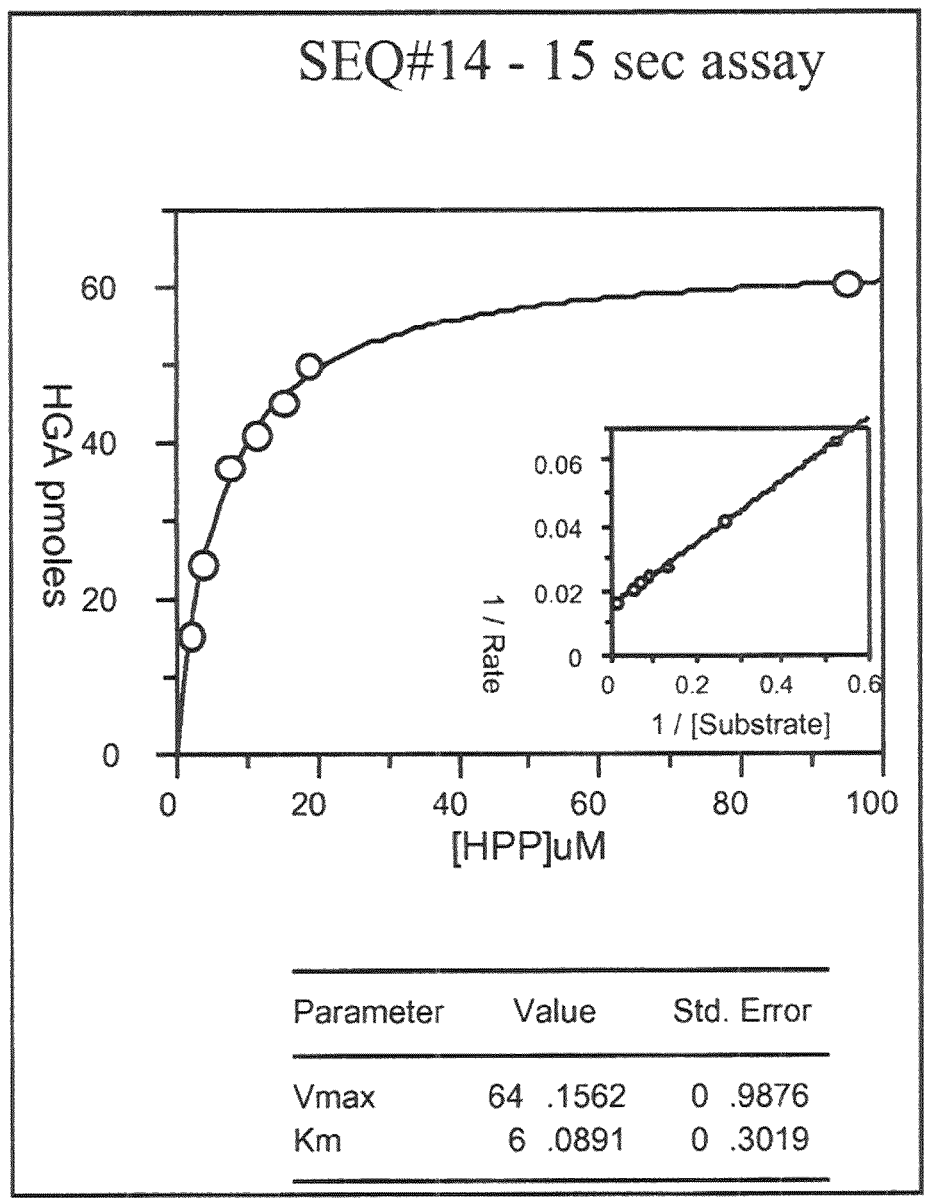
FIG. 1 shows Km and Vmax values of the *Avena*-derived HPPD polypeptide corresponding to the amino acid sequence set forth in SEQ ID NO:14.

The present invention provides compositions and methods directed to conferring hydroxyphenyl pyruvate dioxygenase (HPPD) herbicide resistance or tolerance to plants. Compositions include amino acid sequences for mutant HPPD polypeptides having HPPD enzymatic activity, and variants and fragments thereof. Nucleic acids that encode the mutant HPPD polypeptides of the invention are also provided. Methods for conferring herbicide resistance or tolerance to plants, particularly resistance or tolerance to certain classes of herbicides that inhibit HPPD, are further provided. Methods are also provided for selectively controlling weeds in a field at a crop locus and for the assay, characterization, identification and selection of the mutant HPPDs of the current invention that provide herbicide tolerance.

Within the context of the present invention the terms hydroxy phenyl pyruvate dioxygenase (HPPD), 4-hydroxy phenyl pyruvate dioxygenase (4-HPPD) and p-hydroxy phenyl pyruvate dioxygenase (p-HPPD) are synonymous.

"HPPD herbicides" are herbicides that are bleachers and whose primary site of action is HPPD. Many are well known and described elsewhere herein and in the literature (Hawkes "Hydroxyphenylpyruvate Dioxygenase (HPPD)—The Herbicide Target." In *Modern Crop Protection Compounds*. Eds. Krämer and Schirmer. Weinheim, Germany: Wiley-VCH, 2007. Ch. 4.2, pp. 211-220; Edmunds "Hydroxyphenylpyruvate dioxygenase (HPPD) Inhibitors: Triketones." In *Modern Crop Protection Compounds*. Eds. Krämer and Schirmer. Weinheim, Germany: Wiley-VCH, 2007. Ch. 4.2, pp. 221-242). As used herein, the term "HPPD herbicides" refers to herbicides that act either directly or indirectly to inhibit HPPD, where the herbicides are bleachers, and where inhibition of HPPD is at least part of the herbicide's mode of action on plants.

As used herein, plants which are substantially "tolerant" to a herbicide exhibit, when treated with said herbicide, a dose/response curve which is shifted to the right when compared with that exhibited by similarly subjected non tolerant like plants. Such dose/response curves have "dose" plotted on the x-axis and "percentage kill or damage", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions or, at least, none that impact significantly on yield, when subjected to the herbicide at concentrations and rates which are typically employed by the agricultural community to kill weeds in the field.

As used herein, "non-transgenic-like plants" are plants that are similar or the same as transgenic plants but that do not contain a transgene conferring herbicide resistance.

As used herein, the term "confer" refers to providing a characteristic or trait, such as herbicide tolerance or resistance and/or other desirable traits to a plant.

As described elsewhere herein, the term "heterologous" means from another source. In the context of DNA, "heterologous" refers to any foreign "non-self" DNA including that from another plant of the same species. For example, in the present application a soybean HPPD gene that was transgenically expressed back into a soybean plant would still be described as "heterologous" DNA.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

A variety of additional terms are defined or otherwise characterized herein.

HPPD Sequences

The compositions of the invention include isolated or substantially purified mutant HPPD polynucleotides and polypeptides as well as host cells comprising mutant HPPD polynucleotides. Specifically, the present invention provides mutant HPPD polypeptides that have HPPD enzymatic activity and that confer resistance or tolerance in plants to certain classes of herbicides that inhibit HPPD, and variants and fragments thereof. Nucleic acids that encode the mutant HPPD polypeptides of the invention are also provided.

Mutant HPPD polypeptides of the presenting invention have amino acid changes at one or more positions relative to the starting wild type sequence from which they are derived, and exhibit enhanced tolerance to one or more HPPD inhibitor herbicides. HPPD enzymes that exhibit enhanced tolerance to an HPPD herbicide may do so by virtue of exhibiting, relative to the like unmutated starting enzyme:

a) a lower Km value for the natural substrate, 4-hydroxyphenylpyruvate;

b) a higher kcat value for converting 4-hydroxyphenylpyruvate to homogentisate;

c) a lower value of the rate constant, kon, governing formation of an enzyme: HPPD inhibitor herbicide complex;

d) an increased value of the rate constant, koff, governing dissociation of an enzyme: HPPD inhibitor herbicide complex; and/or e) as a result of changes in one or both of c) and d), an increased value of the equilibrium constant, Ki (also called Kd), governing dissociation of an enzyme: HPPD inhibitor herbicide complex. DNA sequences encoding such improved mutated HPPDs are used in the provision of HPPD plants, crops, plant cells and seeds of the current invention that offer enhanced tolerance or resistance to one or more HPPD herbicides as compared to like plants likewise expressing the unmutated starting enzyme.

Increases in the value of koff are of particular value in improving the ability of HPPD to confer resistance to a HPPD herbicide. As one example, compounds B and C exhibit similar Kd values with respect to the HPPD variant of SEQ ID NO:14 but differ in that the koff value for compound B is about 10-fold greater as compared to the koff value for compound C, and plants expressing SEQ ID NO:14 show superior resistance to compound B than to compound C.

Site-directed mutations of genes encoding plant-derived HPPDs are selected so as to encode amino acid changes selected from the list below either singly or in combination. Genes encoding such mutant forms of plant HPPDs are useful for making crop plants resistant to herbicides that inhibit HPPD. Plant HPPD genes so modified are especially suitable for use in transgenic plants in order to confer herbicide tolerance or resistance upon crop plants.

Many HPPD sequences are known in the art and can be used to generate mutant HPPD sequences by making the corresponding amino acid substitutions, deletions, and additions described herein. The HPPD amino acid sequence of *Avena sativa* is set forth in SEQ ID NO:27. A single deletion variant of the *Avena sativa* HPPD is set forth in SEQ ID NO:14. Thus, a known or suspected HPPD sequence can be aligned with, for example, SEQ ID NO:14 or SEQ ID NO:27 using standard sequence alignment tools, and the corresponding amino acid substitutions, deletions, and/or additions described herein with respect to SEQ ID NO:14 or to SEQ ID NO:27 can be made in the reference sequence.

In one embodiment, the compositions of the invention comprise a mutant HPPD polypeptide having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO:27 (the HPPD amino acid sequence of *Avena sativa*) or where the HPPD amino acid sequence derives from a plant, where the polypeptide has HPPD enzymatic activity, and where the polypeptide contains one or more amino acid sequence additions, substitutions, or deletions corresponding to the amino acid positions listed in column 1 of Table 1, optionally in further combination with known mutations (see e.g., WO2009/144079). In various embodiments, an amino acid at one or more position(s) listed in column 1 of Table 1 is replaced with any other amino acid. In another embodiment, the polypeptide comprises one or more amino acid substitutions, additions, or deletions corresponding to the amino acid substitutions or additions listed in column 2 of Table 1. In yet another embodiment, the polypeptide comprises one or more substitutions corresponding to a conservative variant of the amino acids listed in column 2 of Table 1. For example, the polypeptide may comprise a mutation corresponding to amino acid position 217 of SEQ ID NO:14 (amino acid position 218 of SEQ ID NO:27), wherein that amino acid is replaced with alanine or a conservative substitution of alanine; or the polypeptide may comprise a mutation corresponding to amino acid position 241 of SEQ ID NO:14 (amino acid position 242 of SEQ ID NO:27), wherein that amino acid is replaced with tryptophan or a conservative substitution of tryptophan; or the polypeptide may comprise a mutation corresponding to amino acid position 408 of SEQ ID NO:14 (amino acid position 409 of SEQ ID NO:27), wherein that amino acid is replaced with alanine or a conservative substitution of alanine. In particular embodiments, the amino acid sequence of the mutant HPPD polypeptide of the invention is selected from the group consisting of SEQ ID NO:14, 15, 16, 17, 18, 19, 20, 21, 22, 23, 24, 25, and 26.

TABLE 1

Exemplary HPPD Mutations

| Mutable amino acid position relative to SEQ ID NO: 14 | Substitution, addition, or deletion* |
|---|---|
| 172 | D, V, E, K, or A |
| 217 | I, A, M, or C |
| 219 | H or C |
| 220 | C |
| 224 | L |
| 240 | M, I, or L |
| 241 | S, W, G, M, F, Y, or H |
| 244 | V |
| 253 | T |
| 254 | R, S, or A |
| 255 | M, H, G, F, C, or I |
| 256 | R or M |
| 257 | G |
| 258 | M, I, A, or K |
| 259 | I |
| 268 | V or K |
| 269 | M, F, or V |
| 271 | I, M, or V |
| 272 | A |
| 280 | G or K |
| 281 | Delete R |
| 281-282 | insert K, A, or R between R282 and S283 |
| 284 | V, S, A, P, T, L, or G |
| 286 | E |
| 287 | F |
| 294 | A or S |
| 296 | L |
| 297 | N, R, G, A, H, S, T, E, or C |
| 299 | L or M |
| 299 | M, L, or V |
| 325 | Q or L |
| 326 | K, S, P, D, R, N, Y, or H |
| 328 | A or R |
| 328 | Delete P |
| 333 | K, R, D, Q, or E |
| 336 | Delete E |
| 339 | R or L |
| 339 | Delete I |
| 357 | I |
| 358 | L |
| 358 | M or A |
| 361 | K |
| 367 | M |
| 370 | V or L |
| 371 | L |
| 372 | S, P, D, R, N, Y, or H |
| 374 | N |
| 382 | L |
| 386 | V or C |
| 408 | A, S, or T |
| 410 | T, S, L, A, I, V, Q, H, E, G, M, C, V, or T |
| 411 | I |
| 413 | I |
| 414 | G |
| 415 | A, N, G, K, or Q |
| 416 | S, A, or Q |
| 420 | A |

*Unless otherwise denoted, the amino acids listed in this column represent the potential substitutions at the indicated position.

In another embodiment, the compositions of the invention comprise a mutant HPPD polypeptide having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO:27 (the HPPD amino acid sequence of *Avena sativa*) or where the HPPD amino acid sequence derives from a plant, where the polypeptide has HPPD enzymatic activity, and where the polypeptide contains one or more amino acid sequence substitutions corresponding to the amino acid positions listed in column 1 of Table 2, optionally in further combination with known mutations (see e.g., WO2009/144079). In various embodiments, an amino acid at one or more position(s) listed in column 1 of Table 2 is replaced with any other amino acid. In another embodiment, the polypeptide comprises one or more amino acid substitutions corresponding to the amino acid substitutions listed in column 2 of Table 2. In yet another embodiment, the polypeptide comprises one or more substitutions corresponding to a conservative variant of the amino acids listed in column 2 of Table 2. For example, the polypeptide may comprise a mutation corresponding to amino acid position 217 of SEQ ID NO:14 (amino acid position 218 of SEQ ID NO:27), wherein that amino acid is replaced with alanine or a conservative substitution of alanine; or the polypeptide may comprise a mutation corresponding to amino acid position 241 of SEQ ID NO:14 (amino acid position 242 of SEQ ID NO:27), wherein that amino acid is replaced with tryptophan or a conservative substitution of tryptophan; or the polypeptide may comprise a mutation corresponding to amino acid position 408 of SEQ ID NO:14 (amino acid position 409 of SEQ ID NO:27), wherein that amino acid is replaced with alanine or a conservative substitution of alanine. In particular embodiments, the amino acid sequence of the mutant HPPD polypeptide of the invention is selected from the group consisting of SEQ ID NO:14, 15, 16, 17, 18, 19, 20, 21, 22, 23, 24, 25, and 26.

TABLE 2

Exemplary HPPD Mutations

| Amino acid position (relative to SEQ ID NO: 14) | Substitution |
|---|---|
| 217 | I, A, M, or C |
| 241 | S, W, G, M, F, Y, or H |
| 254 | R, S, or A |
| 255 | M, H, G, F, C, or I |
| 258 | M, I, A, or K |
| 269 | M, F, or V |
| 271 | M, I, or V |
| 284 | V, S, A, P, T, L, or G |
| 297 | N, R, G, S, T, E, C, A, or H |
| 325 | Q or L |
| 326 | K, S, P, D, R, N, Y, or H |
| 358 | M or A |
| 408 | A, S, or T |
| 411 | T, S, L, A, I, Q, H, E, G, M, C, V, or T |

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

Accordingly, the present invention also provides nucleic acid molecules comprising polynucleotide sequences that encode mutant HPPD polypeptides that have HPPD enzymatic activity and that confer resistance or tolerance in plants to certain classes of herbicides that inhibit HPPD, and variants and fragments thereof. In general, the invention includes any polynucleotide sequence that encodes any of the mutant HPPD polypeptides described herein, as well as any polynucleotide sequence that encodes HPPD polypeptides having one or more conservative amino acid substitutions relative to the mutant HHPD polypeptides described herein. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q).

In one embodiment, the present invention provides a polynucleotide sequence encoding an amino acid sequence having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO:14 or to SEQ ID NO:27 or where the HPPD amino acid sequence derives from a plant, where the polypeptide has HPPD enzymatic activity, and where the polypeptide contains one or more amino acid sequence additions, substitutions, or deletions as described herein. In particular embodiments, the polynucleotide sequence encodes a mutant HPPD polypeptide having an amino acid sequence selected from the group consisting of SEQ ID NO:14, 15, 16, 17, 18, 19, 20, 21, 22, 23, 24, 25, and 26. In another embodiment, the present invention provides a polynucleotide sequence selected from the group consisting of SEQ ID NO:1, 2, 3, 4, 5, 6, 7, 8, 9, 10, 11, 12, and 13.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of interfering enzyme activities and that is capable of being characterized in respect of its catalytic, kinetic and molecular properties includes quite crude preparations of protein (for example recombinantly produced in cell extracts) having less than about 98%, 95% 90%, 80%, 70%, 60% or 50% (by dry weight) of contaminating protein as well as preparations further purified by methods known in the art to have 40%, 30%, 20%, 10%, 5%, or 1% (by dry weight) of contaminating protein.

The proteins of the invention may be altered in various ways including amino acid substitutions, deletions, truncations, and insertions. Methods for such manipulations are generally known in the art. For example, amino acid sequence variants and fragments of the mutant HPPD proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that often do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The polynucleotides of the invention can also be used to isolate corresponding sequences from other organisms, particularly other plants. In this manner, methods such as PCR, hybridization, and the like can be used to identify such sequences based on their sequence homology to the sequences set forth herein.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art. See, for example, Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

By "hybridizing to" or "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

Fragments and variants of the disclosed nucleotide sequences and proteins encoded thereby are also encompassed by the present invention. "Fragment" is intended to mean a portion of the nucleotide sequence or a portion of the amino acid sequence and hence protein encoded thereby. Fragments of a nucleotide sequence may encode protein fragments that retain the biological activity of the mutant HPPD protein and hence have HPPD enzymatic activity. Alternatively, fragments of a nucleotide sequence that are useful as hybridization probes or in mutagenesis and shuffling reactions to generate yet further HPPD variants generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a nucleotide sequence that encodes a biologically active portion of a mutant HPPD protein of the invention will encode at least 15, 25, 30, 40, 50, 60, 70, 80, 90, 100, 110, 120, 150, 180, 200, 250, 300, or 350 contiguous amino acids, or up to the total number of amino acids present in a full-length mutant HPPD polypeptide of the invention. Fragments of a nucleotide sequence that are useful as hybridization probes or PCR primers generally need not encode a biologically active portion of an HPPD protein.

As used herein, "full-length sequence" in reference to a specified polynucleotide means having the entire nucleic acid sequence of a native or mutated HPPD sequence. "Native sequence" is intended to mean an endogenous sequence, i.e., a non-engineered sequence found in an organism's genome.

Thus, a fragment of a nucleotide sequence of the invention may encode a biologically active portion of a mutant HPPD polypeptide, or it may be a fragment that can be used as a hybridization probe etc. or PCR primer using methods disclosed below. A biologically active portion of a mutant HPPD polypeptide can be prepared by isolating a portion of one of the nucleotide sequences of the invention, expressing the encoded portion of the mutant HPPD protein (e.g., by recombinant expression in vitro), and assessing the activity of the encoded portion of the mutant HPPD protein. Nucleic acid molecules that are fragments of a nucleotide sequence of the invention comprise at least 15, 20, 50, 75, 100, 150, 200, 300, 400, 500, 600, 700, 800, 900, 1000, 1100, 1200, or 1300 contiguous nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the reference polynucleotide and/or a substitution of one or more nucleotides at one or more sites in the mutant HPPD polynucleotide. As used herein, a "reference" polynucleotide or polypeptide comprises a mutant HPPD nucleotide sequence or amino acid sequence, respectively. As used herein, a "native" polynucleotide or polypeptide comprises a naturally occurring nucleotide sequence or amino acid sequence, respectively. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of one of the mutant HPPD polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a mutant HPPD protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptides of SEQ ID NOS: 14, 15, 16, 17, 18, 19, 20, 21, 22, 23, 24, 25, or 26, are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity across the entirety of the HPPD sequences described herein, i.e., when compared to the full length HPPD sequences described herein.

"Variant" protein is intended to mean a protein derived from the reference protein by deletion or addition of one or more amino acids at one or more internal sites in the mutant HPPD protein and/or substitution of one or more amino acids at one or more sites in the mutant HPPD protein. Variant proteins encompassed by the present invention are biologically active, that is they continue to possess the desired biological activity of the mutant HPPD protein, that is, HPPD enzymatic activity and/or herbicide tolerance as described herein. Such variants may result from, for example, genetic polymorphism or from human manipulation. Biologically active variants of a mutant HPPD protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity across the entirety of the amino acid sequence for the mutant HPPD protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

Methods of alignment of sequences for comparison are well known in the art and can be accomplished using mathematical algorithms such as the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; and the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

Gene Stacking

In certain embodiments the polynucleotides of the invention encoding mutant HPPD polypeptides or variants thereof that retain HPPD enzymatic activity (e.g., a polynucleotide sequence encoding an amino acid sequence selected from the group consisting of SEQ ID NO:14, 15, 16, 17, 18, 19, 20, 21, 22, 23, 24, 25, and 26) can be stacked with any combination of polynucleotide sequences of interest in order to create plants with a desired trait. A trait, as used herein, refers to the phenotype derived from a particular sequence or groups of sequences. For example, the polynucleotides encoding a mutant HPPD polypeptide or variant thereof that retains HPPD enzymatic activity may be stacked with any other polynucleotides encoding polypeptides that confer a desirable trait, including but not limited to resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

Exemplary polynucleotides that may be stacked with polynucleotides of the invention encoding an mutant HPPD polypeptide or variant thereof that retains HPPD enzymatic activity include polynucleotides encoding polypeptides conferring resistance to pests/pathogens such as viruses, nematodes, insects or fungi, and the like. Exemplary polynucleotides that may be stacked with polynucleotides of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyl-transferase (GAT) gene, described in Castle et al. (2004) *Science*, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465;

6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference.

Thus, in one embodiment, the polynucleotides encoding a mutant HPPD polypeptide or variant thereof that retains HPPD enzymatic activity are stacked with one or more polynucleotides encoding polypeptides that confer resistance or tolerance to an herbicide. In one embodiment, the desirable trait is resistance or tolerance to an HPPD inhibitor. In another embodiment, the desirable trait is resistance or tolerance to glyphosate. In another embodiment, the desirable trait is resistance or tolerance to glufosinate.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Plant Expression Cassettes

The compositions of the invention may additionally contain nucleic acid sequences for transformation and expression in a plant of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest (i.e., a polynucleotide encoding a mutant HPPD polypeptide or variant thereof that retains HPPD enzymatic activity, alone or in combination with one or more additional nucleic acid molecules encoding polypeptides that confer desirable traits) which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing a polynucleotide of interest, i.e., a polynucleotide encoding a mutant HPPD polypeptide or variant thereof that retains HPPD enzymatic activity, alone or in combination with one or more additional nucleic acid molecules encoding polypeptides that confer desirable traits. The expression cassette will include in the 5'-3' direction of transcription, a transcriptional and translational initiation region (i.e., a promoter) and a polynucleotide open reading frame. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) *Plant J.* 34:383-92 and Chen et al. (2003) *Plant J.* 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence. The promoters that are used for expression of the transgene(s) can be a strong plant promoter, a viral promoter, or a chimeric promoters composed of elements such as: TATA box from any gene (or synthetic, based on analysis of plant gene TATA boxes), optionally fused to the region 5' to the TATA box of plant promoters (which direct tissue and temporally appropriate gene expression), optionally fused to 1 or more enhancers (such as the 35S enhancer, FMV enhancer, CMP enhancer, RUBISCO SMALL SUBUNIT enhancer, PLASTOCYANIN enhancer).

Exemplary constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Appropriate plant or chimeric promoters are useful for applications such as expression of transgenes in certain tissues, while minimizing expression in other tissues, such as seeds, or reproductive tissues. Exemplary cell type- or tissue-preferential promoters drive expression preferentially in the target tissue, but may also lead to some expression in other cell types or tissues as well. Methods for identifying and characterizing promoter regions in plant genomic DNA include, for example, those described in the following references: Jordano, et al., *Plant Cell,* 1:855-866 (1989); Bustos, et al., *Plant Cell,* 1:839-854 (1989); Green, et al., *EMBO J.* 7, 4035-4044 (1988); Meier, et al., *Plant Cell,* 3, 309-316 (1991); and Zhang, et al., *Plant Physiology* 110: 1069-1079 (1996).

In other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1:1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693-8711 (1987); Skuzeski et al. *Plant Molec. Biol.* 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

The present invention also relates to nucleic acid constructs comprising one or more of the expression cassettes described above. The construct can be a vector, such as a plant transformation vector. In one embodiment, the vector is a plant transformation vector comprising a polynucleotide comprising the sequence set forth in SEQ ID NO:34, 35, 36, or 37.

Plants

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

Plants useful in the present invention include plants that are transgenic for at least a polynucleotide encoding a mutant HPPD polypeptide or variant thereof that retains HPPD enzymatic activity, alone or in combination with one or more additional nucleic acid molecules encoding polypeptides that confer desirable traits. The type of plant selected depends on a variety of factors, including for example, the downstream use of the harvested plant material, amenability of the plant species to transformation, and the conditions under which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss.

Plants according to the present invention include any plant that is cultivated for the purpose of producing plant material that is sought after by man or animal for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass and the like. It is recognized that mixtures of plants may be used.

In addition, the term "crops" is to be understood as also including crops that have been rendered tolerant to herbicides or classes of herbicides (such as, for example, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. Examples of crops that have been rendered tolerant to herbicides or classes of herbicides by genetic engineering methods include glyphosate- and glufosinate-resistant crop varieties commercially available under the trade names ROUNDUPREADY® and LIBERTYLINK®. The method according to the present invention is especially suitable for the protection of soybean crops which have also been rendered tolerant to glyphosate and/or glufosinate and where HPPD herbicides are used in a weed control programme along with other such herbicides (glufosinate and/or glyphosate) for weed control.

It is further contemplated that the constructs of the invention may be introduced into plant varieties having improved properties suitable or optimal for a particular downstream use. For example, naturally-occurring genetic variability results in plants with resistance or tolerance to HPPD inhibitors or other herbicides, and such plants are also useful in the methods of the invention. The method according to the present invention can be further optimized by crossing the transgenes that provide a level of tolerance, with soybean cultivars that exhibit an enhanced level of tolerance to HPPD inhibitors that is found in a small percentage of soybean lines.

Plant Transformation

Once an herbicide resistant or tolerant mutant HPPD polynucleotide, alone or in combination with one or more additional nucleic acid molecules encoding polypeptides that confer desirable traits, has been cloned into an expression system, it is transformed into a plant cell. The receptor and target expression cassettes of the present invention can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the npt11 gene, which confers resistance to kanamycin and related antibiotics (Messing & Vierra *Gene* 19: 259-268 (1982); Bevan et al., *Nature* 304:184-187 (1983)), the pat and bar genes, which confer resistance to the herbicide glufosinate (also called phosphinothricin; see White et al., *Nucl. Acids Res* 18: 1062 (1990), Spencer et al. *Theor. Appl. Genet.* 79: 625-631 (1990) and U.S. Pat. Nos. 5,561,236 and 5,276,268), the hph gene, which confers resistance to the antibiotic hygromycin (Blochinger & Diggelmann, *Mol. Cell. Biol.* 4: 2929-2931), and the dhfr gene, which confers resistance to methatrexate (Bourouis et al., *EMBO J.* 2(7): 1099-1104 (1983)), the EPSPS gene, which confers resistance to glyphosate (U.S. Pat. Nos. 4,940,935 and 5,188,642), the glyphosate N-acetyltransferase (GAT) gene, which also confers resistance to glyphosate (Castle et al. (2004) *Science,* 304:1151-1154; U.S. Patent App. Pub. Nos. 20070004912, 20050246798, and 20050060767); and the mannose-6-phosphate isomerase gene, which provides the ability to metabolize mannose (U.S. Pat. Nos. 5,767,378 and 5,994,629). Alternatively, and in one preferred embodiment the HPPD gene of the current invention is, in combination with the use of an HPPD herbicide as selection agent, itself used as the selectable marker.

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, *Nucl. Acids Res.* (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

For expression of a nucleotide sequence of the present invention in plant plastids, plastid transformation vector pPH143 (WO 97/32011, See Example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J.* 3: 2717-2722 (1984), Potrykus et al., *Mol. Gen. Genet.* 199: 169-177 (1985), Reich et al., *Biotechnology* 4: 1001-1004 (1986), and Klein et al., *Nature* 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. *Plant Cell* 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, *Nucl. Acids Res.* 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (*Plant Cell* 2: 603-618 (1990)) and Fromm et al. (*Biotechnology* 8: 833-839 (1990)) have published techniques for transformation of A188-derived maize line using particle bombardment. Furthermore, WO 93/07278 and Koziel et al. (*Biotechnology* 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. *Plant Cell Rep* 7: 379-384 (1988); Shimamoto et al. *Nature* 338: 274-277 (1989); Datta et al. *Biotechnology* 8:736-740 (1990)). Both types are also routinely transformable using particle bombardment (Christou et al. *Biotechnology* 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (*Biotechnology* 10: 667-674 (1992)) using particle bombardment into cells of type C long-term regenerable callus, and also by Vasil et al. (*Biotechnology* 11:1553-1558 (1993)) and Weeks et al. (*Plant Physiol.* 102:1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, *Physiologia Plantarum* 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., *Plant Cell Reports* 19: 798-803 (2000), incorporated herein by reference.

For example, rice (*Oryza sativa*) can be used for generating transgenic plants. Various rice cultivars can be used (Hiei et al., 1994, *Plant Journal* 6:271-282; Dong et al., 1996, *Molecular Breeding* 2:267-276; Hiei et al., 1997, *Plant Molecular Biology*, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is re-suspended in liquid MS-CIM medium. The *Agrobacterium* culture is diluted to an OD600 of 0.2-0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., *In Vitro Cell. Dev. Biol.-Plant* 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of interest in the present invention can be any of a wide variety of plant species, including those of monocots and dicots; however, the plants used in the method of the invention are preferably selected from the list of agronomically important target crops set forth elsewhere herein. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) *PNAS* 90, 913-917). Bombarded seedlings are incubated on T medium for two days after which leaves are excised and placed abaxial side up in bright light (350-500 umol photons/$m^2$/s) on plates of RMOP medium (Svab, Z., Hajdukiewicz, P. and Maliga, P. (1990) *PNAS* 87, 8526-8530) containing 500 ug/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) *Plant Mol Biol Reporter* 5, 346349) is separated on 1% Tris-borate (TBE) agarose gels, transferred to nylon membranes (Amersham) and probed with .sup.32P-labeled random primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride, K. E. et al. (1994) *PNAS* 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified genetic properties.

Many suitable methods for transformation using suitable selection markers such as kanamycin, binary vectors such as from *Agrobacterium* and plant regeneration as, for example, from tobacco leaf discs are well known in the art. Optionally, a control population of plants are likewise transformed with a polynucleotide expressing the control HPPD. Alternatively, an untransformed dicot plant such as *Arabidopsis* or Tobacco can be used as a control since this, in any case, expresses its own endogenous HPPD.

Herbicide Resistance

The present invention provides transgenic plants, plant cells, tissues, and seeds that have been transformed with a nucleic acid molecule encoding a mutant HPPD or variant thereof that confers resistance or tolerance to herbicides, alone or in combination with one or more additional nucleic acid molecules encoding polypeptides that confer desirable traits.

In one embodiment, the transgenic plants of the invention exhibit resistance or tolerance to application of herbicide in an amount of from about 5 to about 2,000 grams per hectare (g/ha), including, for example, about 5 g/ha, about 10 g/ha, about 15 g/ha, about 20 g/ha, about 25 g/ha, about 30 g/ha, about 35 g/ha, about 40 g/ha, about 45 g/ha, about 50 g/ha, about 55 g/ha, about 60 g/ha, about 65 g/ha, about 70 g/ha, about 75 g/ha, about 80 g/ha, about 85 g/ha, about 90 g/ha, about 95 g/ha, about 100 g/ha, about 110 g/ha, about 120 g/ha, about 130 g/ha, about 140 g/ha, about 150 g/ha, about 160 g/ha, about 170 g/ha, about 180 g/ha, about 190 g/ha, about 200 g/ha, about 210 g/ha, about 220 g/ha, about 230 g/ha, about 240 g/ha, about 250 g/ha, about 260 g/ha, about 270 g/ha, about 280 g/ha, about 290 g/ha, about 300 g/ha, about 310 g/ha, about 320 g/ha, about 330 g/ha, about 340 g/ha, about 350 g/ha, about 360 g/ha, about 370 g/ha, about 380 g/ha, about 390 g/ha, about 400 g/ha, about 410 g/ha, about 420 g/ha, about 430 g/ha, about 440 g/ha, about 450 g/ha, about 460 g/ha, about 470 g/ha, about 480 g/ha, about 490 g/ha, about 500 g/ha, about 510 g/ha, about 520 g/ha, about 530 g/ha, about 540 g/ha, about 550 g/ha, about 560 g/ha, about 570 g/ha, about 580 g/ha, about 590 g/ha, about 600 g/ha, about 610 g/ha, about 620 g/ha, about 630 g/ha, about 640 g/ha, about 650 g/ha, about 660 g/ha, about 670 g/ha, about 680 g/ha, about 690 g/ha, about 700 g/ha, about 710 g/ha, about 720 g/ha, about 730 g/ha, about 740 g/ha, about 750 g/ha, about 760 g/ha, about 770 g/ha, about 780 g/ha, about 790 g/ha, about 800 g/ha, about 810 g/ha, about 820 g/ha, about 830 g/ha, about 840 g/ha, about 850 g/ha, about 860 g/ha, about 870 g/ha, about 880 g/ha, about 890 g/ha, about 900 g/ha, about 910 g/ha, about 920 g/ha, about 930 g/ha, about 940 g/ha, about 950 g/ha, about 960 g/ha, about 970 g/ha, about 980 g/ha, about 990 g/ha, about 1,000 g/ha, about 1,010 g/ha, about 1,020 g/ha, about 1,030 g/ha, about 1,040 g/ha, about 1,050 g/ha, about 1,060 g/ha, about 1,070 g/ha, about 1,080 g/ha, about 1,090 g/ha, about 1,100 g/ha, about 1,110 g/ha, about 1,120 g/ha, about 1,130 g/ha, about 1,140 g/ha, about 1,150 g/ha, about 1,160 g/ha, about 1,170 g/ha, about 1,180 g/ha, about 1,190 g/ha, about 1,200 g/ha, about 1,210 g/ha, about 1,220 g/ha, about 1,230 g/ha, about 1,240 g/ha, about 1,250 g/ha, about 1,260 g/ha, about 1,270 g/ha, about 1,280 g/ha, about 1,290 g/ha, about 1,300 g/ha, about 1,310 g/ha, about 1,320 g/ha, about 1,330 g/ha, about 1,340 g/ha, about 1,350 g/ha, about 360 g/ha, about 1,370 g/ha, about 1,380 g/ha, about 1,390 g/ha, about 1,400 g/ha, about 1,410 g/ha, about 1,420 g/ha, about 1,430 g/ha, about 1,440 g/ha, about 1,450 g/ha, about 1,460 g/ha, about 1,470 g/ha, about 1,480 g/ha, about 1,490 g/ha, about 1,500 g/ha, about 1,510 g/ha, about 1,520 g/ha, about 1,530 g/ha, about 1,540 g/ha, about 1,550 g/ha, about 1,560 g/ha, about 1,570 g/ha, about 1,580 g/ha, about 1,590 g/ha, about 1,600 g/ha, about 1,610 g/ha, about 1,620 g/ha, about 1,630 g/ha, about 1,640 g/ha, about 1,650 g/ha, about 1,660 g/ha, about 1,670 g/ha, about 1,680 g/ha, about 1,690 g/ha, about 1,700 g/ha, about 1,710 g/ha, about 1,720 g/ha, about 1,730 g/ha, about 1,740 g/ha, about 1,750 g/ha, about 1,760 g/ha, about 1,770 g/ha, about 1,780 g/ha, about 1,790 g/ha, about 1,800 g/ha, about 1,810 g/ha, about 1,820 g/ha, about 1,830 g/ha, about 1,840 g/ha, about 1,850 g/ha, about 1,860 g/ha, about 1,870 g/ha, about 1,880 g/ha, about 1,890 g/ha, about 1,900 g/ha, about 1,910 g/ha, about 1,920 g/ha, about 1,930 g/ha, about 1,940 g/ha, about 1,950 g/ha, about 1,960 g/ha, about 1,970 g/ha, about 1,980 g/ha, about 1,990 g/ha, or about 2,000.

The average and distribution of herbicide tolerance or resistance levels of a range of primary plant transformation events are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent inhibitor-tolerance (e.g. increased $Ki/Km_{HPP}$ value) and/or level of expression of the expressed HPPD polypeptide.

The methods of the present invention are especially useful to protect crops from the herbicidal injury of HPPD inhibitor herbicides of the classes of HPPD chemistry described below. In one embodiment, the selected from the group consisting of:

a) a compound of formula (Ia)

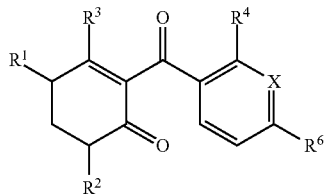

wherein $R^1$ and $R^2$ are hydrogen or together form an ethylene bridge;
$R^3$ is hydroxy or phenylthio-; $R^4$ is halogen, nitro, $C_1$-$C_4$alkyl, $C_1$-$C_4$alkoxy-$C_1$-$C_4$alkyl-, $C_1$-$C_4$alkoxy-$C_1$-$C_4$alkoxy-$C_1$-$C_4$alkyl-;
X is methine, nitrogen, or C—$R^5$ wherein $R^5$ is hydrogen, $C_1$-$C_4$alkoxy, $C_1$-$C_4$haloalkoxy-$C_1$-$C_4$alkyl-, or a group

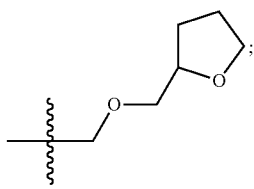 [SMILES: *COCC1CCCO1]

and
$R^6$ is $C_1$-$C_4$alkylsulfonyl- or $C_1$-$C_4$haloalkyl;

b) a compound of formula (Ib)

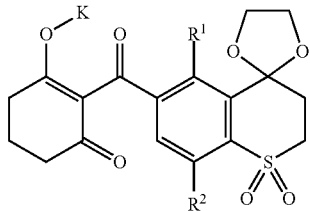

$R^1$ and $R^2$ are independently $C_1$-$C_4$alkyl; and the free acids thereof;

c) a compound of formula (Ic)

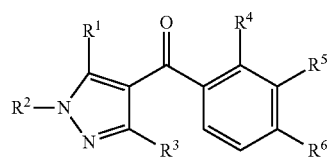

wherein $R^1$ is hydroxy, phenylcarbonyl-$C_1$-$C_4$alkoxy- or phenylcarbonyl-$C_1$-$C_4$alkoxy—wherein the phenyl moiety is substituted in para-position by halogen or $C_1$-$C_4$alkyl, or phenylsulfonyloxy—or phenylsulfonyloxy—wherein the phenyl moiety is substituted in para-position by halogen or $C_1$-$C_4$alkyl;

$R^2$ is $C_1$-$C_4$alkyl;
$R^3$ is hydrogen or $C_1$-$C_4$alkyl; $R^4$ and $R^6$ are independently halogen, $C_1$-$C_4$alkyl, $C_1$-$C_4$haloalkyl, or $C_1$-$C_4$alkylsulfonyl-; and
$R^5$ is hydrogen, $C_1$-$C_4$alkyl, $C_1$-$C_4$alkoxy-$C_1$-$C_4$alkoxy-, or a group

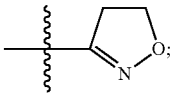 [SMILES: *C1=NOCC1]

d) a compound of formula (Id)

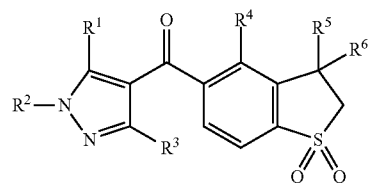

wherein $R^1$ is hydroxy;
$R^2$ is $C_1$-$C_4$alkyl;
$R^3$ is hydrogen; and $R^4$, $R^5$ and $R^6$ are independently $C_1$-$C_4$alkyl;

e) a compound of formula (Ie)

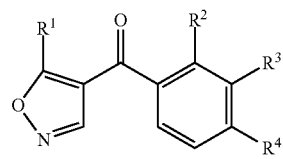

wherein $R^1$ is cyclopropyl;
$R^2$ and $R^4$ are independently halogen, $C_1$-$C_4$haloalkyl, or $C_1$-$C_4$alkylsulfonyl-; and
$R^3$ is hydrogen;

f) a compound of formula (If)

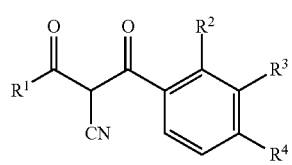

wherein $R^1$ is cyclopropyl;
$R^2$ and $R^4$ are independently halogen, $C_1$-$C_4$haloalkyl, or $C_1$-$C_4$alkylsulfonyl-; and
$R^3$ is hydrogen;

g) a compound of formula (Ig) or Formula (Ih)

(Ig)

(Ih)

wherein:
$R^2$ is selected from the group consisting of $C_1$-$C_3$alkyl, $C_1$-$C_3$haloalkyl, $C_1$-$C_3$alkoxy-$C_1$-$C_3$ alkyl and $C_1$-$C_3$ alkoxy-$C_2$-$C_3$alkoxy-$C_1$-$C_3$-alkyl;
$R^5$ is hydrogen or methyl;
$R^6$ is selected from the group consisting of hydrogen, fluorine, chlorine, hydroxyl and methyl;
$R^7$ is selected from the group consisting of hydrogen, halogen, hydroxyl, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, $C_3$-$C_6$alkynyl, $C_1$-$C_6$alkoxy, $C_4$-$C_7$cycloalkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, amino, $C_1$-$C_6$alkylamino, $C_2$-$C_6$dialkylamino, $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-R', $C_1$-$C_4$alkyleneyl-$CO_2$—R', $C_1$-$C_4$alkyleneyl-(CO)N—R'R', phenyl, phenylthio, phenylsulfinyl, phenylsulfonyl, phenoxy, pyrrolidinyl, piperidinyl, morpholinyl and 5 or 6-membered heteroaryl or heteroaryloxy, the heteroaryl containing one to three heteroatoms, each independently selected from the group consisting of oxygen, nitrogen and sulphur, wherein the phenyl or heteroaryl component may be optionally substituted by a substituent selected from the group consisting of $C_1$-$C_3$alkyl, $C_1$-$C_3$haloalkyl, $C_1$-$C_3$ alkoxy, $C_1$-$C_3$haloalkoxy, halo, cyano, and nitro;
X═O or S;
n=0 or 1;
m=0 or 1 with the proviso that if m=1 then n=0 and if n=1 then m=0;
p=0, 1, or 2;
R' is independently selected from the group consisting of hydrogen and $C_1$-$C_6$alkyl;
$R^8$ is selected from the group consisting of hydrogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkylalkeneyl for example cyclohexylmethylenyl, $C_3$-$C_6$alkynylalkyleneyl for example propargyl, $C_2$-$C_6$-alkenylalkylenyl for example allyl, $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with a substituent selected from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with a substituent selected from the group consisting of halo, $C_1$-$C_3$-alkoxy, $C_1$-$C_3$-alkyl, $C_1$-$C_3$ haloalkyl), $C_1$-$C_6$alkoxy $C_1$-$C_6$alkoxy $C_1$-$C_6$alkyl and a 5 or 6-membered heteroaryl-$C_1$-$C_3$-alkyl or heterocyclyl-$C_1$-$C_3$-alkyl, the heteroaryl or heterocyclyl containing one to three heteroatoms, each independently selected from the group consisting of oxygen, nitrogen and sulphur, wherein the heterocyclyl or heteroaryl component may be optionally substituted by a substituent selected from the group consisting of halo, $C_1$-$C_3$alkyl, $C_1$-$C_3$haloalkyl, and $C_1$-$C_3$ alkoxy;
Q is selected from the group consisting of:

(Q1)

(Q2)

(Q3)

(Q4)

(Q5)

(Q6)

and (Q7)

wherein
$A^1$ is selected from the group consisting of O, C(O), S, SO, $SO_2$ and $(CR^eR^f)_q$;
q=0, 1 or 2;
$R^a$, $R^b$, $R^c$, $R^d$, $R^e$ and $R^f$ are each independently selected from the group consisting of $C_1$-$C_4$alkyl which may be mono-, dior tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl and heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or $R^a$, $R^b$, $R^c$, $R^d$, $R^e$ and $R^f$ are each independently selected from the group consisting of hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or $R^a$ and $R^b$ together form a 3- to 5-membered carbocyclic ring which may be substituted by $C_1$-$C_4$alkyl and may be interrupted by oxygen, sulfur, S(O), $SO_2$, OC(O), $NR^g$ or by C(O); or $R^a$ and $R^c$ together form a $C_1$-$C_3$alkylene chain which may be interrupted by oxygen, sulfur, SO, $SO_2$, OC(O), $NR^h$ or by C(O); it being possible for that $C_1$-$C_3$alkylene chain in turn to be substituted by $C_1$-$C_4$alkyl;

$R^g$ and $R^h$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl;

$R^i$ is $C_1$-$C_4$alkyl;

$R^3$ is selected from the group consisting of $C_1$-$C_6$alkyl, optionally substituted with halogen and/or $C_1$-$C_3$alkoxy; and $C_3$-$C_6$ cycloalkyl optionally substituted with halogen and/or $C_1$-$C_3$alkoxy;

$R^9$ is selected from the group consisting of cyclopropyl, $CF_3$ and i.-Pr;

$R^{10}$ is selected from the group consisting of hydrogen, I, Br, $SR^{11}$, $S(O)R^{11}$, $S(O)_2R^{11}$ and $CO_2R^{11}$; and $R^{11}$ is $C_{1-4}$ alkyl;

h) a compound of formula (Ij), (Ik), or (Im)

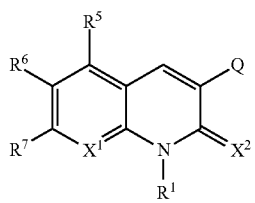

(Ij)

or an agronomically acceptable salt of said compound, wherein:

$R^1$ is selected from the group consisting of hydrogen, $C_1$-$C_6$alkyl, $C_1$-$C_6$haloalkyl, $C_1$-$C_3$alkoxy-$C_1$-$C_3$ alkyl, $C_1$-$C_3$alkoxy-$C_1$-$C_3$alkoxy-$C_1$-$C_3$-alkyl, $C_1$-$C_3$alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstituted cycloalkyl-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$alkanesulfonyl-$C_1$-$C_3$alkylamino)-$C_1$-$C_3$ alkyl, ($C_1$-$C_3$ alkanesulfonyl-$C_3$-$C_4$ cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkeneyl, $C_3$-$C_6$alkynyl, $C_2$-$C_6$-alkenyl, cyano-$C_1$-$C_6$-alkyl, arylcarbonyl-$C_1$-$C_3$-alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), aryl, 5 or 6-membered heteroaryl, 5 or 6-membered heteroaryl-$C_1$-$C_3$alkyl and heterocyclyl-$C_1$-$C_3$alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)p-, $C_1$-$C_6$haloalkyl-S(O)p-, cyano and nitro;

$R^5$ is selected from the group consisting of hydrogen, chloro, fluoro and methyl;

$R^6$ is selected from the group consisting of hydrogen, fluorine, chlorine, hydroxyl and methyl;

$R^7$ is selected from the group consisting of hydrogen, cyano, nitro, halogen, hydroxyl, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, aryl-$C_2$-$C_6$alkenyl, $C_3$-$C_6$alkynyl, $C_1$-$C_6$alkoxy, $C_4$-$C_7$ cycloalkoxy, $C_1$-$C_6$haloalkoxy, $C_1$-$C_6$alkyl-S(O)p, $C_3$-$C_6$cycloalkyl-S(O)p $C_1$-$C_6$haloalkyl-S(O)p, $C_3$-$C_6$ halocycloalkyl-S(O)p, $C_1$-$C_6$alkylcarbonylamino, ($C_1$-$C_6$alkylcarbonyl)$C_1$-$C_3$alkylamino, ($C_3$-$C_6$cycloalkylcarbonyl)amino, ($C_3$-$C_6$cycloalkylcarbonyl)$C_1$-$C_3$alkylamino, arylcarbonylamino, (arylcarbonyl)-$C_{1-3}$alkylamino, (heteroarylcarbonyl)amino, (heteroarylcarbonyl)$C_1$-$C_3$alkylamino, amino, $C_1$-$C_6$alkylamino, $C_2$-$C_6$dialkylamino, $C_2$-$C_6$alkenylamino, $C_1$-$C_6$alkoxy-$C_2$-$C_6$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$ cycloalkylamino, $C_3$-$C_6$ alkynylamino, dialkylamino in which the substituents join to form a 4-6 membered ring (e.g pyrrolidinyl, piperidinyl) optionally containing oxygen (e.g morpholinyl) and/or optionally substituted by $C_1$-$C_3$-alkoxy and/or halogen (especially fluorine), $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-R', $C_1$-$C_4$alkylenyl-$CO_2$—R', $C_1$-$C_4$alkylenyl-(CO)N—R'R', aryl (e.g. phenyl), aryl $C_1$-$C_3$alkyl, aryl-S(O)p, heteroaryl-S(O)p, aryloxy (e.g phenoxy), a 5 or 6-membered heteroaryl, heteroaryl $C_1$-$C_3$ alkyl and heteroaryloxy, the heteroaryl containing one to three heteroatoms, each independently selected from the group consisting of oxygen, nitrogen and sulphur, wherein the aryl or heteroaryl component may be optionally substituted by one or more substituents selected from the group consisting of $C_1$-$C_3$alkyl, $C_1$-$C_3$haloalkyl, $C_1$-$C_3$ alkoxy, $C_1$-$C_3$haloalkoxy, halo, cyano and nitro;

$X^1$=N—(O)n or C—$R^8$;

$X^2$=O or S;

n=0 or 1;

p=0, 1 or 2;

R' is independently selected from the group consisting of hydrogen and $C_1$-$C_6$alkyl;

$R^8$ is selected from the group consisting of hydrogen, halogen, $C_1$-$C_6$alkyl, $C_1$-$C_6$haloalkyl, $C_1$-$C_6$alkylcarbonyl-$C_1$-

$C_3$alkyl, $C_3$-$C_6$cycloalkyl-$C_2$-$C_6$alkenyl for example cyclohexylmethylenyl, $C_3$-$C_6$alkynyl (for example propargyl), $C_2$-$C_6$-alkenyl (for example allyl), $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with one or more substituents selected from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), $C_1$-$C_6$alkoxy$C_1$-$C_6$alkoxy $C_1$-$C_6$alkyl, aryl, a 5 or 6-membered heteroaryl, a 5 or 6-membered heteroaryl-$C_1$-$C_3$-alkyl and heterocyclyl-$C_1$-$C_3$-alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents from the group consisting of halogen, $C_1$-$C_3$alkyl, $C_1$-$C_3$haloalkyl and $C_1$-$C_3$ alkoxy, cyano and nitro;

Q is selected from the group consisting of:—

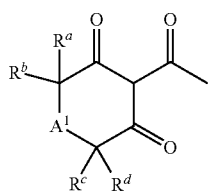
(Q1)

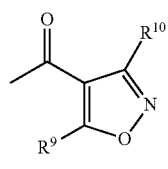
(Q2)

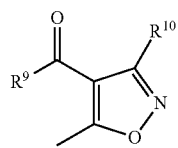
(Q3)

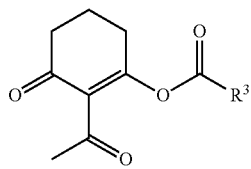
(Q4)

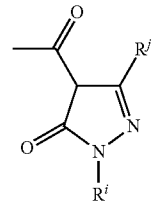
(Q5)

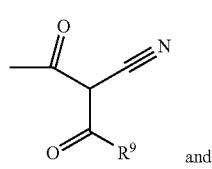
(Q6)

and

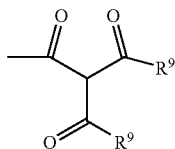
(Q7)

wherein
$A^1$ is selected from the group consisting of O, C(O), S, SO, $SO_2$ and $(CR^eR^f)_q$;
q=0, 1 or 2;
$R^a$, $R^b$, $R^c$, $R^d$, $R^e$ and $R^f$ are each independently selected from the group consisting of $C_1$-$C_4$alkyl which may be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl and heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or
$R^a$, $R^b$, $R^c$, $R^d$, $R^e$ and $R^f$ are each independently selected from the group consisting of hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or
$R^a$ and $R^b$ together form a 3- to 5-membered carbocyclic ring which may be substituted by $C_1$-$C_4$alkyl and may be interrupted by oxygen, sulfur, S(O), $SO_2$, OC(O), $NR^g$ or by C(O); or
$R^a$ and $R^c$ together form a $C_1$-$C_3$alkylene chain which may be interrupted by oxygen, sulfur, SO, $SO_2$, OC(O), $NR^h$ or by C(O); it being possible for that $C_1$-$C_3$alkylene chain in turn to be substituted by $C_1$-$C_4$alkyl;
$R^g$ and $R^h$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl;
$R^i$ is $C_1$-$C_4$alkyl;
$R^j$ is selected from the group consisting of hydrogen, $C_1$-$C_4$ alkyl and $C_3$-$C_6$ cycloalkyl;
$R^3$ is selected from the group consisting of $C_1$-$C_6$alkyl, optionally substituted with halogen and/or $C_1$-$C_3$alkoxy, and $C_3$-$C_6$ cycloalkyl optionally substituted with halogen and/or $C_1$-$C_3$alkoxy;
$R^9$ is selected from the group consisting of cyclopropyl, $CF_3$ and i.-Pr;
$R^{10}$ is selected from the group consisting of hydrogen, I, Br, $SR^{11}$, $S(O)R^{11}$, $S(O)_2R^{11}$ and $CO_2R^{11}$; and
$R^{11}$ is $C_{1-4}$ alkyl.

With respect to the structures (Ia)-(Im) described herein:
Halogen encompasses fluorine, chlorine, bromine or iodine. The same correspondingly applies to halogen in the context of other definitions, such as haloalkyl or halophenyl.
Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Suitable alkylenyl radicals include, for example $CH_2$, $CHCH_3$, $C(CH_3)_2$, $CH_2CHCH_3$, $CH_2CH(C_2H_5)$.

Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Preferred $C_2$-$C_6$alkenyl radicals substituted once, twice or three times by halogen are those having a chain length of from 2 to 5 carbon atoms. Suitable haloalkylalkynyl radicals include, for example, alkylalkynyl groups substituted one or more times by halogen, halogen being bromine or iodine and, especially, fluorine or chlorine, for example 3-fluoropropynyl, 5-chloropent-2-yn-1-yl, 5-bromopent-2-yn-1-yl, 3,3,3-trifluoropropynyl and 4,4,4-trifluoro-but-2-yn-1-yl. Preferred alkylalkynyl groups substituted one or more times by halogen are those having a chain length of from 3 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl, ethoxycarbonyl or tert-butoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Cycloalkylamino or dicycloalkylamino is for example cyclohexylamino or dicyclopropylamino.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 6 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthio-methyl, butylthioethyl or butylthiobutyl.

Cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl.

Phenyl, including phenyl as part of a substituent such as phenoxy, benzyl, benzyloxy, benzoyl, phenylthio, phenylalkyl, phenoxyalkyl or tosyl, may be in mono- or poly-substituted form, in which case the substituents may, as desired, be in the ortho-, meta- and/or para-position(s).

Heterocyclyl, for example, includes morpholinyl, tetrahydrofuryl.

Heteroaryl, including heteroaryl as part of a substituent such as heteroaryloxy, means a five or six member heteroaryl containing one to three heteroatoms, each independently selected from the group consisting of oxygen, nitrogen and sulphur. It should be understood that the heteroaryl component may be optionally mono or poly substituted. The term heteroaryl thus includes, for example, furanyl, thiopheneyl, thiazolyl, oxazolyl, isoxazolyl, thiazolyl, pyrazolyl, isothiazolyl, pyridyl, pyridazinyl, pyrazinyl, pyrimidinyl, triazolyl.

Compounds of Formula Ij may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula Ij comprising Q1, Q5, Q6 or Q7 or when $R^1$ is hydrogen may be in equilibrium with alternative hydroxyl tautomeric forms. It should be appreciated that all tautomeric forms (single tautomer or mixtures thereof), racemic mixtures and single isomers are included within the scope of the present invention.

The skilled person will also appreciate that if n is 1 with regard to Formula Ij to form the N-oxide then the nitrogen and oxygen will be charged accordingly ($N^+O^-$).

In a preferred embodiment of the present invention $X^2$ is oxygen.

In another preferred embodiment $R^1$ is selected from the group consisting of hydrogen, $C_1$-$C_6$alkyl, $C_1$-$C_3$alkoxy$C_1$-$C_3$alkyl, $C_1$-$C_3$alkoxy $C_2$-$C_3$alkoxy$C_1$-$C_3$alkyl, $C_1$-$C_6$haloalkyl, $C_1$-$C_3$alkoxy-$C_1$-$C_3$haloalkyl and phenyl.

In another preferred embodiment $R^1$ is aryl, preferably phenyl, or a 5 or 6-membered heteroaryl containing one to three heteroatoms each independently selected from the group consisting of oxygen, nitrogen and sulphur, and wherein the aryl or heteroaryl may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)p-, $C_1$-$C_6$haloalkyl-S(O)p-, cyano and nitro.

In another preferred embodiment $R^5$ is hydrogen.

In another preferred embodiment $R^6$ is hydrogen or fluorine.

In another preferred embodiment $R^j$ is selected from the group consisting of hydrogen, methyl and cyclopropyl.

In another preferred embodiment the herbicidal compound is of Formula (Ik):

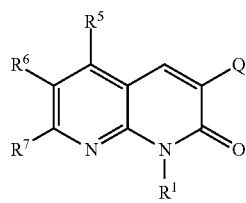

(Ik)

In a more preferred embodiment of the present invention the herbicidal compound is of Formula (Ik) wherein Q is Q1, in particular wherein $A^1$ is $CR^eR^f$ and wherein $R^a$, $R^b$, $R^c$, $R^d$, $R^e$ and $R^f$ are hydrogen, and wherein q=1. In another preferred embodiment of the present invention Q is Q1, wherein $A^1$ is $CR^eR^f$ and wherein, $R^b$, $R^d$, $R^e$ and $R^f$ are hydrogen, $R^a$ and $R^c$ together form an ethylene chain and wherein q=1

In another preferred embodiment, when the herbicidal compound is of Formula (Ik) and wherein $R^7$ is selected from the group consisting of hydrogen, hydroxyl, halogen, $C_1$-$C_6$alkyl, $C_3$-$C_6$cycloalkyl, $C_1$-$C_6$haloalkyl, $C_1$-$C_6$ alkoxy, $C_1$-$C_6$ alkoxy-$C_2$-$C_6$-alkoxy, $C_1$-$C_6$-alkoxy-$C_1$-$C_6$ alkyl, $C_1$-$C_6$-alkoxy-$C_2$-$C_6$-alkoxy-$C_1$-$C_6$ alkyl, $C_1$-$C_6$alkylamino, $C_1$-$C_6$dialkylamino, $C_2$-$C_6$alkenylamino, $C_1$-$C_6$alkoxy-$C_2$-$C_3$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$ cycloalkylamino, $C_3$-$C_6$ alkynylamino and dialkylamino group in which the substituents join to form a 4-6 membered ring, optionally containing oxygen, and/or optionally substituted by $C_1$-$C_3$-alkoxy and/or halogen, especially fluorine. In an even more preferred embodiment $R^7$ is selected from the group consisting of hydrogen, chloro, methyl, ethyl, 1-methylethyl, cyclopropyl, fluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, 1-methoxyethyl, 2-methoxyethoxy, 2-methoxyethoxymethyl, (2-methoxyethyl)amino and (2-methoxyethyl)methylamino.

In another preferred embodiment the herbicidal compound is of Formula (Im):

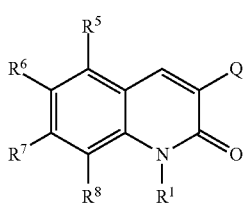

(Im)

In another preferred embodiment of the present invention the herbicidal compound is of Formula (Im), wherein Q is Q1, in particular wherein $A^1$ is $CR^eR^f$ and wherein $R^a$, $R^b$, $R^c$, $R^d$, $R^e$ and $R^f$ are hydrogen, and wherein q=1. In another preferred embodiment of the present invention Q is Q1, wherein $A^1$ is $CR^eR^f$ and wherein, $R^b$, $R^d$, $R^e$ and $R^f$ are hydrogen, $R^a$ and $R^c$ together form an ethylene chain and wherein q=1.

In another preferred embodiment wherein the herbicidal compound is of Formula (Im) and wherein $R^7$ is selected from the group consisting of hydrogen, cyano, halogen, nitro, $C_1$-$C_6$haloalkyl, $C_1$-$C_3$ alkoxy$C_1$-$C_3$haloalkyl, $C_1$-$C_3$ alkoxy$C_2$-$C_6$-alkoxy$C_1$-$C_3$ haloalkyl, $C_1$-$C_3$ haloalkoxy, $C_1$-$C_6$alkylS(O)p, $C_{3-6}$cycloalkylS(O)p $C_1$-$C_6$haloalkyl-S(O)p, $C_3$-$C_6$halocycloalkyl-S(O)p, aryl-S(O)$_p$ and heteroaryl-S(O)p. In an even more preferred embodiment $R^7$ is selected from the group consisting of chloro, fluoro, cyano, nitro, fluoromethyl, difluoromethyl, trifluoromethyl, 1-fluoroethyl, 1,1-difluoroethyl, 1-fluoro-1-methylethyl, difluorochloromethyl, difluoromethoxy, trifluoromethoxy, 1,1-difluoroethoxy, methylsulfinyl, methylsulfonyl, ethylsulfinyl, ethylsulfonyl, phenyl sulfinyl and phenyl sulfonyl.

In further preferred embodiments HPPD herbicidal compounds are bicyclic compounds as described in WO2009/016841.

In a particular embodiment the HPPD inhibitor is selected from the group consisting of benzobicyclon, mesotrione, sulcotrione, tefuryltrione, tembotrione, 4-hydroxy-3-[[2-(2-methoxyethoxy)methyl]-6-(trifluoromethyl)-3-pyridinyl]carbonyl]-bicyclo[3.2.1]oct-3-en-2-one, ketospiradox or the free acid thereof, benzofenap, pyrasulfotole, pyrazolynate, pyrazoxyfen, topramezone, [2-chloro-3-(2-methoxyethoxy)-4-(methylsulfonyl)phenyl](1-ethyl-5-hydroxy-1H-pyrazol-4-yl)-methanone, (2,3-dihydro-3,3,4-trimethyl-1,1-dioxidobenzo[b]thien-5-yl)(5-hydroxy-1-methyl-1H-pyrazol-4-yl)-methanone, isoxachlortole, isoxaflutole, α-(cyclopropylcarbonyl)-2-(methylsulfonyl)-β-oxo-4-chloro-benzenepropanenitrile, and α-(cyclopropylcarbonyl)-2-(methylsulfonyl)-β-oxo-4-(trifluoromethyl)-benzenepropanenitrile.

Other HPPD inhibitors are well known in the art and may be used within the methods of the present invention, including HPPD inhibitors that have the following Chemical Abstracts registration numbers: benzobicyclon (CAS RN 156963-66-5), mesotrione (CAS RN 104206-82-8), sulcotrione (CAS RN 99105-77-8), tefuryltrione (CAS RN 473278-76-1), tembotrione (CAS RN 335104-84-2), 4-hydroxy-3-[[2-(2-methoxyethoxy)methyl]-6-(trifluoromethyl)-3-pyridinyl]carbonyl]-bicyclo[3.2.1]oct-3-en-2-one (CAS RN 352010-68-5), ketospiradox (CAS RN 192708-91-1) or its free acid (CAS RN 187270-87-7), benzofenap (CAS RN 82692-44-2), pyrasulfotole (CAS RN 365400-11-9), pyrazolynate (CAS RN 58011-68-0), pyrazoxyfen (CAS RN 71561-11-0), topramezone (CAS RN 210631-68-8), [2-chloro-3-(2-methoxyethoxy)-4-(methylsulfonyl)phenyl](1-ethyl-5-hydroxy-1H-pyrazol-4-yl)-methanone (CAS RN 128133-27-7), (2,3-dihydro-3,3,4-trimethyl-1,1-dioxidobenzo[b]thien-5-yl)(5-hydroxy-1-methyl-1H-pyrazol-4-yl)-methanone (CAS RN 345363-97-5), isoxachlortole (CAS RN 141112-06-3), isoxaflutole (CAS RN 141112-29-0), α-(cyclopropylcarbonyl)-2-(methylsulfonyl)-β-oxo-4-chloro-benzenepropanenitrile (CAS RN 143701-66-0), and α-(cyclopropylcarbonyl)-2-(methylsulfonyl)-β-oxo-4-(trifluoromethyl)-benzenepropanenitrile (CAS RN 143701-75-1).

The level of expression of the mutant HPPD should be sufficient to reduce substantially (relative to likewise treated plants but lacking the mutant HPPD transgenes) the residue level of parent herbicide throughout the plant tissue. One of ordinary skill in the art will of course understand that certain mutant HPPD enzymes may confer resistance to certain subgroups of HPPD chemistry, and one enzyme may not provide resistance to all HPPDs.

Methods of Use

The present invention further provides a method of selectively controlling weeds at a locus comprising crop plants and weeds, wherein the plants are obtained by any of the methods of the current invention described above, wherein the method comprises application to the locus of a weed controlling amount of one or more herbicides. Any of the transgenic plants described herein may be used within these methods of the invention. The term "locus" may include soil, seeds, and seedlings, as well as established vegetation. Herbicides can suitably be applied pre-emergence or post-emergence of the crop or weeds.

The term "weed controlling amount" is meant to include functionally, an amount of herbicide which is capable of affecting the growth or development of a given weed. Thus, the amount may be small enough to simply retard or suppress the growth or development of a given weed, or the amount may be large enough to irreversibly destroy a given weed.

Thus, the present invention provides a method of controlling weeds at a locus comprising applying to the locus a weed-controlling amount of one or more herbicides, where the locus comprises a transgenic plant that has been transformed with a nucleic acid molecule encoding a mutant HPPD polypeptide or variant thereof that confers resistance or tolerance to HPPD herbicides, alone or in combination with one or more additional nucleic acid molecules encoding polypeptides that confer desirable traits. In one embodiment, the desirable trait is resistance or tolerance to an herbicide, including, for example, herbicides selected from the group consisting of an HPPD inhibitor, glyphosate, and glufosinate. In another embodiment, the locus comprises a transgenic plant that has been transformed with any combination of nucleic acid molecules described above, including one or more nucleic acid molecules encoding a mutant HPPD polypeptide or variant thereof that confers resistance or tolerance to an herbicide in combination with at least one, at least two, at least three, or at least four additional nucleic acid molecules encoding polypeptides that confer desirable traits.

In one embodiment, the present invention provides transgenic plants and methods useful for the control of unwanted plant species in crop fields, wherein the crop plants are made resistant to HPPD chemistry by transformation to express genes encoding mutant HPPD polypeptides, and where an HPPD herbicide is applied as an over-the-top application in amounts capable of killing or impairing the growth of unwanted plant species (weed species, or, for example, carry-over or "rogue" or "volunteer" crop plants in a field of desirable crop plants). The application may be pre- or post emergence of the crop plants or of the unwanted species, and may be combined with the application of other herbicides to which the crop is naturally tolerant, or to which it is resistant via expression of one or more other herbicide resistance transgenes. See, e.g., U.S. App. Pub. No. 2004/0058427 and PCT App. Pub. No. WO 98/20144.

In another embodiment, the invention also relates to a method of protecting crop plants from herbicidal injury. In the cultivation of crop plants, especially on a commercial scale, correct crop rotation is crucially important for yield stability (the achievement of high yields of good quality over a long period) and for the economic success of an agronomic business. For example, across large areas of the main maize-growing regions of the USA (the "central corn belt"), soya is grown as the subsequent crop to maize in over 75% of cases. Selective weed control in maize crops is increasingly being carried out using HPPD inhibitor herbicides. Although that class of herbicides has excellent suitability for that purpose, it can result in agronomically unacceptable phytotoxic damage to the crop plants in subsequent crops ("carry-over" damage). For example, certain soya varieties are sensitive to even very small residues of such HPPD inhibitor herbicides. Accordingly, the herbicide resistant or tolerant plants of the invention are also useful for planting in a locus of any short term carry-over of herbicide from a previous application (e.g., by planting a transgenic plant of the invention in the year following application of an herbicide to reduce the risk of damage from soil residues of the herbicide).

The following examples are provided by way of illustration, not by way of limitation.

EXAMPLES

Example 1

Cloning, Expression and Assay of *Avena*-Derived HPPD SEQ ID NO:14 and Determination of kcat, $Km_{HPP}$ and Ki (kon and koff) Values Versus Various HPPD Herbicides The DNA sequence (SEQ ID NO:1) synthesised by GeneArt (Regensburg, Germany) encoding an HPPD derived from *Avena sativa* (SEQ ID NO:14) was cloned into pET24a and expressed in *E. coli* BL21(DE3) with 50 µg/ml kanamycin selection as described in PCT App. Pub. No. WO 02/46387. Overnight cultures grown at 30° C. were used to inoculate 3×1 liter LB in shake flasks at a ratio of 1:100. Cultures were grown at 37° C., 220 rpm, until an $A^{1cm}$600 nm of 0.6-0.8 was reached, the temperature decreased to 15° C. and induced with 0.1 mM IPTG. Cultures were grown overnight, and cells harvested after 15 min centrifugation at 10,000 g. Cells were stored at −20° C. until extraction. A cell pellet from 3 liters of shake flask culture (~12 g) was thawed in extraction buffer (50 mM Tris, 10 mM sodium ascorbate, 2 mM DTT, 2 mM AEBSF, 10 µM trypsin inhibitor, 1 mM EDTA, pH 7.66) at a ratio of 1 ml buffer:1 g cell paste. Extract was passed through the cell disrupter at 30,000 psi, and centrifuged at 50,000 g for 25 min. at 4° C. Optionally the extract is buffer exchanged down Sepadex G25. Supernatants were beaded in liquid nitrogen and stored at −80° C. Levels of HPPD expression were estimated by Western blot analysis and using purified *Avena* (1-10 ng) as standard. Extracts were diluted 1:6000 and 1-10 ul were loaded onto 12% SDS PAGE. In addition, expression was quantified by comparing induced and uninduced SDS PAGE with COOMASSIE® (Imperial Chemicals Industries, Ltd., London UK) staining. Gels were blotted onto PVDF membrane and Western blots carried out using rabbit anti-wheat HPPD (1:6600) serum as primary antibody and goat anti-rabbit FITC-linked antibodies (1:600) as secondary. Detection of bands was carried out by scanning on a Fluorimager™ 595 (GE Healthcare Ltd, Buckinghamshire UK) and peak quantification was carried out by using ImageQuant™ (GE Healthcare Ltd, Buckinghamshire UK). Plasmid DNA was reisolated from all transformed strains and the DNA sequence across the coding region confirmed.

By Western, the expression level of SEQ ID NO:14 polypeptide expressed in the *E. coli* extract was estimated to be about 10-14 mg/ml. out of a total soluble protein concentration of 33.5 mg/ml.

The concentration of active HPPD in the extract was also more accurately estimated by active site titration. For example a range of volumes of extract (typically 0-20 ul) were added to 50 mM BisTrisPropane buffer at pH7.0 and at 25° C. containing 25 mM Na ascorbate, 4 µg/ml bovine catalase and 3 nmoles of $^{14}$C-labelled compound of Structure A (1.81 GBq/mmol), in a total final assay volume of 425

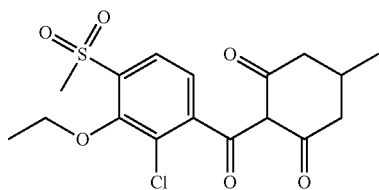

Structure A

The radiolabel protein binding reaction was quenched after 3 minutes by the addition of 100 µl of 1 mM 'cold' Structure A. Protein was exchanged into 50 mM BisTrisPropane buffer at pH 7.0 containing 0.1M KCl by rapid chromatography down a NAPS G25 Sephadex column (GE Healthcare Ltd, Buckinghamshire UK) and $^{14}$C bound to protein fractions measured in Optiphase scintillant using a Tri-Carb 2900TR scintillation counter (Perkin Elmer, Wellesley, Mass.). The HPPD binding site concentration in the extract was calculated from the titration as described in PCT Patent App. Pub. No. WO 02/46387 and was estimated as 94.9, 78.3, and 82.3 (average 85.2) µM in one extract and 47.2 µM in another example.

In an alternate method, the active site titre was calculated on the basis of an activity-based assay titration carried out by pre-incubating various ratios of extract and solutions of Structure A in order to achieve accurate titration of the active site, followed by rapid dilution into assay solution containing 100-200 µM pHPP for immediate assay by HPLC/UV quantitation of homogentisate formation after 30-40 s (i.e., a time sufficiently short that inhibitor dissociation and association does not significantly occur on the timescale of the assay) as described below.

The $Km_{HPP}$ and kcat values of the expressed HPPD were estimated on the basis of assays carried out at 25° C. in solutions of 50 mM BisTrisPropane buffer at pH 7.0 containing 25 mM Na ascorbate, 4 µg/ml bovine catalase (Sigma, St. Louis, Mo.), and a range of concentrations (typically 0.5-10× Km) of 4-hydroxyphenylpyruvate. Typically assays, in a final volume of 110 µl were started with the addition of enzyme and accurately stopped after 20 or preferably 10 seconds with whirlimixed addition of 20 µl 25% perchloric acid. The assay solution was transferred to Chromacol 03-CVG HPLC vials, sealed and the amount of homogentisate formed in a 40 µl aliquot determined by injection onto a reverse phase Aqua C18 5µ75×4.6 mm HPLC column running 5.5% acetonitrile 0.1% TFA (Buffer A) at 1.5 ml/min. The column was eluted at 1.5 ml/minute using a 2 minute wash in buffer A, followed by a 2 minute wash in a 30/70 mixture of buffer A and 100% Acetonitrile, and a further 3.5 minute wash in buffer A. The elution of homogentisate was monitored by UV at 292 nm and the amount formed in each reaction quantified by comparison with a standard calibration curve.

Km and Vmax values were determined (for example FIG. 1) using a non linear least squares fit using Grafit 4™ software (Erithacus Software, Middlesex, UK). Kcat values were determined by dividing the maximum rate, Vmax expressed in nmol/second by the number of nmoles of HPPD enzyme (based on the concentration determined by active-site titration).

From one set of separate experiments similar to those that produced the data shown in FIG. 1, on one extract of HPPD SEQ ID NO:14 the Km value was estimated as 6.17, 4.51, 6.09, 6.13, 4.37, 4.62, 5.41, 5.13 and 6 µM (Km average=5.38 µM). The corresponding kcat values were 4.92, 6.25, 7.08, 6.26, 5.5, 6.77, 6.89, 7.12 and 7.39 s$^{-1}$ (kcat average=6.46 s$^{-1}$). Note that for this calculation and, standardly herein, Mr was taken to be ~94 kD and one active-site per dimer was assumed (i.e., half sites activity as well as inhibitor binding; see Garcia et al. (2000 Biochemistry, 39:7501-7507; Hawkes "Hydroxyphenylpyruvate Dioxygenase (HPPD)—The Herbicide Target." In Modern Crop Protection Compounds. Eds. Krämer and Schirmer. Weinheim, Germany: Wiley-VCH, 2007. Ch. 4.2, pp. 211-220). If the alternate assumption of one active site per monomer had been assumed then calculated kcat values would have been correspondingly halved.

On rates (governed by an association rate constant, kon) for the formation of the enzyme:inhibitor complexes, EI and off rates (governed by a dissociation rate constant, koff) were determined by methods known in the art and essentially as described in Hawkes et al. (2001) Proc. Bright. Crop. Prot. Conf. Weeds, 2:563-568 and in PCT Patent App. Pub. No. WO 02/46387).

For example, on rates were measured by, at zero time, adding ~60 pmoles HPPD to 50 mM BisTrisPropane buffer at pH7.0 and at 25° C. containing 25 mM Na ascorbate, 4 µg/ml bovine catalase (Sigma, St. Louis, Mo.) and an excess (~300 pmoles) of $^{14}$C inhibitor in a total assay volume of 425 µl and, at various time points (0-180 s), quenching the radiolabel binding reaction by addition and rapid mixing of 100 µl 'cold' 1 mM structure A. Protein samples quenched at different times were then exchanged into 50 mM BisTrisPropane buffer at pH 7.0 containing 0.1M KCl by rapid chromatography down a NAPS G25 Sephadex column (GE Healthcare Ltd, Buckinghamshire UK) and the amount of $^{14}$C bound to protein fractions quantified in Optiphase scintillant using a Tri-Carb 2900TR scintillation counter (Perkin Elmer, Wellesley, Mass.). The data were fit according to the scheme below in order to derive the value of the apparent second order rate constant, k2, governing the association rate of enzyme and radiolabelled inhibitor. A range of enzyme and inhibitor concentrations were used. Optionally, the rate constant may be derived from similar experiments where enzyme (at ~0.05-0.2 µM binding sites) and, in this case, unlabelled, inhibitor (at ~0.5 to 2 µM) are reacted for a range of short times (0-60 s) in 50 mM BisTrisPropane buffer at pH7.0 and at 25° C. containing 25 mM Na ascorbate, 4 µg/ml bovine catalase (Sigma, St. Louis, Mo.) and then quenched by rapid dilution into assay solution containing 100-200 µM HPP for immediate assay by HPLC/UV quantitation of homogentisate formation after 30-40 s (i.e., a time sufficiently short that inhibitor dissociation and association does not significantly occur on the timescale of the assay) as described above. Further example methods are described in PCT Patent App. Pub. No. WO 02/46387.

Off rates (k1 in the scheme below) were derived from exchange rate studies where either the test inhibitor, I, or its exchange partner, J were radiolabelled and the data fit according to the scheme below. As noted in Hawkes et al. (2001) Proc. Bright. Crop. Prot. Conf. Weeds, 2:563-568, HPPD preparations typically appear to contain 15-30% of a more rapidly exchanging (weaker binding) fraction of inhibitor binding sites. This may be a slightly damaged form of the enzyme (it maintains catalytic activity and may have a higher substrate Km) and, except where off rates are so fast that fast and slow exchanging fractions are rendered indistinguishable, off rates always refer to the behaviour of the majorly slower exchanging fraction that represents 70-85% bulk of the HPPD inhibitor binding sites present in the extracts tested.

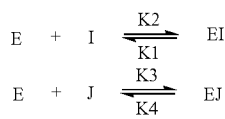

Off rates were determined by preincubating, for example, ~200 pmoles of HPPD binding sites (determined as described above by active site titration in a 3 min reaction with structure A) in 50 mM BisTrisPropane buffer at pH 7.0 and at 25° C. containing 25 mM Na ascorbate, 4 µg/ml bovine catalase (Sigma, St. Louis, Mo.) containing ~1.0 nmole $^{14}C$ inhibitor @25° C. in a total assay volume of 1.3 mls. After 30 minutes the exchange reaction was initiated with addition of 100 µl 1 mM 'cold' structure A with thorough mixing, and, immediately, 150 µl were withdrawn and loaded onto a NAPS column, the protein exchanged into 50 mM BisTrisPropane buffer at pH 7.0 containing 0.1M KCl by rapid (<2 min) chromatography down a NAPS G25 Sephadex column (GE Healthcare Ltd, Buckinghamshire UK) and the amount of $^{14}C$ bound to protein measured by Optiphase scintillant using a Tri-Carb 2900TR scintillation counter (Perkin Elmer, Wellesley, Mass.). Further aliquots were removed and measured in the same way at various times over minutes or hours as required in order to determine the exchange kinetics.

In one variant of the method useful to better distinguish between off rates that were relatively rapid (e.g., where $t^{1\!/\!2}<15$ min at 25° C.) the temperature of the experiment was reduced from 25° C. to ice temperature. In this case, off rates were determined by preincubating ~200 pmoles HPPD in reaction buffer (50 mM BTP pH7, mM Na ascorbate, 4 ug/ml bovine catalase, and 10% glycerol) containing ~1.0 nmoles $^{14}C$ inhibitor at 25° C. in a total assay volume of 1.3 mls. After 30 minutes the reaction vessel was transferred to ice. After a further 10 minutes at ice temperature the exchange reaction was initiated by addition of 100 µl 1 mM Structure A, with thorough mixing, and 150 µl was withdrawn and loaded onto a NAPS column in a cold room at ~5-8° C. in order to quantify the amount of radiolabel remaining bound to the protein at various time from the start of exchange at ice temperature.

Off rates (k1) of HPPD inhibitors that are not available radiolabelled or that present other measurement problems (for example high levels of background non-specific protein-binding which can be measured as radiolabel binding that persists in the presence of high concentrations of 'cold' inhibitor) may be measured indirectly. In this case the enzyme complex (~0.1-0.2 µM) is first formed with the unlabelled inhibitor and then the exchange kinetics derived by chasing it off with high a concentration of $^{14}C$-labelled structure A and monitoring the rate at which the label becomes bound to protein. Structure A is a particularly potent inhibitor with known kinetics and in a 20 fold or more excess will, in equilibrium, >95% occupy the binding sites in exchange competition with the other inhibitors tested here and indeed most other inhibitors (those skilled in the art will of course design the experiment/relative concentrations and fit the data accordingly). Exemplary methods are also described in PCT Patent App. Pub. No. WO 02/46387.

Exemplary on and off rate data (and derived Ki values) were obtained for the *Avena*-derived HPPD SEQ ID NO:11 for the following compounds as follows.

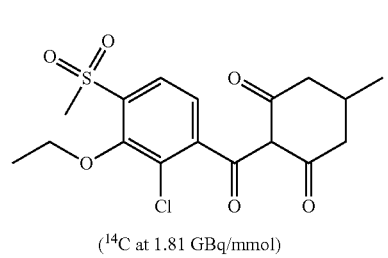

Structure A ($^{14}C$ at 1.81 GBq/mmol)

Off rate (k1=1.67E-05 s$^{-1}$). 25° C., direct, radiochemical method.
On rate (k2=8.50E+04 M$^{-1}$ s$^{-1}$). 25° C., direct radiochemical method.
Kd=1.96E-10 M.
Kd/Km ratio=0.000036

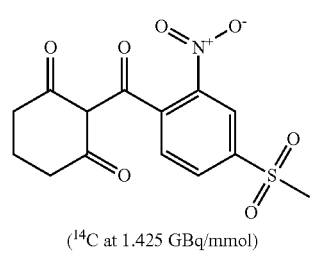

Structure B ($^{14}C$ at 1.425 GBq/mmol)

Off rate k1(av)=8.1 E-04 s$^{-1}$ at 25° C. (individual experiments yielded k1=8.00E-04, 8.88E-04, 7.50E-04 and 8.00E-04 as determined by the direct, radiochemical method). Measured at ice temperature k1=1.21E-05 s$^{-1}$ (individual experiments yielding 1.16E-05 s$^{-1}$, 1.0E-05 s$^{-1\prime}$ 1.2E-05 s$^{-1\prime}$ 1.5E-05 s$^{-1}$) by the direct, radiochemical method.
On rate k2(av)=6.7E+04 s$^{-1}$ M$^{-1}$ at 25° C. (individual experiments yielded k2=6.35E+04, 7.50E+04, 6.2E+04 as determined by the direct radiochemical method). For mesotrione which has a relatively fast off rate estimates for on rate based on the activity-based method were more variable ranging from 4.2E+04 s$^{-1}$ M$^{-1}$, 4.9E+04 s$^{-1}$ M$^{-1}$ to 7.5 E+04 s$^{-1}$ M$^{-1}$ at 25° C.

Kd was thus estimated from the radiochemical data as 1.16E-08 M corresponding to a Kd/Km ratio of 0.00217.

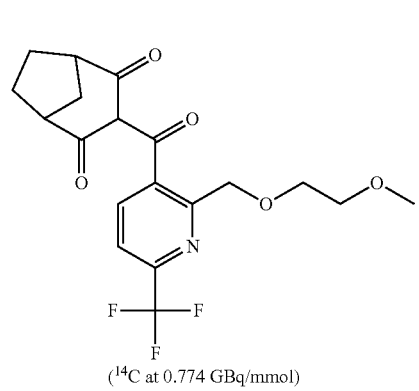

Structure C ($^{14}C$ at 0.774 GBq/mmol)

Off rate k1(av)=7.04 E-05 s$^{-1}$ at 25° C. (individual experiments yielded k1=7.80E-05, 9.17E-05, 4.5E-05, 6E-05, 7 E-05 and 7.80E-05 as estimated by the indirect radiochemical method).

On rate k2=7.50E+03 s$^{-1}$ M$^{-1}$ at 25° C. as estimated by the direct radiochemical method is in good agreement with estimates from the enzyme activity-based method of 7.50E+03 s$^{-1}$ M$^{-1}$, 7.80E+03 s$^{-1}$ M$^{-1}$, 7.60E+03 s$^{-1}$ M$^{-1}$, 7.20E+03 s$^{-1}$ M$^{-1}$ and 1.0E+04 s$^{-1}$ M$^{-1}$ at 25° C.

Based on the radiochemical method the estimate of Kd=9.4 E-09M.

Therefore the estimate of Kd/Km ratio is then=0.0017.

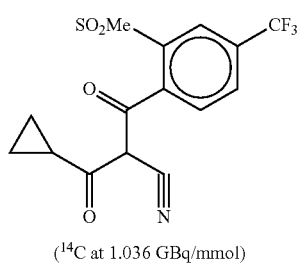

Structure D ($^{14}$C at 1.036 GBq/mmol)

Off rate k1=3.96E-05 s$^{-1}$ at 25° C. as determined using the direct, radiochemical method (individual measurements of 4.17E-05 s$^{-1}$ and 3.75E-05 s$^{-1}$).

On rate k2=3.20E+04 M$^{-1}$ s$^{-1}$ at 25° C. as determined by the direct radiochemical method. This is in fair agreement with estimates from the activity based method for on rate of 3.20E+04 M$^{-1}$ s$^{-1}$ and 5.7E+04 M$^{-1}$ s$^{-1}$.

Based on the radiochemical methods the estimate of Kd=1.23E-9 M.

The estimate of Kd/Km ratio=0.00023.

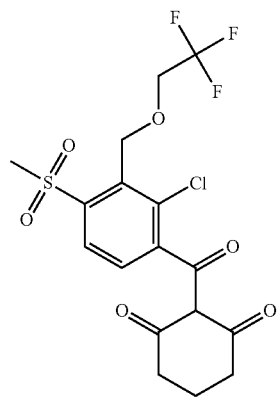

Structure E

Off rate k1=4.17E-05 s$^{-1}$ at 25° C. as determined by the indirect, radiochemical method. (individual measurements of 5.50E-05 s$^{-1}$ and 2.85E-05 s$^{-1}$).

On rate k2=1.30E+05 M$^{-1}$ s$^{-1}$ at 25° C. as determined by the direct non-radiochemical method.

The estimate of Kd=3.21E-10M.

The estimate of Kd/Km ratio=0.000059.

Example 2

Cloning, Expression and Assay of Further Variants of Avena-Derived HPPDs SEQ ID NOS:12-20 and Determination of kcat, Km$_{HPP}$ and Ki (kon and koff) Values Versus Various HPPD Herbicides DNA sequences corresponding to SEQ ID NOS:2-14, encoding HPPD polypeptides corresponding to SEQ ID NOS:15-26 derived from *Avena sativa*, were synthesized by GeneArt (Regensburg, Germany), cloned into pET24a, and expressed in *E. coli* BL21(DE3) with 50 μg/ml kanamycin selection as described in PCT App. Pub. No. WO 02/46387. Cells were grown, protein extracts were prepared, and HPPD active site titres and kinetic measurements (of kcat, KmHPP, k1, k2 and Ki values) were carried out as described in Example 1.

Within the present example, the following HPPD sequences were used:

HPPD SEQ ID NO:15 was changed relative to SEQ ID NO:14 by the substitution of A for Q within the sequence motif GVQHIA (residues 1-6 of SEQ ID NO:55).

HPPD SEQ ID NO:16 was changed relative to SEQ ID NO:14 by the substitution of G for Q within the sequence motif GVQHIA (residues 1-6 of SEQ ID NO:55).

HPPD SEQ ID NO:17 was changed relative to SEQ ID NO:14 by the substitution of S for Q within the sequence motif GVQHIA (residues 1-6 of SEQ ID NO:55).

HPPD SEQ ID NO:18 was changed relative to SEQ ID NO:14 by the substitution of T for 1 within the sequence motif SQIQTY (residues 1-6 of SEQ ID NO:53).

HPPD SEQ ID NO:19 was changed relative to SEQ ID NO:14 by the substitution of A for 1 within the sequence motif SQIQTY (residues 1-6 of SEQ ID NO:53).

HPPD SEQ ID NO:20 was changed relative to SEQ ID NO:14 by the substitution of S for 1 within the sequence motif SQIQTY (residues 1-6 of SEQ ID NO:53).

HPPD SEQ ID NO:21 was changed relative to SEQ ID NO:14 by the substitution of V for 1 within the sequence motif SQIQTY (residues 1-6 of SEQ ID NO:53).

HPPD SEQ ID NO:22 was changed relative to SEQ ID NO:14 by the substitution of M for L within the sequence motif SGLNS (residues 5-9 of SEQ ID NO:43).

HPPD SEQ ID NO:23 was changed relative to SEQ ID NO:14 by the substitution of W for A within the sequence motif FAEFT (residues 5-9 of SEQ ID NO:42).

HPPD SEQ ID NO:24 was changed relative to SEQ ID NO:14 by the substitution of M for L within the sequence motif G(I,V)LVDRD (SEQ ID NO:30).

HPPD SEQ ID NO:25 was changed relative to SEQ ID NO:14 by the substitution of A for L within the sequence motif G(I,V)LVDR (residues 1-6 of SEQ ID NO:30).

HPPD SEQ ID NO:26 was changed relative to SEQ ID NO:14 by the substitution of M for L within the sequence motif G(I,V)LVDR (residues 1-6 of SEQ ID NO:30) and by the substitution of M for L within the sequence motif SGLNS (residues 5-9 of SEQ ID NO:43).

Values (generally radiochemically determined) of kon (k2), koff (k1), and Ki (all at 25° C.) were obtained for the HPPDs in the present example versus the various inhibitor structures as shown in Table 3. The values given for the reference SEQ ID NO:14 in Table 3 are the average values from a number of experiments as described above. All of the experiments with the other HPPDs included side by side measurements with SEQ ID NO:14 as a comparative control. Within experiments, the ratios of on and off rates relative to this side by side control were reproducible even where absolute values varied somewhat. Thus the values given in Table 3 for HPPD SEQ ID NOs:15-26 are normalized versus the average control values for HPPD SEQ ID NO:14 according to these observed ratios.

TABLE 3

Summary of Values of kon, koff and Kd for HPPD Variants

| HPPD variant | kon(k2)/s/M | koff(k1)/s | Kd nM |
|---|---|---|---|
| Structure A | | | |
| SEQ ID #14 | 85000 | 1.67E-05 | 0.20 |
| SEQ ID #15 | 35000 | 3.33E-05 | 0.95 |
| SEQ ID #16 | ND | ND | ND |
| SEQ ID #17 | ND | ND | ND |
| SEQ ID #18 | 42000 | 1.67E-05 | 0.40 |
| SEQ ID #19 | ND | ND | ND |
| SEQ ID #20 | ND | ND | ND |
| SEQ ID #21 | 85000 | 1.67E-05 | 0.20 |
| SEQ ID #22 | 85000 | 1.08E-05 | 0.13 |
| SEQ ID #23 | 85000 | 2.83E-05 | 0.33 |
| SEQ ID #24 | 85000 | 2.30E-05 | 0.27 |
| SEQ ID #25 | ND | ND | ND |
| SEQ ID #26 | ND | ND | ND |
| Structure B | | | |
| SEQ ID #14 | 67000 | 8.10E-04 | 11.6 |
| SEQ ID #15 | 70000 | 8.00E-04 | 11.4 |
| SEQ ID #16 | 53000 | 2.00E-03 | 37.7 |
| SEQ ID #17 | 53000 | 1.00E-03 | 18.9 |
| SEQ ID #18 | 35000 | 6.00E-04 | 17.1 |
| SEQ ID #19 | 38000 | 7.50E-04 | 19.7 |
| SEQ ID #20 | 31500 | 9.00E-04 | 28.6 |
| SEQ ID #21 | 70000 | 6.00E-04 | 8.6 |
| SEQ ID #22 | 70000 | 1.20E-03 | 17.1 |
| SEQ ID #23 | 70000 | 7.00E-04 | 10.0 |
| SEQ ID #24 | 70000 | 1.57E-03 | 22.4 |
| SEQ ID #25 | 20000 | 8.00E-04 | 40.0 |
| SEQ ID #26 | 70000 | 3.00E-03 | 42.9 |
| Structure C | | | |
| SEQ ID #14 | 7500 | 7.04E-05 | 9.4 |
| SEQ ID #15 | 7500 | 1.13E-04 | 17.7 |
| SEQ ID #16 | 4500 | 1.20E-04 | 26.7 |
| SEQ ID #17 | 9400 | 6.65E-05 | 7.1 |
| SEQ ID #18 | 7500 | 9.00E-05 | 11.9 |
| SEQ ID #19 | 7500 | 6.60E-05 | 8.9 |
| SEQ ID #20 | 10100 | 6.60E-05 | 6.6 |
| SEQ ID #21 | 7500 | 9.00E-05 | 11.9 |
| SEQ ID #22 | 4400 | 9.00E-05 | 23.9 |
| SEQ ID #23 | 7500 | ND | ND |
| SEQ ID #24 | 4900 | 7.82E-05 | 16.0 |
| SEQ ID #25 | 4800 | 1.13E-04 | 23.0 |
| SEQ ID #26 | ND | 9.00E-05 | ND |
| Structure D | | | |
| SEQ ID #14 | 32000 | 3.96E-05 | 1.2 |
| SEQ ID #15 | ND | 2.37E-05 | ND |
| SEQ ID #16 | ND | ND | ND |
| SEQ ID #17 | ND | ND | ND |
| SEQ ID #18 | ND | 3.96E-05 | ND |
| SEQ ID #19 | ND | ND | ND |
| SEQ ID #20 | ND | ND | ND |
| SEQ ID #21 | ND | 3.96E-05 | ND |
| SEQ ID #22 | ND | 2.37E-05 | ND |
| SEQ ID #23 | ND | 2.37E-05 | ND |
| SEQ ID #24 | 32000 | 9.18E-05 | 2.9 |
| SEQ ID #25 | ND | ND | ND |
| SEQ ID #26 | ND | ND | ND |

Figure 4A:
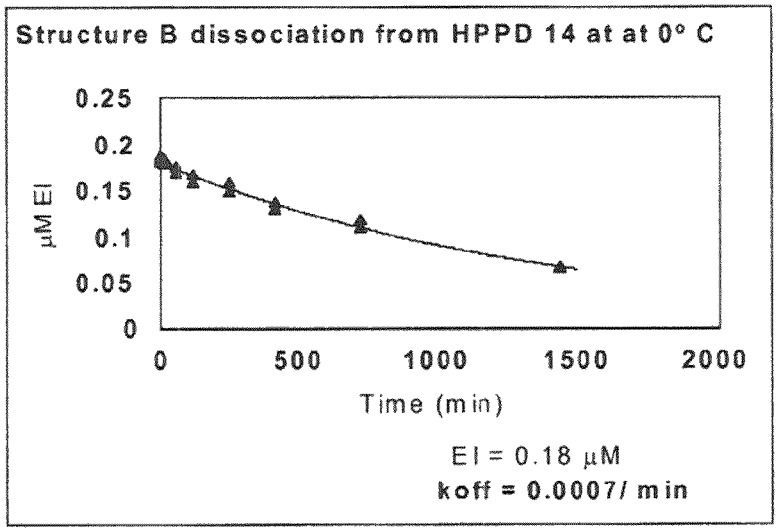
FIGS. 4A-4C show off rate determinations at ice temperature for complexes of structure B with the HPPD polypeptides corresponding to the amino acid sequences set forth in SEQ ID NO:14 (FIG. 4A), 24 (FIG. 4B), and 26 (FIG. 4C).
Figure 4B:
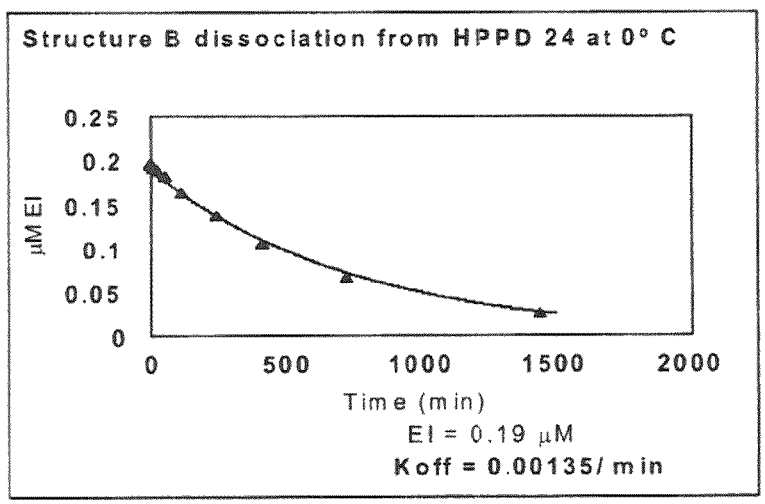
Figure 4C:
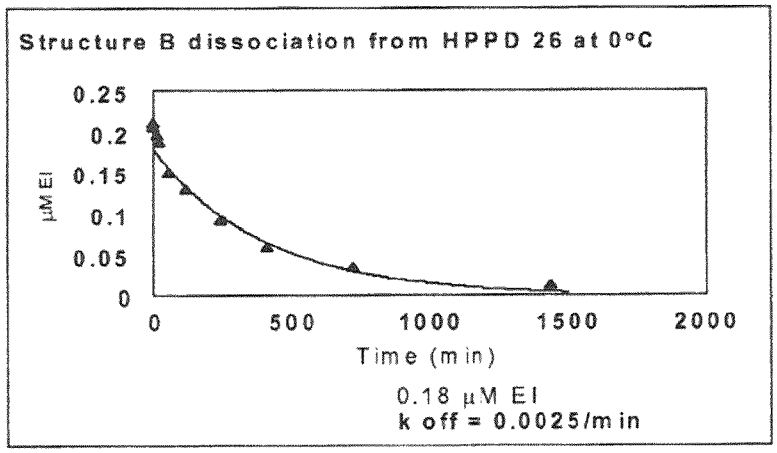

For example, the off rate of mesotrione (structure B) from HPPD SEQ ID NO:14 was clearly differentiated from that of SEQ ID NO:24 (see FIGS. 4A-4C) with the goodness of fits being sensitive to small changes in koff. From these data it can be seen that mesotrione dissociated about twice as fast from HPPD SEQ ID NO:26 as from HPPD SEQ ID NO:24, and from HPPD SEQ ID NO:24 about twice as fast as from HPPD SEQ ID NO:14. Generally the absolute estimates of koff obtained from the fits to the data were reproducible to within +/-10% and usually better.

When off rates became relatively fast (t½<10 minutes) it was also useful to make comparative measurements at ice temperature in order to more accurately confirm the differential between one HPPD and another. Thus, for example, at ice temperature, mesotrione dissociation from HPPD SEQ NO:14 was governed by a rate constant, koff, of 1.16E-05 s$^{-1}$ (much slower than the value of 8.1 E-04 s$^{-1}$ estimated at 25° C.) whereas for SEQ ID NOS:22, 24 and 26, the corresponding mesotrione off rates at ice temperature were 2.17E-05 s$^{-1}$, 2.25E-05 s$^{-1}$ and 4.17E-05 s$^{-1}$; these values being in good proportionate agreement with those at 25° C. (See Table 3).

A number of conclusions were derived from the data in Table 3. The properties of HPPDs SEQ ID NOS:15-17 indicated that certain substitutions for asparagine (Q) within the amino acid sequence GVQHI provided significant improvements relative to HPPD SEQ ID NO:14 in tolerance (slower values of kon and/or faster values of koff), with respect to, for example, Structures A, B and C.

Data from HPPDs SEQ ID NOS:18-21 indicated that certain substitutions for isoleucine (I) within the amino acid sequence SQIQTY provided significant improvements relative to HPPD SEQ ID NO:14 in tolerance (mainly via slower values of kon), with respect to, for example, Structures A and B.

Data from HPPD SEQ ID NO:22 indicated that certain substitutions for leucine (L) within the amino acid sequence ESGLN provided significant improvements relative to HPPD SEQ ID NO:14 in tolerance (mainly via faster values of koff) with respect to, for example, Structures B and C.

Data from HPPD SEQ ID NO:23 indicated that certain substitutions for alanine (A) within the amino acid sequence EFAEF provided significant improvements relative to HPPD SEQ ID NO:14 in tolerance (mainly via faster values of koff) with respect to, for example, Structure A.

Data from HPPDs SEQ ID NOS:24 and 25 indicated that certain substitutions for leucine (L) within the amino acid sequence G(I,V)LVDRD provided significant improvements relative to HPPD SEQ ID NO:14 in tolerance (via faster values of koff and/or slower values of kon) with respect to, for example, Structure A, Structure B, Structure C and Structure D.

Data from HPPD SEQ ID NO:26 indicated that the combination of certain substitutions for leucine (L) within the amino acid sequence ESGLN with certain substitutions for leucine (L) within the amino acid sequence G(I,V)LVDRD provided yet further significant improvements relative to HPPD SEQ ID NO:14 (and over and above the effect of either single change) in tolerance (mainly via faster values of koff) with respect to, for example, Structures B.

Again, as described for Example 1, kcat and Km values were determined for a number of the HPPDs of the invention expressed in extracts and the values are depicted in Table 4.

TABLE 4

Km and kcat Values of Various HPPDs

| HPPD variant | Km uM | kcat s-1 | kcat/Km uM-1s-1 |
|---|---|---|---|
| SEQ ID #14 | 5.38 | 6.46 | 1.2 |
| SEQ ID #18 | 35.98 | 17.94 | 0.50 |
| SEQ ID #21 | 5.98 | 5.47 | 0.91 |
| SEQ ID #22 | 12.43 | 5.79 | 0.46 |
| SEQ ID #24 | 4.74 | 4.35 | 0.92 |
| SEQ ID #26 | 10.58 | 4.05 | 0.38 |

A number of the HPPD variants had low Km values similar to HPPD SEQ ID NO:14 and higher values of Ki/Km with respect to the various HPPD herbicides and, thus, overexpression in plants expected to provide enhanced herbicide tolerance to these herbicides. For example, HPPD SEQ ID NO:24 was twice as resistant to mesotrione as was HPPD SEQ ID NO:14 since it exhibited a Ki/Km ratio of 0.0047 as compared with 0.0021.

In addition, all of the above sequences as well as libraries of variants mutated at the same amino positions that showed altered and enhanced levels of herbicide tolerance are useful to be included in mutagenesis and shuffling processes in order to generate yet further shuffled and mutated HPPDs useful as transgenes for conferring herbicide tolerance. For example, the mutants disclosed in Table 5 are useful for generating a herbicide tolerant HPPD mutant polypeptide and for inclusion in recombination reactions to generate further HPPDs.

TABLE 5

Examples of Mutations Useful in Herbicide Tolerant HPPD Polypeptides

| Mutation | Amino acid region of SEQ ID NO: 14 |
|---|---|
| K411L | GGFGKGNFS |
| K411T | GGFGKGNFS |
| K411S | GGFGKGNFS |
| K411M | GGFGKGNFS |
| K411A | GGFGKGNFS |
| K411E | GGFGKGNFS |
| K411V | GGFGKGNFS |
| M325L | GFEFMAPPQ |
| L271I | VLLPLNEPV |
| L271M | VLLPLNEPV |
| L271V | VLLPLNEPV |
| G408A | GGCGGFGKG |
| G408S | GGCGGFGKG |
| G408T | GGCGCFGKG |
| V258M | GLNSVVLAN |
| V258I | GLNSVVLAN |
| V258A | GLNSVVLAN |
| V258K | GLNSVVLAN |
| V217I | RFDHVVGNV |
| V217A | RFDHVVGNV |
| V217M | RFDHVVGNV |
| V217C | RFDHVVGNV |
| L271I | VLLPLNEPV |
| L271M | VLLPLNEPV |
| L271V | VLLPLNEPV |
| A326S | FEFMAPPQA |
| A326K | FEFMAPPQA |
| A326P | FEFMAPPQA |

TABLE 5-continued

Examples of Mutations Useful in Herbicide Tolerant HPPD Polypeptides

| Mutation | Amino acid region of SEQ ID NO: 14 |
|---|---|
| A326D | FEFMAPPQA |
| A326R | FEFMAPPQA |
| A326N | FEFMAPPQA |
| A326Y | FEFMAPPQA |
| A326H | FEFMAPPQA |
| I370V | VLLQIFTKP |
| Y287F | QIQTYLEYH |
| G254S | TTESGLNSV |
| G254A | TTESGLVSV |
| E416Q | GNFSELFKS |
| I339L | GVRRIAGDV |
| L269M | EAVLLPLNE |
| L269F | EAVLLPLNE |
| S420A | ELFKSIEDY |
| I372S | LQIFTKPVG |
| Y172V | EVELYGDVV |
| I299M | GVQHIALAS |

As another example, the mutants disclosed in Table 6 are also useful for generating a herbicide tolerant HPPD mutant polypeptide and for inclusion in recombination reactions to generate further HPPDs.

TABLE 6

Examples of Mutations Useful in Herbicide Tolerant HPPD Polypeptides

| Mutation | Amino acid region of SEQ ID NO: 14 |
|---|---|
| K411L | GGFGKGNFS |
| K411T | GGFGKGNFS |
| K411S | GGFGKGNFS |
| K411M | GGFGKGNFS |
| K411A | GGFGKGNFS |
| K411E | GGFGKGNFS |
| K411V | GGFGKGNFS |
| M325L | GFEFMAPPQ |
| L271I | VLLPLNEPV |
| L271M | VLLPLNEPV |
| L271V | VLLPLNEPV |
| G408A | GGCGGFGKG |

TABLE 6-continued

Examples of Mutations Useful in Herbicide Tolerant HPPD Polypeptides

| Mutation | Amino acid region of SEQ ID NO: 14 |
|---|---|
| G408S | GGCGGFGKG |
| G408T | GGCGGFGKG |
| V258M | GLNSVVLAN |
| V258I | GLNSVVLAN |
| V258A | GLNSVVLAN |
| V258K | GLNSVVLAN |
| V217I | RFDHVVGNV |
| V217A | RFDHVVGNV |
| V217M | RFDHVVGNV |
| V217C | RFDHVVGNV |
| L271I | VLLPLNEPV |
| L271M | VLLPLNEPV |
| L271V | VLLPLNEPV |
| A326S | FEFMAPPQA |
| A326K | FEFMAPPQA |
| A326P | FEFMAPPQA |
| A326D | FEFMAPPQA |
| A326R | FEFMAPPQA |
| A326N | FEFMAPPQA |
| A326Y | FEFMAPPQA |
| A326H | FEFMAPPQA |
| I370V | VLLQIFTKP |
| Y287F | QIQTYLEYH |
| G254S | TTESGLVSV |
| G254A | TTESGLNSV |
| E416Q | GNFSELFKS |
| I339L | GVRRIAGDV |
| L269M | EAVLLPLNE |
| L269F | EAVLLPLNE |
| S420A | ELFKSIEDY |
| I372S | LQIFTKPVG |
| Y172V | EVELYGDVV |
| I299M | GVQHIALAS |

Table 7 summarises data from kinetic studies of a range of mutants of HPPD SEQ ID NO:14 expressed relative to the control, 'none', meaning non-mutated HPPD SEQ ID NO:14. Experiments were carried out as described for Table 4. 'Sulc' denotes sulcotrione and 'nd,' means 'no data'. For V217I, L271I, L271V, V258M and A326R, the relative values of kcat were estimated from comparisons of the initial rates in cell extracts of similarly prepared and expressed HPPDs in conventional enzyme activity assays at pH 7.0, 25° C. and at a substrate concentration of 120 µM HPP. V217I, V258M and A326R, M325L and L358M mutants of SEQ ID NO:14 are active HPPD enzymes that offer some resistance to sulcotrione, and may also offer resistance to B. K411T offers significant resistance to E and especially since the greater than 5× increase in Kd to this herbicide comprises mainly an improvement in off rate (3.5×) rather than in on rate. L358M, M325L and K411T all offer improvements with respect to D. For herbicide tolerance L271I and L271V appear to offer significant advantages in kcat over unmutated enzyme.

TABLE 7

Relative Kinetics of Various Mutants of SEQ ID NO: 14

| | chemical | | | | | | | | Rate | |
|---|---|---|---|---|---|---|---|---|---|---|
| | B | | sulc | C | | D | | E | | |
| mutation | koff | Kd | Kd | koff | Kd | koff | Kd | koff | Kd | kcat | kcat/Km |
| none | 1 | 1 | 1 | 1 | 1 | 1 | 1 | 1 | 1 | 1 | 1 |
| L358M | 2 | 2 | 2 | 1.1 | 1.7 | 2.3 | 2.3 | 1.2 | 1.5 | 0.7 | 0.8 |
| M325L | 1.1 | 1.1 | 1.3 | 1 | 1 | 1.2 | 1.4 | 1 | 1 | 1.2 | 1.3 |
| V217I | 1.5 | 1.5 | 1.3 | 1.1 | 1.1 | 1 | 1 | 1 | 1 | 1.1 | 1.1 |
| V258M | nd | Nd | 1.2 | nd | nd | nd | nd | nd | nd | 1 | nd |
| L281I | nd | Nd | 0.8 | nd | nd | nd | nd | nd | nd | 1.7 | nd |
| L281V | nd | Nd | 0.6 | nd | nd | nd | nd | nd | nd | 2 | nd |
| A326R | 1.7 | 1.7 | 1.6 | 0.9 | 0.9 | 1.4 | 1.4 | 1.3 | 1.6 | 1.2 | 1.4 |
| K411T | 0.3 | 0.5 | 0.9 | 1 | 1.1 | 1.2 | 3.6 | 3.5 | 5.4 | 1 | 0.4 |

It will be appreciated that the majority of substitutions to amino acids within the highly conserved active-site region of HPPD and that lie within 8° A of the atoms of bound mesotrione (according to interpretation of published X Ray crystallographic data of the maize and *arabidopsis* HPPDs and homology model building to oat HPPD) result in disabled or only partially functional enzymes. From sequence alignments of (active) HPPD sequences in the database, about 60 single or double mutants of SEQ ID NO:14 were selected as amenable to changes in some residues without loss of enzyme activity (on the basis that they were changes that represented some of the spread of sequence variation found amongst natural HPPDs at these positions). These mutants were made, grown, the HPPDs expressed and extracts prepared and tested for their catalytic activity and resistance to mesotrione (relative to the control, unmutated SEQ ID NO:14). Even amongst this privileged set the majority exhibited significantly impaired catalytic activity and/or were significantly more sensitive to sulcotrione than the control. Y287F and I370V were neutral mutations with similar (within 20%) values of kcat and resistance to sulcotrione as the unmutated enzyme. Amongst a further set of about 70 mutants encompassing residues as far as 10° A from the atoms of the bound inhibitors further such neutral mutations (with respect to SEQ ID NO:14) were G254S, G254A, E416Q, V258M, V258I, V258A, V258K, S415K, S415Q, I421L, A326S, L269M, L269F, S420A, T372S, Y172V and I299M. These further mutations can all be optionally combined with the resistance conferring mutations to produce catalytically active variants of HPPD herbicide resistant enzymes of the current invention.

A further mutant of HPPD SEQ ID NO:14, G408A, exhibited inhibition kinetics in respect of B and C showing that this mutant was relatively resistant to inhibition by these compounds. The timecourses of inhibition were not straightforward and could not be fit to the kinetic model described above. The experimental method used was similar to that described above for measuring inhibitor-binding on rates by monitoring enzyme activity. The time courses of inhibition are depicted in FIGS. 10A-10D. Enzyme at about 75 nM was incubated with inhibitor at 0.15 or 0.6 μM for various times up to 260s and then immediately assayed over a 150 s period following addition of 115 μM HPP (and thus with [5] at ~30×Km also dramatically slowing any further inhibitor binding). In the case of the mutant there appeared to be an initial rapid phase of inhibition which then slowed to leave the enzyme only partly inhibited. In the case of control enzyme inhibition proceeded to (or was on course towards) full inhibition. Although note that in the case of inhibition of the control enzyme by compound B did not quite reach 100%. The ~8% residual activity in this case was an artifact of the method due to the relatively fast off rate of compound B which allowed some activity to recover during the 150 s assay used to monitor the progress of the reaction between enzyme and inhibitor. This artifact is negligible with slower dissociating inhibitors such as C. Over the time of the experiment and at 0.6 μM B, inhibition of mutant G408A appeared to level off to a residual activity of about 35%. It appeared that this was not due to an even faster off rate for B from G208A than from the control enzyme since, at ice temperature, the radiochemically determined off rate of B from G408A appeared indistinguishable from the rate observed with the control SEQ ID NO:14 HPPD. Mutant G408 also exhibited a similar kcat and kcat/Km to SEQ ID NO: 14 HPPD. Whatever the explanation both B and C appeared to inhibit the G408A mutant HPPD to a lesser extent than the control enzyme. It is also notable the G408A activity appeared unstable since the control activity in the absence of inhibitor declined over the course of the experiment. The addition of inhibitor appeared to arrest this decline in activity and in further experiments it was confirmed that mutant G408A activity was unstable in the absence of inhibitor or substrate but was stabilized by inhibitor and appeared no less stable than wild type enzyme over extended assay time courses in the presence of substrate or when partially inhibited by HPPD herbicide. Thus, despite some instability, mutant G408A is useful alone or in combination with other mutations to provide useful herbicide tolerance while herbicide is present in the plant tissues where it is expressed.

Figure 5:
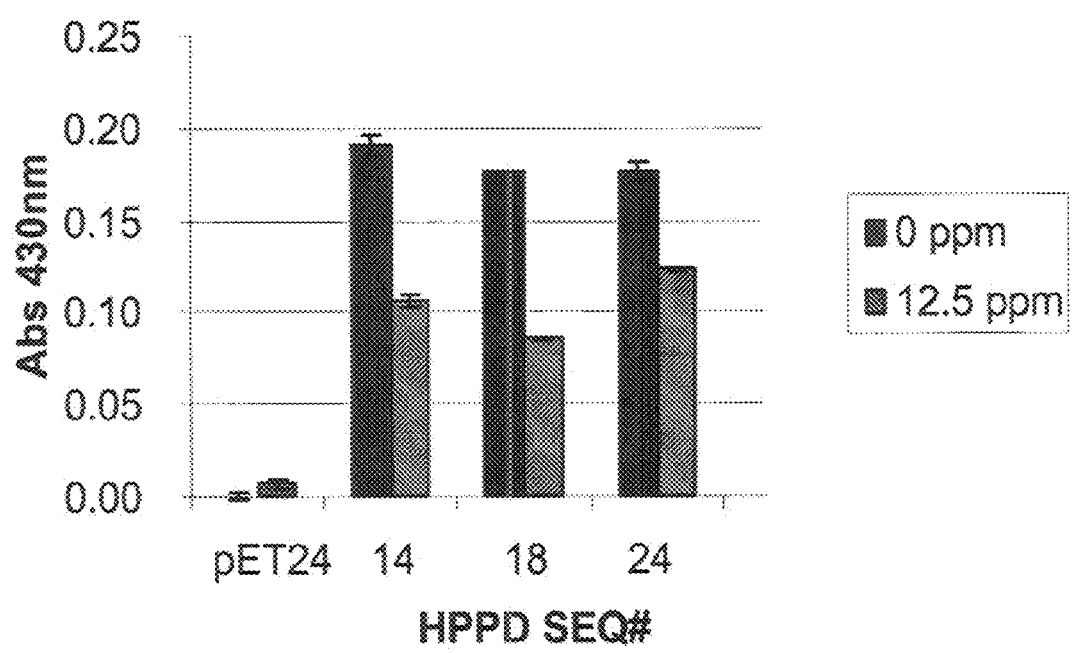
FIG. 5 shows mesotrione inhibition of pyomelanin formation by *E. coli* BL21 expressing different variants of HPPD. Left bar=(error range for n=3) average A 430 nm with zero mesotrione present in the medium and right bar=(n=3) average A 430 nm with 12.5 ppm present in the medium. Control is pET24 empty vector where no HPPD is expressed.

Aside from enzyme kinetic experiments, enhanced resistance to HPPD herbicides was further demonstrated when the HPPDs of the current invention were expressed in *E. coli* and the comparative herbicide resistances of the various HPPDs assessed visually via the production of pyomelanin. For example HPPD SEQ ID NO:14 and HPPD SEQ ID NO:24 were expressed from a pET24 vector in *E. coli* BL21 cells. Grown without addition of IPTG there was sufficient expression of HPPD for cultures to slowly turn brown due to the production of pyomelanin pigment (which results from autooxidation of HPPD-derived homogentisate). Cells were grown from a 10% starting inoculum into 0.5 ml of L-broth containing 50 μg of kanamycin ml$^{-1}$ in 45 well plates for 48-96 h at 15° C. Typically pyomelanin colour in the medium was read (at 430 nm) after ~72 h. It was noted that addition of 12.5 ppm mesotrione caused significantly proportionately less inhibition of pyomelanin colour development in the cells expressing HPPD SEQ ID NO:24 than expressing HPPD SEQ ID NO:14. FIG. 5 compares the absorbance of the medium obtained after 72 h in side by side triplicate grows of *E. coli* expressing HPPD SEQ ID NOS:14, 18, and 24 all grown in the same plate.

Cells expressing HPPD SEQ ID NO:24, which exhibited the highest ratio of Ki/Km, consistently exhibited the least difference in colour between cells grown with and without 12.5 ppm mesotrione present in the medium. The same was seen when the mesotrione was replaced with 20 ppm sulcotrione (data not shown) indicating that SEQ ID NO 24 offers enhanced tolerance to sulcotrione as well as to mesotrione. Similarly, cells expressing mutant G408A also exhibitied resistance relative to HPPD SEQ ID NO:14 to sulcotrion according to the pyomelanin assay with 25 ppm sulcotrione.

Example 3

Preparation and Testing of Stable Transgenic Plant Lines Expressing a Heterologous HPPD Enzyme In the present example, mutant HPPD genes derived from *Avena* HPPD were the sequences set forth in SEQ ID NOS: 1-13 (optimized for tobacco) or, optionally, are codon optimized according to target crop (e.g., soybean) and prepared synthetically and obtained commercially from GeneArt (Regensburg, Germany). Each sequence is designed to have 5' Nde1 and 3'BamH1 sites to facilitate direct cloning. For example, the sequences set forth in SEQ ID NOS:11, 12, or 13 are cloned into a suitable binary vector for *Agrobacterium*-based plant transformation.

In a particular example genes encoding HPPD SEQ ID NO:14 and HPPD SEQ ID NO: 24 were cloned into identical expression constructs as described below and transformed into tobacco.

Figure 2A:
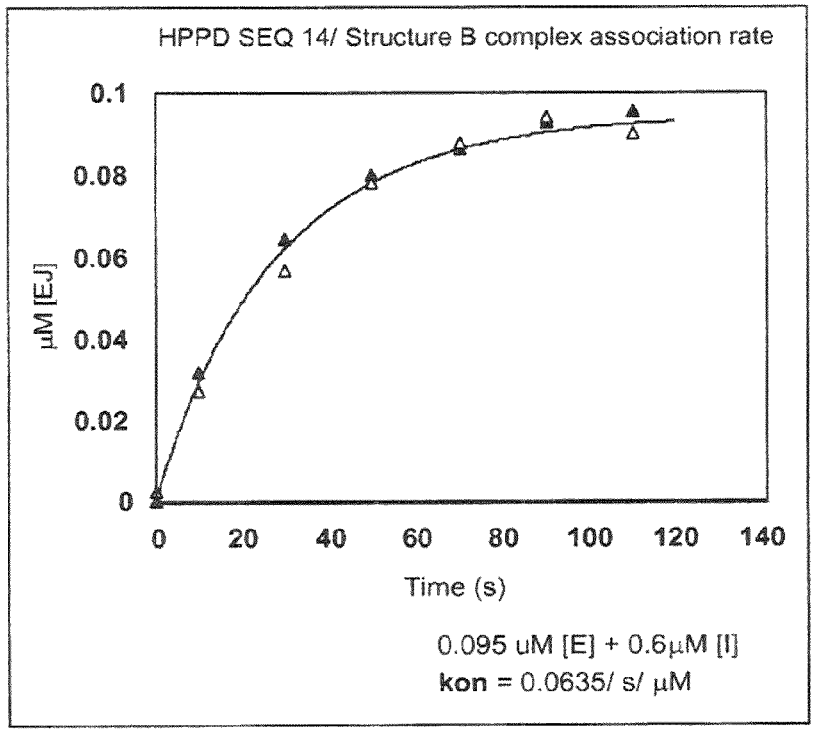
FIGS. 2A-2B show on rate (FIG. 2A) and off rate (FIG. 2B) determinations for a complex of structure B with the HPPD polypeptide corresponding to the amino acid sequence set forth in SEQ ID NO:14.
Figure 2B:
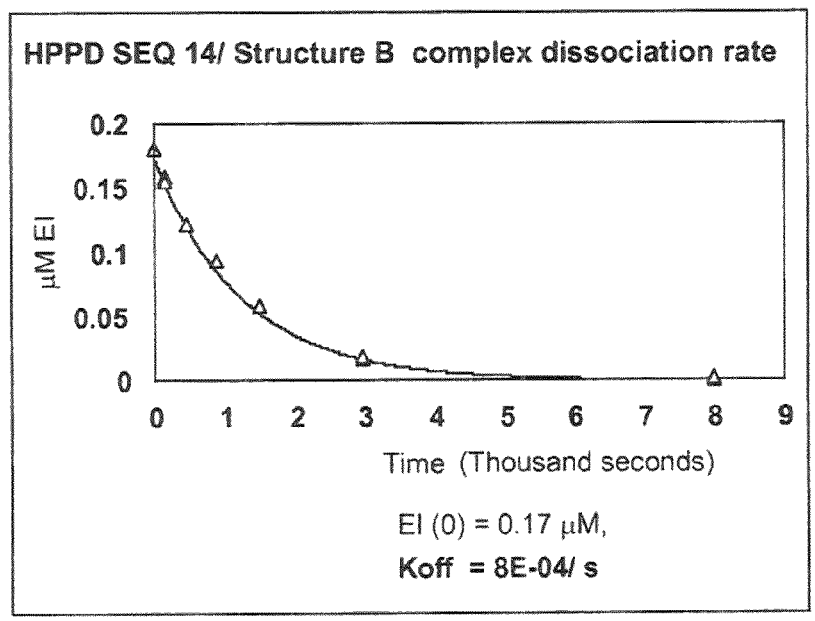
Figure 3:
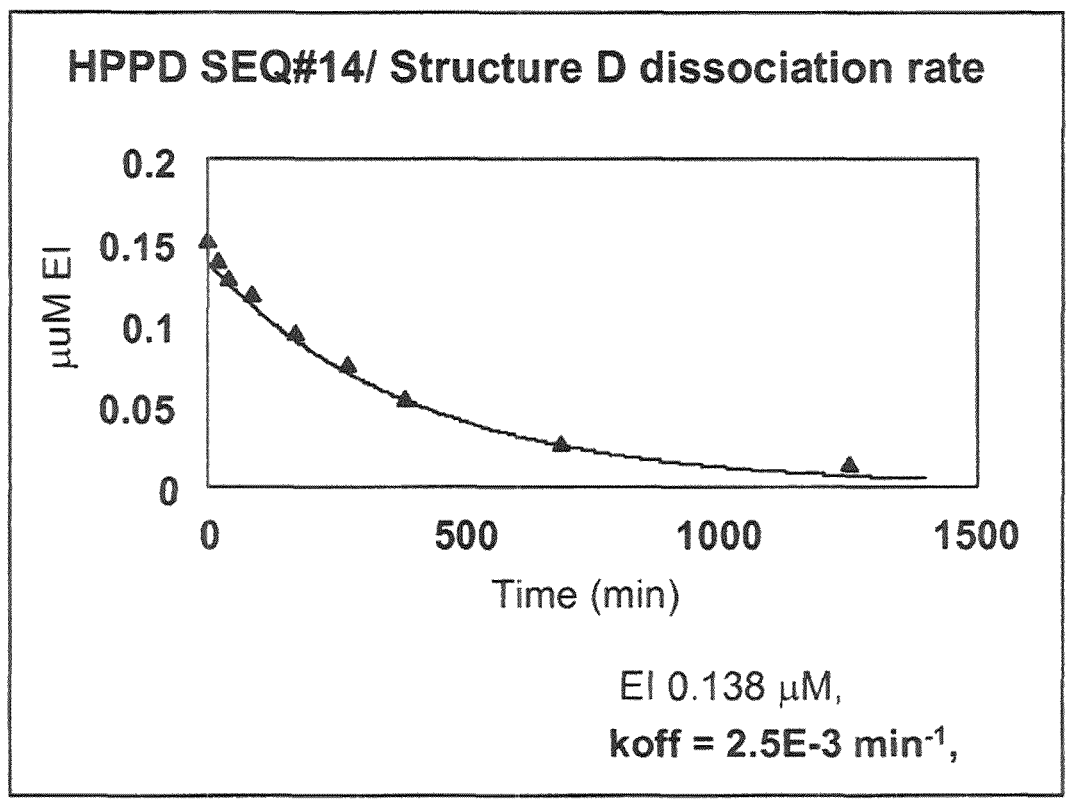
FIG. 3 shows an off rate determination for a complex of structure D with the HPPD polypeptide corresponding to the amino acid sequence set forth in SEQ ID NO:14.

As described in PCT Patent App. Pub. No. WO 02/46387, the HPPD encoding nucleotide sequence is edited by PCR (or initially synthesized) to include 5' Nco1 and 3' Kpn1 sites (and to remove any such internal sites). This product is then ligated into pMJB1. pMJB1 was a pUC19 derived plasmid which contains the plant operable double enhanced CaMV35S promoter; a TMV omega enhancer, and the NOS transcription terminator. A schematic representation of the resulting plasmid is shown in FIG. 2 of PCT Patent App. Pub. No. WO 98/20144. The expression cassette, comprising the double enhanced 35S promoter, TMV omega leader, 4-HPPD gene and nos terminator, is excised using Hind III/Eco R1 (partial Eco R1 digest) and cloned into similarly digested pBIN 19 and transformed into *E. coli* TOP 10 competent cells. DNA recovered from the *E. coli* is used to transform *Agrobacterium tumefaciens* LBA4404, and transformed bacteria are selected on media contain rifampicin and kanamycin. Tobacco tissue is subjected to *Agrobacterium*-mediated transformation using methods well described in the art or as described herein. For example, a master plate of *Agrobacterium tumefaciens* containing the HPPD expressing binary vector is used to inoculate 10 ml LB (L broth) containing 100 mg/1 Rifampicin plus 50 mg/1 Kanamycin using a single bacterial colony. This is incubated overnight at 28° C. shaking at 200 rpm. This entire overnight culture is used to inoculate a 50 ml volume of LB containing the same antibiotics. Again this is cultured overnight at 28° C. shaking at 200 rpm. The *Agrobacterium* cells are pelleted by centrifuging at 3000 rpm for 15 minutes and then resuspended in MS (Murashige and Skoog) medium containing 30 g/1 sucrose, pH 5.9 to an OD (600 nM)=0.6. This suspension is dispensed in 25 ml aliquots into petri dishes.

Clonally micro-propagated tobacco shoot cultures are used to excise young (not yet fully expanded) leaves. The mid rib and outer leaf margins are removed and discarded, and the remaining lamina cut into 1 cm squares. These are transferred to the *Agrobacterium* suspension for 20 minutes. Explants are then removed, dabbed on sterile filter paper to remove excess suspension, then transferred onto solid NBM medium (MS medium containing 30 g/1 sucrose, 1 mg/1 BAP (benzylaminopurine) and 0.1 mg/1 NAA (napthalene acetic acid) at pH 5.9 and solidified with 8 g/1 Plantagar), with the abaxial surface of each explant in contact with the medium. Approximately 7 explants are transferred per plate, which are then sealed and maintained in a lit incubator at 25° C. for a 16 hour photoperiod for 3 days.

Explants are then transferred onto NBM medium containing 100 mg/1 Kanamycin plus antibiotics to prevent further growth of *Agrobacterium* (200 mg/1 timentin with 250 mg/1 carbenicillin). Further subculture onto this same medium was then performed every 2 weeks.

As shoots start to regenerate from the callusing leaf explants, these are removed to Shoot elongation medium (MS medium, 30 g/1 sucrose, 8 g/1 Plantagar, 100 mg/1 Kanamycin, 200 mg/1 timentin, 250 mg/1 carbenicillin, pH 5.9). Stable transgenic plants readily root within 2 weeks. T0 provide multiple plants per event to ultimately allow more than one herbicide test per transgenic plant, all rooting shoots are micropropagated to generate 3 or more rooted clones.

Putative transgenic plants that are rooting and showing vigorous shoot growth on the medium incorporating Kanamycin are analysed by PCR using primers that amplified a 500 bp fragment within the HPPD transgene. Evaluation of this same primer set on untransformed tobacco showed conclusively that these primers would not amplify sequences from the native tobacco HPPD gene.

Transformed shoots are divided into 2 or 3 clones and regenerated from kanamycin resistant callus. Shoots are rooted on MS agar containing kanamycin. Surviving rooted explants are re-rooted to provide approximately 70-80 kanamycin resistant and PCR-positive events from each event.

Once rooted, plantlets are transferred from agar and potted into 50% peat, 50% John Innes Soil No. 3 with slow-release fertilizer in 3 inch round pots and left regularly watered to establish for 8-12d in the glass house. Glass house conditions are about 24-27° C. day; 18-21° C. night and approximately a 14 h photoperiod. Humidity is adjusted to ~65% and light levels used are up to 2000 µmol/m² at bench level.

Two transgenic populations each of about 80 tobacco plants and comprising, alternatively, an HPPD gene encoding HPPD SEQ ID NO:14 or HPPD SEQ ID NO:24 within otherwise identical expression cassettes were thus produced. These two populations were grown on until about the 2-4 leaf stage and then each divided into two subpopulations, one comprising those plantlets that had emerged rather larger and more advanced from tissue culture and the other population comprising the smaller plants. Thus the small sized populations of SEQ ID NO:14 and SEQ ID NO:24 appeared visually similar to comparable eachother as did the two populations of larger sized plants.

The two smaller populations were each then sprayed with 300 g/ha of mesotrione and the two larger populations with 500 g/ha. Callisto® was mixed in water with 0.2-0.25% X-77 surfactant and sprayed from a boom on a suitable track sprayer moving at 2 mph with the nozzle about 2 inches from the plant tops. Spray volume was 2001/ha.

Plants were assessed for damage and scored at 13 days after treatment (DAT). All four populations appeared highly resistant to the herbicide treatments but the SEQ ID NO:24 HPPD expressing populations more so than the control SEQ ID NO:14 populations. From the two larger-sized populations sprayed with 500 g/ha only 4 of 38 (10%) morphologically normal PCR positive plants (one emerged chimeric) expressing SEQ ID NO:24 exhibited symptoms of herbicide damage whereas 9 out of a total of 33 (27%) of SEQ ID NO:14 expressing plants exhibited damage. There was little damage to see on the two smaller-sized populations sprayed with 300 g/ha mesotrione; here 2 of 28 SEQ ID NO:24 expressing plants exhibited visible herbicide damage as compared with 4 of 26 SEQ ID NO:14 expressing plants.

Plants of events showing the least damage are grown to flowering, then bagged and allowed to self. The seed from selected events are collected and sown again in pots, and tested again for herbicide resistance in a spray test for resistance to HPPD herbicide (for example mesotrione). Single copy events amongst the T1 plant lines are identified by their 3:1 segregation ratio (with respect to kanamycin and/or herbicide) and by quantitative RT-PCR. Seed from the thus selected T1 tobacco (var. *Samsun*) lines are sown in 3 inch diameter pots containing 50% peat and 50% John Innes Soil No. 3.

Example 4

Construction of Soybean Transformation Vectors

Binary vectors for dicot (soybean) transformation were constructed with a promoter, such as a synthetic promoter containing a CaMV 35S and an FMV transcriptional enhancer and a synthetic TATA box driving the expression of an HPPD coding sequence, such as SEQ ID NO:24, followed by Nos gene 3' terminator. The HPPD gene was codon-optimized for soybean expression based upon the predicted amino acid sequence of the HPPD gene coding region. In the case that HPPD itself was not used as the selectable marker, *Agrobacterium* binary transformation vectors containing an HPPD expression cassette were constructed by adding a transformation selectable marker gene. For example, binary transformation vector 17146 (SEQ ID NO:33) contains an expression cassette for HPPD variant (SEQ ID NO:24) linked with two PAT gene cassettes (one with the 35S promoter and one with the CMP promoter, and both PAT genes are followed by the nos terminator) for glufosinate based selection during the transformation process. Another binary transformation vector (17147) (SEQ ID NO:34) contains the HPPD variant (SEQ ID NO:24) expression cassette and also an EPSPS selectable marker cassette. Vector 17147 was transformed into soybean and transgenic plants were obtained using glyphosate selection after *Agrobacterium*-mediated transformation of immature seed targets. Similarly, binary vector 15764, (SEQ ID NO:35) was constructed to comprise expression cassettes to express HPPD (SEQ ID NO:14) along with a bar selectable marker gene and binary vector 17149 (SEQ ID NO:36) was constructed to comprise an expression cassette expressing HPPD variant (SEQ ID NO:26) along with two PAT gene cassettes. In all cases the DNA sequences encoding the HPPD genes were codon-optimized for expression in soybean.

The Binary Vectors described above were constructed using a combination of methods well known to those skilled in the art such as overlap PCR, DNA synthesis, restriction fragment sub-cloning and ligation. Their unique structures are made explicit in FIGS. 6 (vector 17146), 7 (vector 17147), 8 (vector 15764), and 9 (vector 17149), and in the sequence listings (SEQ ID NOS:33-36). Additional information regarding the vectors shown in FIGS. 6-9 are provided below.

Figure 6:
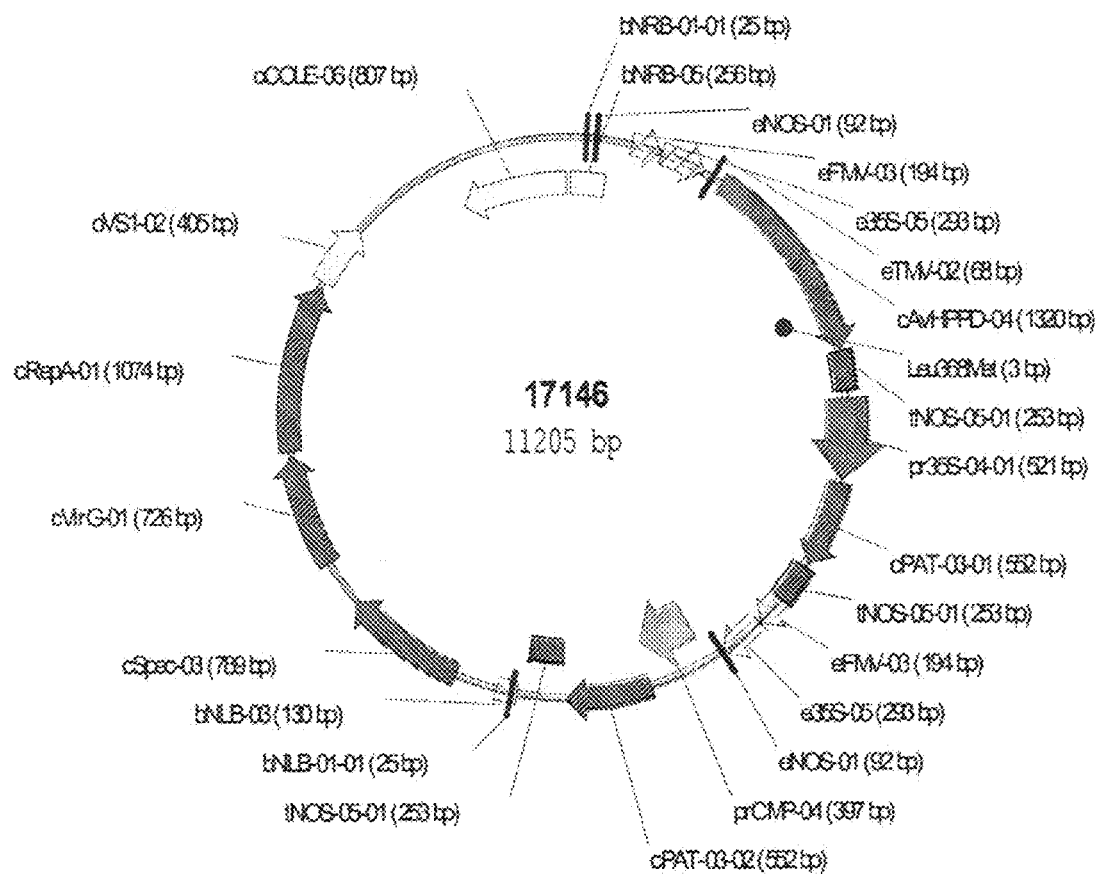
FIG. 6 shows a representation of binary vector 17146 for soybean transformation, conferring HPPD resistance with a soybean codon optimized Oat HPPD gene encoding SEQ ID NO:24. This binary vector also contains double PAT selectable markers for glufosinate selection.
Figure 7:
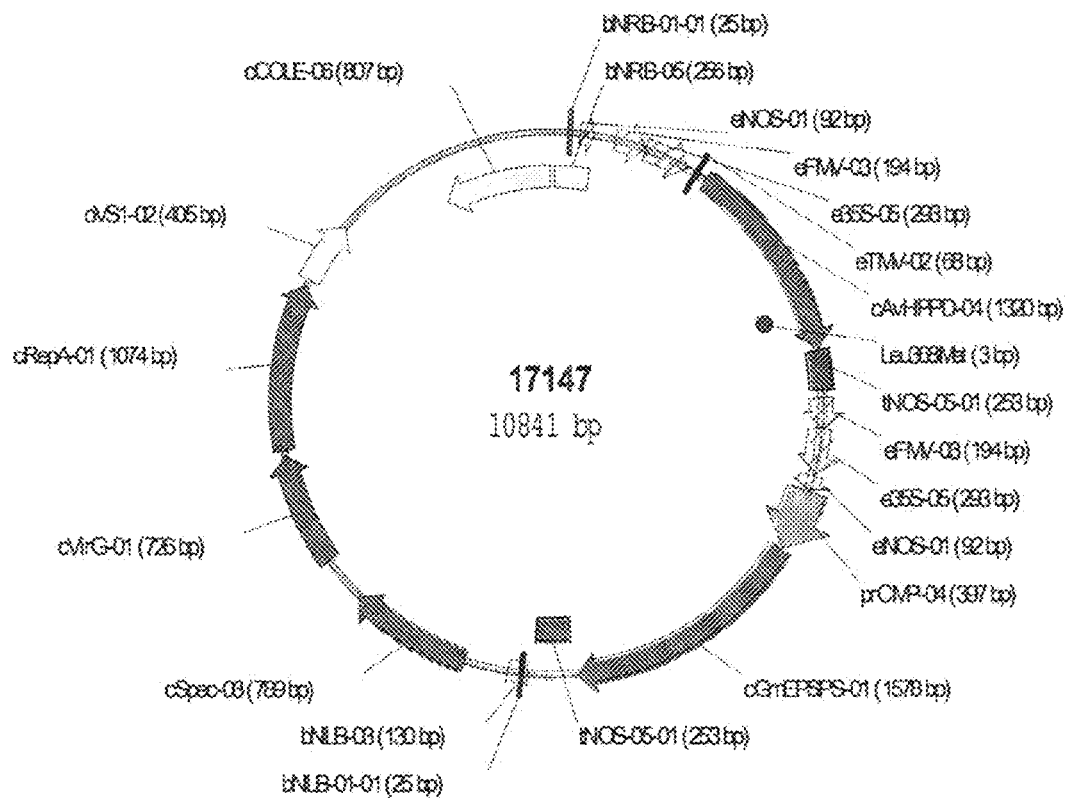
FIG. 7 shows a representation of binary vector 17147 for soybean transformation conferring HPPD resistance with a soybean codon optimized Oat HPPD gene encoding SEQ ID NO:24 and also conferring tolerance to glyphosate (selectable marker).
Figure 8:
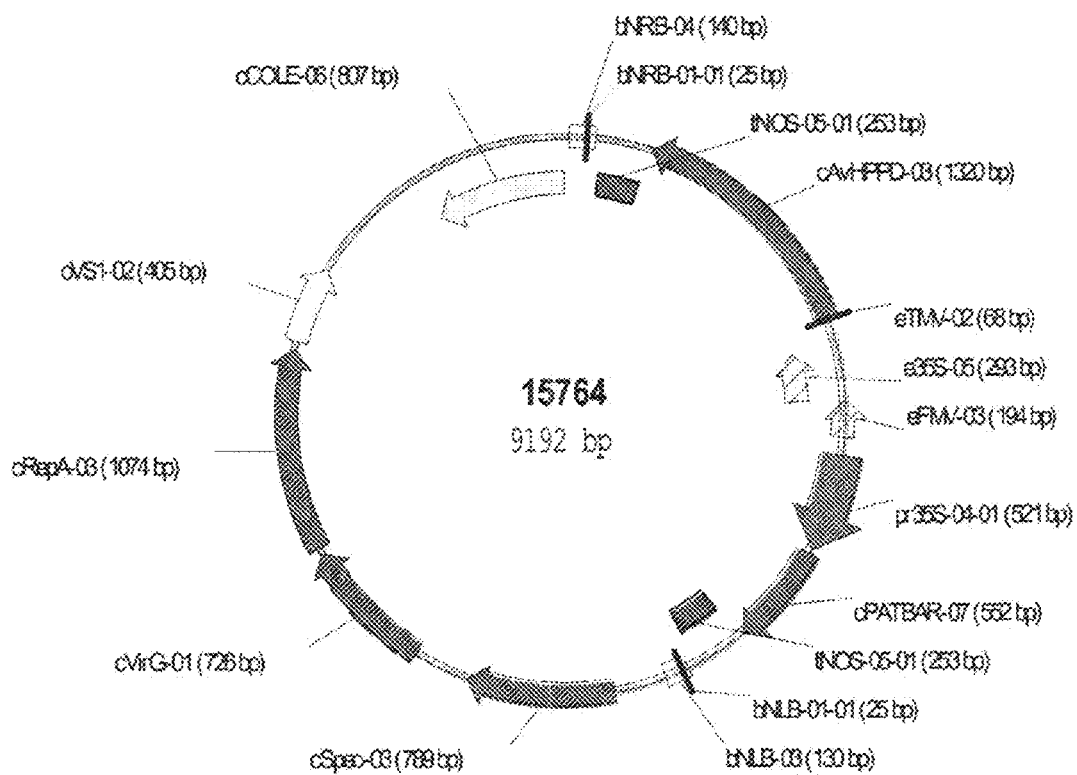
FIG. 8 shows a representation of binary vector 15764 containing a soybean codon optimized Oat HPPD gene (encoding SEQ ID NO:14) driven by the TMV omega enhancer and a TATA box.
Figure 9:
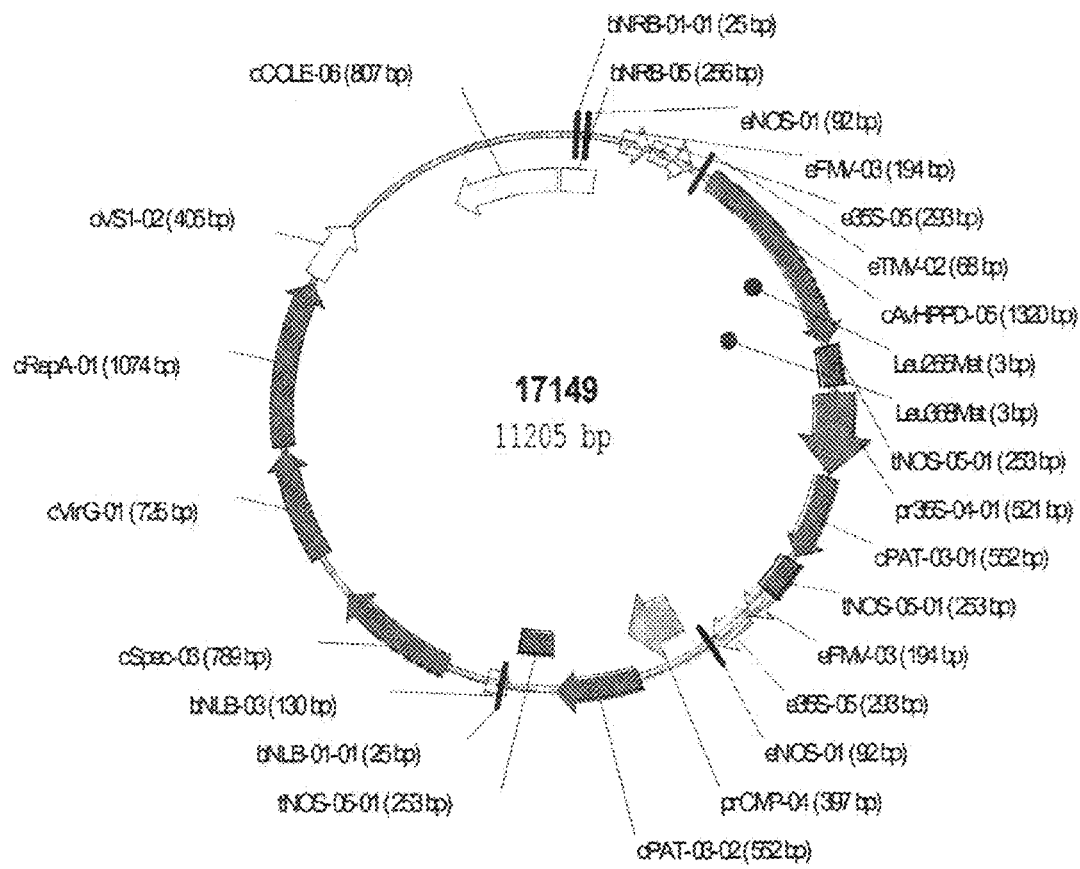
FIG. 9 shows a representation of binary vector 17149 for soybean transformation conferring tolerance to HPPD herbicides and to glufosinate, containing an expression cassette expressing an HPPD variant (SEQ ID NO:26) along with two PAT gene cassettes.
Figure 10A:
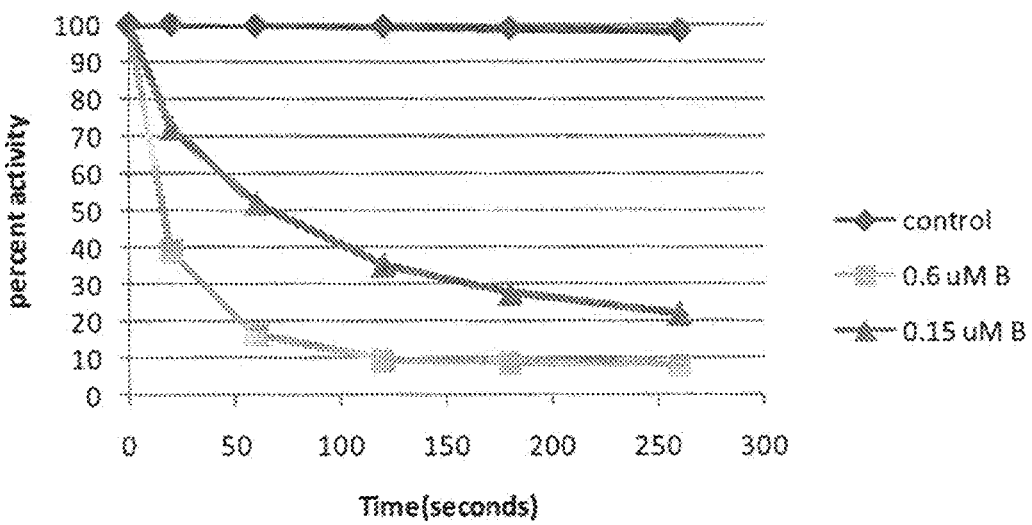
FIGS. 10A-10D depict the time-dependence of inhibition of a mutant of HPPD (G408A) by herbicide compounds B (FIGS. 10A-10B) and C (FIGS. 10C-10D).
Figure 10B:
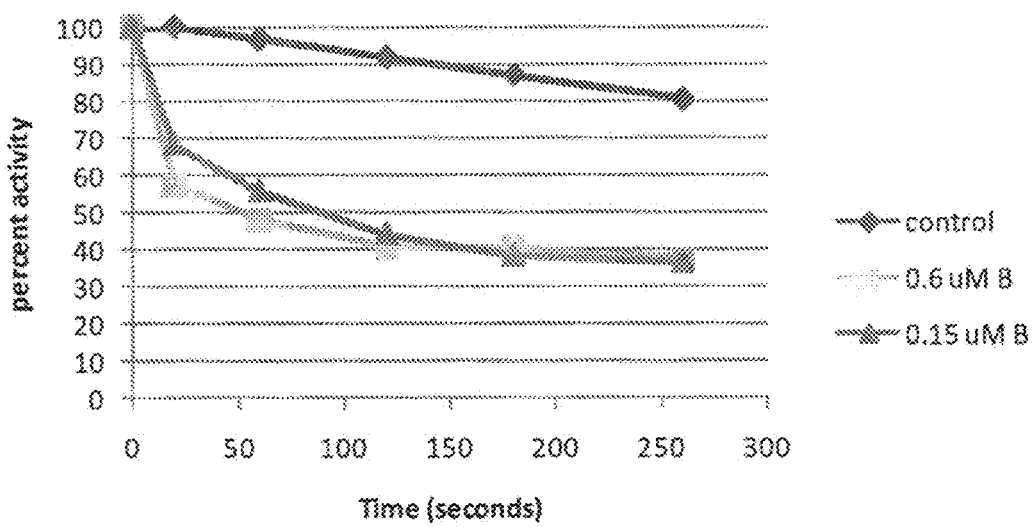
Figure 10C:
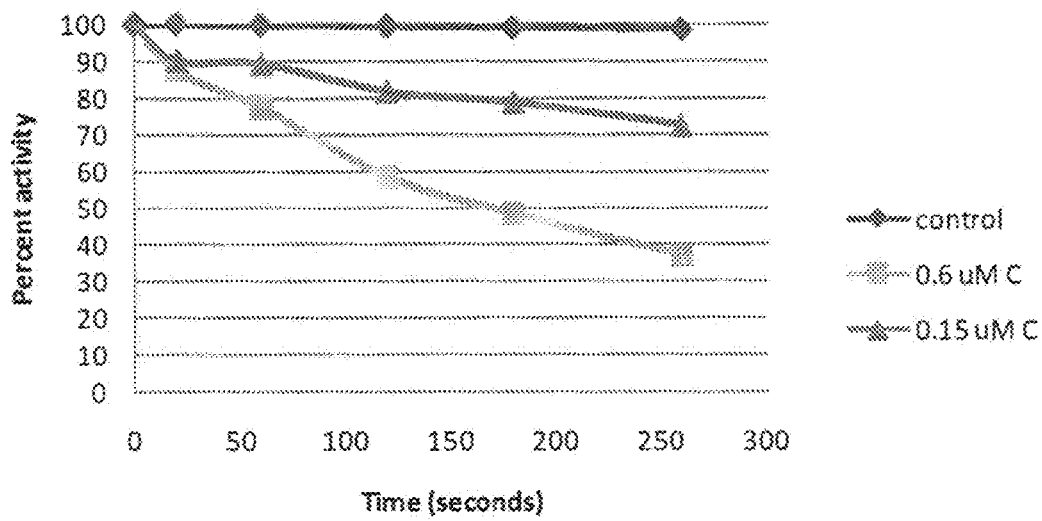
Figure 10D:
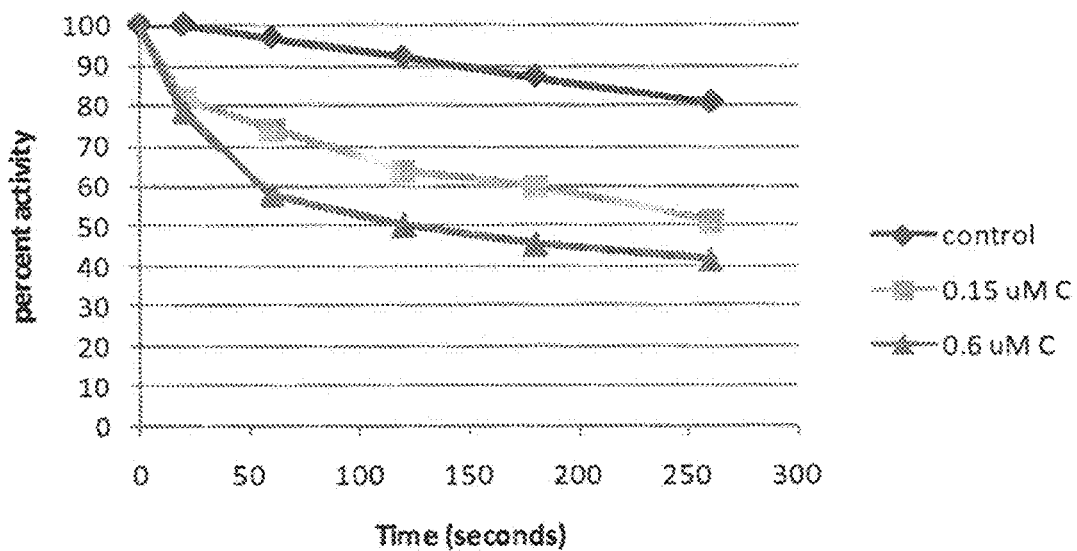

The abbreviations used in FIG. 6 (vector 17146) are defined as follows:
  cAvH PP D-04
  Start: 1024 End: 2343
  Soybean codon optimized Oat HPPD gene encoding SEQ ID NO 24
  cPAT-03-01
  Start: 3209 End: 3760
  PAT Hoescht A02774 synthetic S. viridochromogenes, plant codons; identical to Q57146
  phosphinothricin acetyl transferase protein
  cPAT-03-02
  Start: 5062 End: 5613
  PAT Q57146 S. viridochromogenes phosphinothricin acetyl transferase protein, cPAT-03-01 DNA, with mutated BamH1, Bgl2 sites
  cSpec-03
  Start: 6346 End: 7134
  Also called aadA; gene encoding the enzyme aminoglycoside 3′ adenyltransferase that confers resistance to spectinomycin and streptomycin for maintenance of the vector in *E. coli* and *Agrobacterium*. aka cSPEC-03
  cVirG-01
  Start: 7434 End: 8159
  virG (putative) from pAD1289 with TTG start codon. virGN54D came from pAD1289
  described in Hansen et al. 1994, *PNAS* 91:7603-7607
  cRepA-01
  Start: 8189 End: 9262
  RepA, pVS1 replication protein
  eNOS-01
  Start: 168 End: 259
  Putative NOS enhancer sequence from 15235 as found in the right border of certain binary vectors.
  eFMV-03
  Start: 396 End: 589
  enhancer region from Figwort mosaic virus (FMV)
  e35S-05
  Start: 596 End: 888
  C to T & C to A by changes in Cauliflower mosaic virus 35S enhancer region
  eTMV-02
  Start: 953 End: 1020
  TMV Omega 5′UTR leader seq thought to enhance expression. EMBL: TOTMV6
  eFMV-03
  Start: 4054 End: 4247
  enhancer region from Figwort mosaic virus (FMV)
  e35S-05
  Start: 4254 End: 4546
  C to T & C to A by changes in Cauliflower mosaic virus 35S enhancer region
  eNOS-01
  Start: 4557 End: 4648
  Putative NOS enhancer sequence from 15235 as found in the right border of certain binary vectors.
  bNRB-05
  Start: 4 End: 259 (Complementary)
  Right border/NOS T-DNA region; may influence promoters. EMBL no: J01826, V00087, AF485783.
  bNRB-01-01
  Start: 101 End: 125 (Complementary)
  Right Border Repeat of T-DNA of *Agrobacterium tumefaciens* nopaline ti-plasmid
  bNLB-03
  Start: 5937 End: 6066 (Complementary)
  Left border region of T-DNA of *Agrobacterium tumefaciens* nopaline ti-plasmid
  bNRB-01-01
  Start: 5972 End: 5996 (Complementary)
  25 bp Left border repeat region of T-DNA of *Agrobacterium tumefaciens* nopaline ti-plasmid
  prCMP-04
  Start: 4655 End: 5051
  Cestrum Yellow leaf curl virus promoter & leader (start aagggagc?). genbank AF364175.
  US20040086447. prCMP-01 with 1 base pair truncation on 5′ end and 2 base pair truncation on 3′ end
  pr35S-04-01
  Start: 2664 End: 3184
  35S promoter from Cauliflower Mosaic Virus. EMBL: CAMVG2
  oVS1-02
  Start: 9305 End: 9709
  origin of replication and partitioning region from plasmid pVS1 of *Pseudomonas* (Itoh et al. 1984, *Plasmid* 11: 206-220); similar to GenBank Accession Number U10487; serves as origin of replication in *Agrobacterium tumefaciens* host
  oCOLE-06
  Start: 10387 End: 11193 (Complementary)
  The ColE1 origin of replication functional in *E. coli* derived from pUC19
  tNOS-05-01
  Start: 2360 End: 2612
  synthetic Nopaline synthetase terminator
  tNOS-05-01
  Start: 3794 End: 4046
  synthetic Nopaline synthetase terminator
  tNOS-05-01
  Start: 5642 End: 5894
  synthetic Nopaline synthetase terminator The abbreviations used in FIG. 7 (vector 17147) are defined as follows:
  cAvH PP D-04
  Start: 1024 End: 2343

Soybean codon optimized Oat HPPD gene encoding SEQ ID NO 24
cGm EPSPS-01
Start: 3672 End: 5249
Soybean codon-optimized version of double mutant soybean EPSPS cDNA
cSpec-03
Start: 5982 End: 6770
Also called aadA; gene encoding the enzyme aminoglycoside 3' adenyltransferase that confers resistance to spectinomycin and streptomycin for maintenance of the vector in E. coli and Agrobacterium. aka cSPEC-03
cVirG-01
Start: 7070 End: 7795
virG (putative) from pAD1289 with TTG start codon. virGN54D came from pAD1289 described in Hansen et al. 1994, *PNAS* 91:7603-7607
cRepA-01
Start: 7825 End: 8898
RepA, pVS1 replication protein
Original Location Description:
eNOS-01
Start: 168 End: 259
Putative NOS enhancer sequence from 15235 as found in the right border of certain binary vectors.
eFMV-03
Start: 396 End: 589
enhancer region from Figwort mosaic virus (FMV)
e35S-05
Start: 596 End: 888
C to T & C to A by changes in Cauliflower mosaic virus 35S enhancer region
eTMV-02
Start: 953 End: 1020
TMV Omega 5'UTR leader seq thought to enhance expression. EMBL: TOTMV6
eFMV-03
Start: 2664 End: 2857
enhancer region from Figwort mosaic virus (FMV)
e35S-05
Start: 2864 End: 3156
C to T & C to A by changes in Cauliflower mosaic virus 35S enhancer region
eNOS-01
Start: 3167 End: 3258
Putative NOS enhancer sequence from 15235 as found in the right border of certain binary vectors.
bNRB-05
Start: 4 End: 259 (Complementary)
Right border/NOS T-DNA region; may influence promoters. EMBL no: J01826, V00087, AF485783.
bNRB-01-01
Start: 101 End: 125 (Complementary)
Right Border Repeat of T-DNA of *Agrobacterium tumefaciens* nopaline ti-plasmid
bNLB-03
Start: 5573 End: 5702 (Complementary)
Left border region of T-DNA of *Agrobacterium tumefaciens* nopaline ti-plasmid
bNLB-01-01
Start: 5608 End: 5632 (Complementary)
25 bp Left border repeat region of T-DNA of *Agrobacterium tumefaciens* nopaline ti-plasmid
prCMP-04
Start: 3265 End: 3661
Cestrum Yellow leaf curl virus promoter & leader (start aagggagc?). genbank AF364175.
US20040086447. prCMP-01 with 1 base pair truncation on 5' end and 2 base pair truncation on 3' end
Original Location Description:
oVS1-02
Start: 8941 End: 9345
origin of replication and partitioning region from plasmid pVS1 of *Pseudomonas* (Itoh et al. 1984, *Plasmid* 11: 206-220); similar to GenBank Accession Number U10487; serves as origin of replication in *Agrobacterium tumefaciens* host
oCOLE-06
Start: 10023 End: 10829 (Complementary)
The ColE1 origin of replication functional in *E. coli* derived from pUC19
tNOS-05-01
Start: 2360 End: 2612
synthetic Nopaline synthetase terminator
tNOS-05-01
Start: 5278 End: 5530
synthetic Nopaline synthetase terminator
The abbreviations used in FIG. 8 (vector 15764) are defined as follows:
cAvH PP D-03
Start: 450 End: 1769 (Complementary)
Soybean codon optimized Oat HPPD gene encoding SEQ ID NO 14
cPATBAR-07
Start: 3034 End: 3585
BAR X17220 *S. hygroscopicus* gene (mutated Bg12 site), caa35093 phosphinothricin acetyl transferase protein.
cSpec-03
Start: 4334 End: 5122
streptomycin adenylyltransferase; from Tn7 (aadA)
cVirG-01
Start: 5422 End: 6147
Virulence G gene from *Agrobacterium tumefaciens* (virGN54D, containing TTG start codon) virGN54D came from pAD1289 described in Hansen et al. 1994, PNAS 91:7603-7607
cRepA-03
Start: 6177 End: 7250
RepA, pVS1 replication protein with A to G at nt735
eTMV-02
Start: 1773 End: 1840 (Complementary)
Tobacco mosaic virus (TMV_Omega 5'UTR leader seq thought to enhance expression.
EMBL: TOTMV6
e35S-05
Start: 1905 End: 2197 (Complementary)
Cauliflower mosaic virus 35S enhancer region with C to T & C to A bp changes.
eFMV-03
Start: 2204 End: 2397 (Complementary)
Figwort mosaic virus enhancer.
bNRB-04
Start: 5 End: 144 (Complementary)
Right border region of T-DNA of *Agrobacterium tumefaciens* nopaline ti-plasmid.
Differs from bNRB-03 by 20 bp at 5' end.
bNRB-01-01
Start: 102 End: 126 (Complementary)
Right Border Repeat of T-DNA of *Agrobacterium tumefaciens* nopaline ti-plasmid.
bNLB-03
Start: 3925 End: 4054 (Complementary)
Left border region of T-DNA from *Agrobacterium tumefaciens* nopaline ti-plasmid.

(Zambryski et al. 1980, Science, 209:1385-1391) EMBL no: J01825.
bNLB-01-01
Start: 3960 End: 3984 (Complementary)
25 bp Left border region of T-DNA of *Agrobacterium tumefaciens* nopaline ti-plasmid.
pr35S-04-01
Start: 2494 End: 3014
35S promoter; map originally defined promoter as 641 bp long; no exact match found in literature (LF July 2004)
oVS1-02
Start: 7293 End: 7697
origin of replication and partitioning region from plasmid pVS1 of *Pseudomonas* (Itoh et al. 1984, *Plasmid* 11: 206-220); similar to GenBank Accession Number U10487; serves as origin of replication in *Agrobacterium tumefaciens* host
oCOLE-06
Start: 8375 End: 9181 (Complementary)
ColE1 origin of replication functional in *E. coli*
tNOS-05-01
Start: 181 End: 433 (Complementary)
NOS terminator: 3'UTR of the nopaline synthase gene
tNOS-05-01
Start: 3619 End: 3871
NOS terminator: 3'UTR of the nopaline synthase gene
The abbreviations used in FIG. 9 (vector 17149) are defined as follows:
cAvH PP D-05
Start: 1024 End: 2343
Soybean codon optimized sequence encoding HPPD SEQ ID NO 26
cPAT-03-01
Start: 3209 End: 3760
PAT Hoescht A02774 synthetic S. viridochromogenes, plant codons; identical to Q57146 phosphinothricin acetyl transferase protein
cPAT-03-02
Start: 5062 End: 5613
PAT Q57146 S. viridochromogenes phosphinothricin acetyl transferase protein, cPAT-03-01 DNA, witht mutated BamH1, Bgl2 sites
cSpec-03
Start: 6346 End: 7134
Also called aadA; gene encoding the enzyme aminoglycoside 3' adenyltransferase that confers resistance to spectinomycin and streptomycin for maintenance of the vector in *E. coli* and *Agrobacterium*. aka cSPEC-03
cVirG-01
Start: 7434 End: 8159
virG (putative) from pAD1289 with TTG start codon. virGN54D came from pAD1289 described in Hansen et al. 1994, *PNAS* 91:7603-7607
cRepA-01
Start: 8189 End: 9262
RepA, pVS1 replication protein
Original Location Description
eNOS-01
Start: 168 End: 259
Putative NOS enhancer sequence from 15235 as found in the right border of certain binary vectors.
eFMV-03
Start: 396 End: 589
enhancer region from Figwort mosaic virus (FMV)
e35S-05
Start: 596 End: 888
C to T & C to A by changes in Cauliflower mosaic virus 35S enhancer region
eTMV-02
Start: 953 End: 1020
TMV Omega 5'UTR leader seq thought to enhance expression. EMBL: TOTMV6
eFMV-03
Start: 4054 End: 4247
enhancer region from Figwort mosaic virus (FMV)
e35S-05
Start: 4254 End: 4546
eNOS-01
Start: 4557 End: 4648
Putative NOS enhancer sequence from 15235 as found in the right border of certain binary vectors
bNRB-05
Start: 4 End: 259 (Complementary)
Right border/NOS T-DNA region; may influence promoters. EMBL no: J01826, V00087, AF485783.
bNRB-01-01
Start: 101 End: 125 (Complementary)
Right Border Repeat of T-DNA of *Agrobacterium tumefaciens* nopaline ti-plasmid
bNLB-03
Start: 5937 End: 6066 (Complementary)
Left border region of T-DNA of *Agrobacterium tumefaciens* nopaline ti-plasmid
bNLB-01-01
Start: 5972 End: 5996 (Complementary)
25 bp Left border repeat region of T-DNA of *Agrobacterium tumefaciens* nopaline ti-plasmid
prCMP-04
Start: 4655 End: 5051
Cestrum Yellow leaf curl virus promoter & leader (start aagggagc?). genbank AF364175.
US20040086447. prCMP-01 with 1 base pair truncation on 5' end and 2 base pair truncation on 3' end
pr35S-04-01
Start: 2664 End: 3184
35s promoter from CaMV. EMBL: CAMVG2 (100% match against this EMBL record)
oVS1-02
Start: 9305 End: 9709
origin of replication and partitioning region from plasmid pVS1 of *Pseudomonas* (Itoh et al. 1984, *Plasmid* 11: 206-220); similar to GenBank Accession Number U10487; serves as origin of replication in *Agrobacterium tumefaciens* host
oCOLE-06
Start: 10387 End: 11193 (Complementary)
The ColE1 origin of replication functional in *E. coli* derived from pUC19
tNOS-05-01
Start: 2360 End: 2612
synthetic Nopaline synthetase terminator
tNOS-05-01
Start: 3794 End: 4046
synthetic Nopaline synthetase terminator
tNOS-05-01
Start: 5642 End: 5894
synthetic Nopaline synthetase terminator Example 5

Transformation of Soybean and Selection of Herbicide-Resistant Plants

Soybean plant material can be suitably transformed and fertile plants regenerated by many methods which are well known to one of skill in the art. For example, fertile morphologically normal transgenic soybean plants may be obtained by: 1) production of somatic embryogenic tissue from, e.g., immature cotyledon, hypocotyl or other suitable tissue; 2) transformation by particle bombardment or infection with Agrobacterium; and 3) regeneration of plants. In one example, as described in U.S. Pat. No. 5,024,944, cotyledon tissue is excised from immature embryos of soybean, preferably with the embryonic axis removed, and cultured on hormone-containing medium so as to form somatic embryogenic plant material. This material is transformed using, for example, direct DNA methods, DNA coated microprojectile bombardment or infection with Agrobacterium, cultured on a suitable selection medium and regenerated, optionally also in the continued presence of selecting agent, into fertile transgenic soybean plants. Selection agents may be antibiotics such as kanamycin, hygromycin, or herbicides such as phosphonothricin or glyphosate or, alternatively, selection may be based upon expression of a visualisable marker gene such as GUS. Alternatively, target tissues for transformation comprise meristematic rather than somaclonal embryogenic tissue or, optionally, is flower or flower-forming tissue. Other examples of soybean transformations can be found, e.g. by physical DNA delivery method, such as particle bombardment (Finer and McMullen (1991) *In Vitro Cell Dev. Biol.* 27P:175-182; McCabe et al. (1988) *Bio/technology* 6:923-926), whisker (Khalafalla et al. (2006) *African J. of Biotechnology* 5:1594-1599), aerosol bean injection (U.S. Pat. No. 7,001,754), or by Agrobacterium-mediated delivery methods (Hinchee et al. (1988) *Bio/Technology* 6:915-922; U.S. Pat. No. 7,002,058; U.S. Patent App. Pub. No. 20040034889; U.S. Patent App. Pub. No. 20080229447; Paz et al. (2006) *Plant Cell Report* 25:206-213). The HPPD gene can also be delivered into organelle such as plastid to confer increased herbicide resistance (U.S. Patent App. Pub. No. 20070039075).

Soybean transgenic plants can be generated with the above described binary vectors (Example 4) containing HPPD gene variants with different transformation methods. Optionally, the HPPD gene can provide the means of selection and identification of transgenic tissue. For example, a vector was used to transform immature seed targets as described (U.S. Patent App. Pub. No. 20080229447) to generate transgenic HPPD soybean plants directly using HPPD inhibitor, such as mesotrione, as selection agent. Optionally, HPPD genes can be present in the polynucleotide alongside other sequences which provide additional means of selection/identification of transformed tissue including, for example, the known genes which provide resistance to kanamycin, hygromycin, phosphinothricin, butafenacil, or glyphosate. For example, different binary vectors containing PAT or EPSPS selectable marker genes as described in Example 4 were transformed into immature soybean seed target to generate HPPD herbicide tolerant plants using Agrobacterium-mediated transformation and glufosinate or glyphosate selection as described (U.S. Patent App. Pub. No. 20080229447).

Alternatively selectable marker sequences may be present on separate polynucleotides and a process of, for example, co-transformation and co-selection is used. Alternatively, rather than a selectable marker gene, a scorable marker gene such as GUS may be used to identify transformed tissue.

An Agrobacterium-based method for soybean transformation can be used to generate transgenic plants using glufosinate, glyphosate or HPPD inhibitor mesotrione as selection agent using immature soybean seeds as described (U.S. Patent App. Pub. No. 20080229447).

Example 6

Soybean Transgenic Plant Growth, Analysis and Herbicide Tolerance Evaluation

T0 plants were taken from tissue culture to the greenhouse where they were transplanted into water-saturated soil (REDI-EARTH® Plug and Seedling Mix, Sun Gro Horticulture, Bellevue, Wash., or Fafard Germinating Mix) mixed with 1% granular MARATHON® (Olympic Horticultural Products, Co., Mainland, Pa.) at 5-10 g/gal soil in 2" square pots. The plants were covered with humidity domes and placed in a Conviron chamber (Pembina, N. Dak.) with the following environmental conditions: 24° C. day; 20° C. night; 16-23 hr light-1-8 hrs dark photoperiod; 80% relative humidity.

After plants became established in the soil and new growth appeared (~1-2 weeks), plants were sampled and tested for the presence of desired transgene by TAQMAN® analysis using appropriate probes for the HPPD genes, or promoters (for example prCMP). Positive plants were transplanted into 4" square pots containing Fafard #3 soil. Sierra 17-6-12 slow release fertilizer was incorporated into the soil at the recommended rate. The plants were then relocated into a standard greenhouse to acclimatize (~1 week). The environmental conditions were: 27° C. day; 21° C. night; 14 hr photoperiod (with supplemental light); ambient humidity. After acclimatizing (~1 week), the plants were sampled and tested in detail for the presence and copy number of inserted transgenes. Transgenic soybean plants were grown to maturity for T1 seed production. T1 plants were grown up, and after TAQMAN® analysis, homozygous plants were grown for seed production. Transgenic seeds and progeny plants were used to further evaluate their herbicide tolerance performance and molecular characteristics.

Homozygous soybean plants from 2 events made with vector 15764 (FIG. 8) and multiple events made with vector 17147 (FIG. 7) expressing SEQ ID NO:14 and SEQ ID NO:24, respectively, from identical HPPD expression cassettes were grown and tested for tolerance to a range of HPPD herbicide. Table 8 summarises the results of these tests from plants sprayed at the V2 growth stage. Each data point represents the average damage score from n=7 replicates.

TABLE 8

Results of Herbicide Spray Tests Against Vector 15764 and 17147 Soybean Events
Chemical Applied

| EVENT/ | B | | C | | IFT | | E | | | |
|---|---|---|---|---|---|---|---|---|---|---|
| HPPD | 420 g/ha | | 840 g/ha | | 400 g/ha | | 420 g/ha | | 368 g/ha | |
| SEQ | % dam. | S.D. | % dam. | S.D. | % dam. | S.D. | % dam. | S.D. | % dam. | S.D. |
| 1/SEQ #14 | 11.4 | 4.8 | 9.3 | 3.6 | 42.1 | 8.1 | 26.4 | 6.9 | 36.4 | 4.8 |
| 2/SEQ #14 | 20.7 | 3.4 | 22.1 | 3.9 | 52.9 | 9.9 | 42.5 | 4.2 | 52.1 | 7 |
| S3/SEQ #24 | 15.3 | 2.4 | 15.3 | 3.7 | 62.1 | 6.4 | 30 | 4.1 | 51.4 | 6.3 |
| T0/SEQ #24 | 8.3 | 2.1 | 5.3 | 2.1 | 45 | 4.1 | 19.3 | 5.3 | 39.3 | 11.7 |

TABLE 8-continued

Results of Herbicide Spray Tests Against
Vector 15764 and 17147 Soybean Events
Chemical Applied

| EVENT/ | B | | | | C | | IFT | | E | |
|---|---|---|---|---|---|---|---|---|---|---|
| HPPD | 420 g/ha | | 840 g/ha | | 400 g/ha | | 420 g/ha | | 368 g/ha | |
| SEQ | % dam. | S.D. | % dam. | S.D. | % dam. | S.D. | % dam. | S.D. | % dam. | S.D. |
| S7/SEQ #24 | 10.6 | 2.4 | 6.9 | 2.4 | 45 | 4.1 | 20.7 | 3.4 | 41.4 | 3.8 |
| S8/SEQ #24 | 18.6 | 4.2 | 19.3 | 3.4 | 68.6 | 6.9 | 31.3 | 4.8 | 80 | 21.4 |
| SF/SEQ #24 | 15.7 | 3.9 | 25 | 5.8 | 98.6 | 3.8 | 40 | 5.8 | 97.1 | 7.6 |
| Jack w/t | 82.9 | 8.6 | 83.6 | 4.8 | 82.1 | 3.9 | 96.1 | 3.5 | 84.3 | 8.4 |

Event 1 was most tolerant to mesotrione, and event 2 was the second most tolerant 15764 event selected from a population of about ninety. These events were used to compare the performance of five 17147 events. Four of these, SF, S8, S7 and S3 had not been preselected for tolerance level (other than to confirm resistance, non-chimerical nature and the presence of the gene) while the remaining event, T0, had been preselected as the most resistant out of five 17147 events in a preliminary field test.

Plants were in 4×4×4 inch plastic pots and grown under a 15/9 hour light regime (daylight supplemented by artificial light in greenhouses) at a minimum night-time temperature of 18° C. and maximum daytime temperature of 27° C. Soil was regular VBRC mix (1:1 mixture of Vero field soil and Fafard Mix II) where Vero field soil is 98% sand and 2% clay. Treatments with compound B, =CALLISTO® 4 SC (480 g ai/L), with compound C (200 g ai/L) EC, with IFT=Balance Pro 4 SC (480 g ai/L), and with compound E=Laudis 3.5 SC (420 g ai/L) included 0.25% v/v INDUCE (a non-ionic surfactant) and ammonium sulfate (N-PAK liquid AMS) at a rate equivalent to 8.5 lbs/gallon. Spray volume was 150 L/ha and the damage scores reflect assessments at 14 DAT.

It is striking that, from such a small pool of 17147 events all five tested provided tolerance to mesotrione and to isoxaflutole equivalent to one of the best 15764 events, event 2, and indeed that two of them, T0 and S7 exceed the performance of the most tolerant 15764 event, event 1, that was selected from many.

The in vitro data, and in particular the off rate data, show that SEQ ID NO:24 is 2 and 2.3 fold superior to SEQ ID NO:14 in respect of B and IFT but neutral in respect of C and E. In accord with this is the fact that the SEQ ID NO:24 HPPD expressing plants displayed a similarly altered pattern of herbicide tolerance. Thus, for example, events SF and S8 exhibits similar or better tolerance to both IFT and B than does 6W but, unlike 6W, essentially no tolerance to either compound E or C. Similarly, the only 17147 events, T0 and S7, to exhibit tolerance to E and C that is close to that of event 4R also exhibit superior tolerance than 4R to B and IFT. The in vitro data have predictive value in planta and SEQ ID NO:24 provides improved tolerance to mesotrione and IFT but not, for example, to tembotrione.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

That which is claimed:

1. An expression cassette comprising a polynucleotide encoding a polypeptide operably linked to a heterologous promoter that drives expression in a plant or plant cell, wherein said polypeptide is plant-derived and has 4-hydroxyphenylpyruvate dioxygenase (HPPD) enzymatic activity and comprises at least one of the following amino acid sequences:
   i. GVRRIAGDV (SEQ ID NO:61), wherein I is replaced with A, N, D, C, E, Q, G, H, K, M, F, P, S, T, W, Y or V;
   ii. G(I,V) LVD(R,K)D (SEQ ID NO:30), wherein L is replaced with any other amino acid;
   iii. GFGKGNFSE (SEQ ID NO:70), wherein the second G is replaced with any other amino acid;
   iv. GGCGGFGKG (SEQ ID NO:68), wherein the fourth G is replaced with any other amino acid; and
   v. FEFMAPPQA (SEQ ID NO:58), wherein the first A is replaced with any other amino acid.

2. The expression cassette of claim 1, wherein the polynucleotide sequence is optimized for expression in a plant.

3. The expression cassette of claim 1 further comprising an operably linked polynucleotide sequence encoding a polypeptide that confers a desirable trait.

4. The expression cassette of claim 3, wherein said desirable trait is resistance or tolerance to an herbicide.

5. The expression cassette of claim 4, wherein said desirable trait is resistance or tolerance to an HPPD inhibitor, glyphosate, or glufosinate.

6. The expression cassette of claim 5, wherein said polypeptide that confers a desirable trait is a cytochrome P450 or variant thereof.

7. The expression cassette of claim 5, wherein said polypeptide that confers a desirable trait is an EPSPS (5-enolpyrovyl-shikimate-3-phosphate-synthase).

8. The expression cassette of claim 5, wherein said polypeptide that confers a desirable trait is a phosphinothricin acetyl transferase.

9. A vector comprising an expression cassette according to claim 1.

10. A method for conferring resistance or tolerance to an HPPD inhibitor in a plant, said method comprising introducing into said plant at least one expression cassette according to claim 1.

11. A transformed plant cell comprising at least one expression cassette according to claim 1.

12. The plant cell of claim 11, wherein said plant cell is a rice, barley, potato, sweet potato, canola, sunflower, rye, oats, wheat, corn, soybean, sugar beet, tobacco, *Miscanthus* grass, Switch grass, safflower, trees, cotton, cassava, tomato, sorghum, alfalfa, sugar beet, and sugarcane plant cell.

13. The plant cell of claim 12, wherein said plant cell is a soybean plant cell.

14. A plant, plant part, or seed comprising the plant cell of claim 11.

15. A method of controlling weeds at a locus, said method comprising applying to said locus a weed-controlling amount of one or more HPPD inhibitors, wherein said locus comprises a plant according to claim 14.

16. The method of claim 15, wherein said HPPD inhibitor is selected from the group consisting of:

a) a compound of formula (Ia)

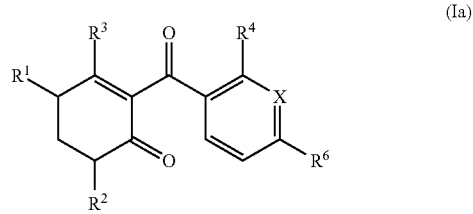

wherein $R^1$ and $R^2$ are hydrogen or together form an ethylene bridge;
$R^3$ is hydroxy or phenylthio-; $R^4$ is halogen, nitro, $C_1$-$C_4$alkyl, $C_1$-$C_4$alkoxy-$C_1$-$C_4$alkyl-, $C_1$-$C_4$alkoxy-$C_1$-$C_4$alkoxy-$C_1$-$C_4$alkyl-;
X is methine, nitrogen, or C—$R^5$ wherein $R^5$ is hydrogen, $C_1$-$C_4$alkoxy, $C_1$-$C_4$haloalkoxy-$C_1$-$C_4$alkyl-, or a group

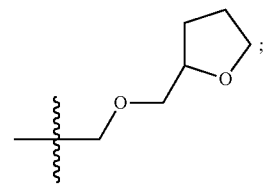

and
$R^6$ is $C_1$-$C_4$alkylsulfonyl- or $C_1$-$C_4$haloalkyl;

b) a compound of formula (Ib)

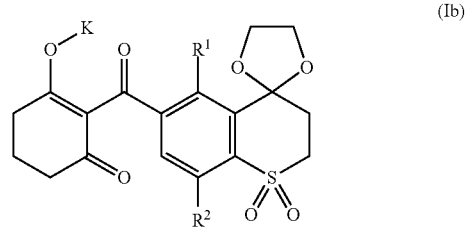

$R^1$ and $R^2$ are independently $C_1$-$C_4$alkyl; and the free acids thereof;

c) a compound of formula (Ic)

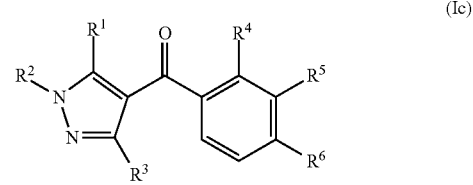

wherein $R^1$ is hydroxy, phenylcarbonyl-$C_1$-$C_4$alkoxy- or phenylcarbonyl-$C_1$-$C_4$alkoxy- wherein the phenyl moiety is substituted in para-position by halogen or $C_1$-$C_4$alkyl, or phenylsulfonyloxy- or phenylsulfonyloxy- wherein the phenyl moiety is substituted in para-position by halogen or $C_1$-$C_4$alkyl;

$R^2$ is $C_1$-$C_4$alkyl;

$R^3$ is hydrogen or $C_1$-$C_4$alkyl; $R^4$ and $R^6$ are independently halogen, $C_1$-$C_4$alkyl, $C_1$-$C_4$haloalkyl, or $C_1$-$C_4$alkylsulfonyl-; and $R^5$ is hydrogen, $C_1$-$C_4$alkyl, $C_1$-$C_4$alkoxy-$C_1$-$C_4$alkoxy-, or a group

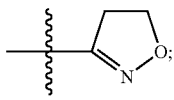 [SMILES: *C1=NOCC1]

d) a compound of formula (Id)

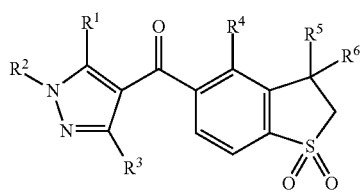

(Id)

wherein $R^1$ is hydroxy;

$R^2$ is $C_1$-$C_4$alkyl;

$R^3$ is hydrogen; and $R^4$, $R^5$ and $R^6$ are independently $C_1$-$C_4$alkyl;

e) a compound of formula (Ie)

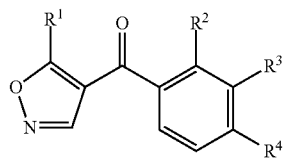

(Ie)

wherein $R^1$ is cyclopropyl;

$R^2$ and $R^4$ are independently halogen, $C_1$-$C_4$haloalkyl, or $C_1$-$C_4$alkylsulfonyl-; and $R^3$ is hydrogen;

f) a compound of formula (If)

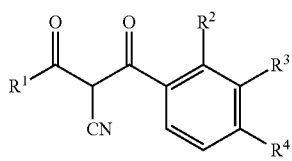

(If)

wherein $R^1$ is cyclopropyl;

$R^2$ and $R^4$ are independently halogen, $C_1$-$C_4$haloalkyl, or $C_1$-$C_4$alkylsulfonyl-; and $R^3$ is hydrogen; and g) a compound of formula (Ig) or Formula (Ih)

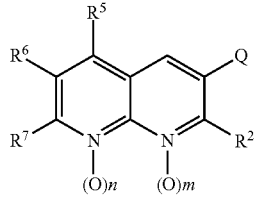

(Ig)

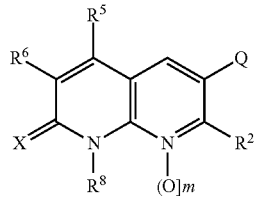

(Ih)

wherein:

$R^2$ is selected from the group consisting of $C_1$-$C_3$alkyl, $C_1$-$C_3$haloalkyl, $C_1$-$C_3$alkoxy-$C_1$-$C_3$ alkyl and $C_1$-$C_3$alkoxy-$C_2$-$C_3$alkoxy-$C_1$-$C_3$-alkyl;

$R^5$ is hydrogen or methyl;

$R^6$ is selected from the group consisting of hydrogen, fluorine, chlorine, hydroxyl and methyl;

$R^7$ is selected from the group consisting of hydrogen, halogen, hydroxyl, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, $C_3$-$C_6$alkynyl, $C_1$-$C_6$alkoxy, $C_4$-$C_7$cycloalkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, amino, $C_1$-$C_6$alkylamino, $C_2$-$C_6$dialkylamino, $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-R', $C_1$-$C_4$alkyleneyl-$CO_2$—R', $C_1$-$C_4$alkyleneyl-(CO)N—R'R', phenyl, phenylthio, phenylsulfinyl, phenylsulfonyl, phenoxy, pyrrolidinyl, piperidinyl, morpholinyl and 5 or 6-membered heteroaryl or heteroaryloxy, the heteroaryl containing one to three heteroatoms, each independently selected from the group consisting of oxygen, nitrogen and sulphur, wherein the phenyl or heteroaryl component may be optionally substituted by a substituent selected from the group consisting of $C_1$-$C_3$alkyl, $C_1$-$C_3$haloalkyl, $C_1$-$C_3$ alkoxy, $C_1$-$C_3$haloalkoxy, halo, cyano, and nitro;

X=O or S;

n=0 or 1;

m=0 or 1 with the proviso that if m=1 then n=0 and if n=1 then m=0;

p=0, 1, or 2;

R' is independently selected from the group consisting of hydrogen and $C_1$-$C_6$alkyl;

$R^8$ is selected from the group consisting of hydrogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkylalkeneyl for example cyclohexylmethylenyl, $C_3$-$C_6$alkynylalkyleneyl for example propargyl, $C_2$-$C_6$-alkenylalkylenyl for example allyl, $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with a substituent selected from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with a substituent selected from the group consisting of halo, $C_1$-$C_3$-alkoxy, $C_1$-$C_3$-alkyl, $C_1$-$C_3$ haloalkyl), $C_1$-$C_6$alkoxy $C_1$-$C_6$alkoxy $C_1$-$C_6$alkyl and a 5 or 6-membered heteroaryl-$C_1$-$C_3$-alkyl or heterocyclyl-$C_1$-$C_3$-alkyl, the heteroaryl or heterocyclyl containing one to three heteroatoms, each independently selected from the group consisting of oxygen, nitrogen and sulphur, wherein the heterocyclyl or heteroaryl component may be optionally substituted by a substituent selected from the group consisting of halo, $C_1$-$C_3$alkyl, $C_1$-$C_3$haloalkyl, and $C_1$-$C_3$ alkoxy;

Q is selected from the group consisting of:

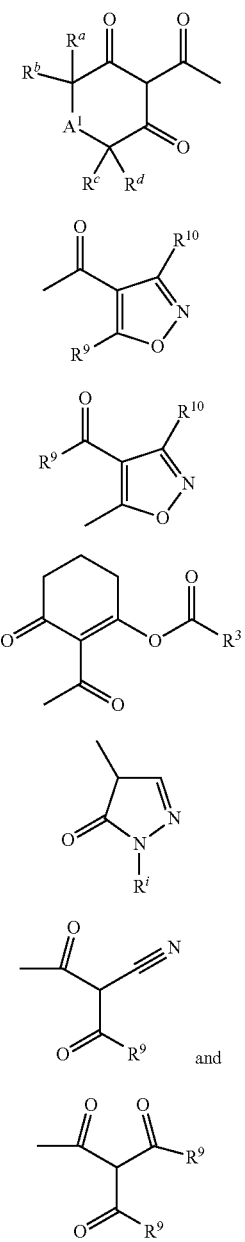

wherein
$A^1$ is selected from the group consisting of O, C(O), S, SO, $SO_2$ and $(CR^eR^f)_q$;

q=0, 1 or 2;
$R^a$, $R^b$, $R^c$, $R^d$, $R^e$ and $R^f$ are each independently selected from the group consisting of $C_1$-$C_4$alkyl which may be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl and heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or
$R^a$, $R^b$, $R^c$, $R^d$, $R^e$ and $R^f$ are each independently selected from the group consisting of hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on the nitrogen in the heterocyclic ring being other than halogen; or
$R^a$ and $R^b$ together form a 3- to 5-membered carbocyclic ring which may be substituted by $C_1$-$C_4$alkyl and may be interrupted by oxygen, sulfur, S(O), $SO_2$, OC(O), $NR^g$ or by C(O); or
$R^a$ and $R^c$ together form a $C_1$-$C_3$alkylene chain which may be interrupted by oxygen, sulfur, SO, $SO_2$, OC(O), $NR^h$ or by C(O); it being possible for that $C_1$-$C_3$alkylene chain in turn to be substituted by $C_1$-$C_4$alkyl;
$R^g$ and $R^h$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl;
$R^i$ is $C_1$-$C_4$alkyl;
$R^3$ is selected from the group consisting of $C_1$-$C_6$alkyl, optionally substituted with halogen and/or $C_1$-$C_3$alkoxy; and $C_3$-$C_6$ cycloalkyl optionally substituted with halogen and/or $C_1$-$C_3$alkoxy;
$R^9$ is selected from the group consisting of cyclopropyl, $CF_3$ and i.-Pr;
$R^{10}$ is selected from the group consisting of hydrogen, I, Br, $SR^{11}$, $S(O)R^{11}$, $S(O)_2R^{11}$ and $CO_2R^{11}$; and
$R^{11}$ is $C_{1-4}$ alkyl.

17. The method of claim 16, wherein said HPPD inhibitor is mesotrione.

18. The expression cassette of claim 1, where in the encoded polypeptide has at least 70% sequence identity to SEQ ID NO:27.

19. The expression cassette of claim 1, wherein the I of SEQ ID NO:61 in sub-part i. is replaced with C, D or E in the encoded polypeptide.

20. The expression cassette of claim 18, wherein the I of SEQ ID NO:61 in sub-part i. is replaced with C, D or E in the encoded polypeptide.

21. The expression cassette of claim 1, wherein the L of SEQ ID NO: 30 of sub-part ii. is replaced with M or A in the encoded polypeptide.

22. The expression cassette of claim 18, wherein the L of SEQ ID NO: 30 of sub-part ii. is replaced with M or A in the encoded polypeptide.

23. The expression cassette of claim 1, wherein the second G of SEQ ID NO: 70 in sub-part iii. is replaced with I, A or S in the encoded polypeptide.

24. The expression cassette of claim 18, wherein the second G of SEQ ID NO: 70 in sub-part iii. is replaced with I, A or S in the encoded polypeptide.

25. The expression cassette of claim 1, wherein the fourth G of SEQ ID NO: 68 in part iv. is replaced with S, A or T in the encoded polypeptide.

26. The expression cassette of claim 18, wherein the fourth G of SEQ ID NO: 68 in part iv. is replaced with S, A or T in the encoded polypeptide.

27. The expression cassette of claim 1, wherein the first A of SEQ ID NO: 58 in sub-part v. is replaced with R, K or P in the encoded polypeptide.

28. The expression cassette of claim 18, wherein the first A of SEQ ID NO: 58 in sub-part v. is replaced with R, K or P in the encoded polypeptide.

29. The expression cassette of claim 1, wherein the polypeptide additionally comprises the amino acid sequence RFDHWGNV (SEQ ID NO:38), wherein the first V is replaced with L or I.

30. The expression cassette of claim 1, wherein the polypeptide comprises at least two of the amino acid sequences found in sub-parts i-v.

31. The expression cassette of claim 1, wherein the polypeptide comprises at least three of the amino acid sequences found in sub-parts i-v.

32. The expression cassette of claim 1, wherein the polypeptide comprises at least four of the amino acid sequences found in sub-parts i-v.

33. The expression cassette of claim 1, wherein the polypeptide comprises all five of the amino acid sequences found in sub-parts i-v.

\* \* \* \* \*